US008401666B2

(12) United States Patent
Skelton et al.

(10) Patent No.: US 8,401,666 B2
(45) Date of Patent: Mar. 19, 2013

(54) MODIFICATION PROFILES FOR POSTURE-RESPONSIVE THERAPY

(75) Inventors: Dennis M. Skelton, Bloomington, MN (US); Jon P. Davis, St. Michael, MN (US); Rajeev Sahasrabudhe, Maple Grove, MN (US); Shyam Gokaldas, New Brighton, MN (US); Joseph J. Nolan, Minnetonka, MN (US); Dennis Bourget, St. Michael, MN (US); Duane Bourget, Albertville, MN (US); Keith A. Miesel, St. Paul, MN (US); James Zimmerman, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 833 days.

(21) Appl. No.: 12/433,856

(22) Filed: Apr. 30, 2009

(65) Prior Publication Data

US 2010/0010392 A1   Jan. 14, 2010

Related U.S. Application Data

(60) Provisional application No. 61/080,070, filed on Jul. 11, 2008.

(51) Int. Cl.
*A61N 1/365* (2006.01)
(52) U.S. Cl. ............... 607/62; 607/17; 607/18; 607/19; 607/20
(58) Field of Classification Search ............. 607/17–20, 607/62
See application file for complete search history.

(56) References Cited

U.S. PATENT DOCUMENTS

| 4,297,685 A | 10/1981 | Brainard, II |
| 4,365,633 A | 12/1982 | Loughman |
| 4,543,955 A | 10/1985 | Schroeppel |

(Continued)

FOREIGN PATENT DOCUMENTS

| DE | 19831109 | 1/2000 |
| DE | 10024103 | 11/2001 |

(Continued)

OTHER PUBLICATIONS

"Analysis of heart rate dynamics by methods derived from non-linear mathematics: Clinical applicability and prognostic significance," http://herkules.oulu.fi.isbn9514250133/html, 4 pp., 2004.

(Continued)

*Primary Examiner* — Joseph Stoklosa
(74) *Attorney, Agent, or Firm* — Shumaker & Sieffert, PA

(57) ABSTRACT

In general, the disclosure describes techniques for modifying therapy provided to a patient by a medical device. The techniques may be applicable to electrical stimulation therapy or other therapies. Modification of therapy may include adjustment of one or more therapy parameter values that define one or more characteristics of stimulation therapy delivered to a patient. The therapy modification may be based on activity of a patient that is detected by an IMD, such as a change in a detected posture state occupied by the patient. Different therapy modifications may be applied for different changes in detected posture state. An IMD may modify therapy based on a transition from one posture state to another posture state, and apply different modifications for different transitions. In some aspects, the modification may include a profile, such as a ramp up or ramp down in a parameter value over a period of time. The profile may be different for different posture transitions. A ramp slope may be steeper for one transition than for another transition. When a patient transitions from an upright to a lying posture state, for example, the profile may be especially abrupt. In some examples, a modification profile may define a dwell time.

42 Claims, 19 Drawing Sheets

U.S. PATENT DOCUMENTS

| | | |
|---|---|---|
| 4,550,736 A | 11/1985 | Broughton et al. |
| 4,566,456 A | 1/1986 | Koning et al. |
| 4,771,780 A | 9/1988 | Sholder |
| 4,776,345 A | 10/1988 | Cohen et al. |
| 4,846,180 A | 7/1989 | Buffet |
| 4,846,195 A | 7/1989 | Alt |
| 5,031,618 A | 7/1991 | Mullett |
| 5,040,534 A | 8/1991 | Mann et al. |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,158,078 A | 10/1992 | Bennett et al. |
| 5,167,229 A | 12/1992 | Peckham et al. |
| 5,233,984 A | 8/1993 | Thompson |
| 5,275,159 A | 1/1994 | Griebel |
| 5,312,446 A | 5/1994 | Holschbach et al. |
| 5,335,657 A | 8/1994 | Terry, Jr. et al. |
| 5,337,758 A | 8/1994 | Moore et al. |
| 5,342,409 A | 8/1994 | Mullett |
| 5,354,317 A | 10/1994 | Alt |
| 5,425,750 A | 6/1995 | Moberg |
| 5,476,483 A | 12/1995 | Bornzin et al. |
| 5,487,755 A | 1/1996 | Snell et al. |
| 5,513,645 A | 5/1996 | Jacobson et al. |
| 5,514,162 A | 5/1996 | Bornzin et al. |
| 5,558,640 A | 9/1996 | Pfeiler et al. |
| 5,562,707 A | 10/1996 | Prochazka et al. |
| 5,593,431 A * | 1/1997 | Sheldon ................... 607/19 |
| 5,622,428 A | 4/1997 | Bonnet |
| 5,628,317 A | 5/1997 | Starkebaum et al. |
| 5,643,332 A | 7/1997 | Stein |
| 5,645,053 A | 7/1997 | Remmers et al. |
| 5,674,258 A | 10/1997 | Henschel et al. |
| 5,711,316 A | 1/1998 | Elsberry et al. |
| 5,720,770 A | 2/1998 | Nappholz et al. |
| 5,732,696 A | 3/1998 | Rapoport et al. |
| 5,741,310 A | 4/1998 | Wittkampf |
| 5,782,884 A | 7/1998 | Stotts et al. |
| 5,814,093 A | 9/1998 | Stein |
| 5,832,932 A | 11/1998 | Elsberry et al. |
| 5,833,709 A | 11/1998 | Rise et al. |
| 5,836,989 A | 11/1998 | Shelton |
| 5,851,193 A | 12/1998 | Arikka et al. |
| 5,865,760 A | 2/1999 | Lidman et al. |
| 5,885,471 A | 3/1999 | Ruben et al. |
| 5,893,883 A | 4/1999 | Torgerson et al. |
| 5,895,371 A | 4/1999 | Levitas et al. |
| 5,904,708 A | 5/1999 | Goedeke |
| 5,911,738 A | 6/1999 | Sikorski et al. |
| 5,913,727 A | 6/1999 | Ahdoot |
| 5,919,149 A | 7/1999 | Allum |
| 5,938,690 A | 8/1999 | Law et al. |
| 5,941,906 A | 8/1999 | Barreras, Sr. et al. |
| 5,944,680 A | 8/1999 | Christopherson et al. |
| 5,957,957 A | 9/1999 | Sheldon |
| 6,027,456 A | 2/2000 | Feler et al. |
| 6,038,475 A | 3/2000 | Sikorski et al. |
| 6,044,297 A * | 3/2000 | Sheldon et al. ................ 607/17 |
| 6,045,513 A | 4/2000 | Stone et al. |
| 6,059,576 A | 5/2000 | Brann |
| 6,095,991 A | 8/2000 | Krausman et al. |
| 6,099,479 A | 8/2000 | Christopherson et al. |
| 6,102,874 A | 8/2000 | Stone et al. |
| 6,120,467 A | 9/2000 | Schallhorn |
| 6,128,534 A | 10/2000 | Park et al. |
| 6,134,459 A | 10/2000 | Roberts et al. |
| 6,157,857 A | 12/2000 | Dimpfel |
| 6,165,143 A | 12/2000 | Van Lummel |
| 6,216,537 B1 | 4/2001 | Henschel et al. |
| 6,259,948 B1 | 7/2001 | Florio et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,308,099 B1 | 10/2001 | Fox et al. |
| 6,315,740 B1 | 11/2001 | Singh |
| 6,327,501 B1 | 12/2001 | Levine et al. |
| 6,341,236 B1 | 1/2002 | Osorio et al. |
| 6,351,672 B1 | 2/2002 | Park et al. |
| 6,368,284 B1 | 4/2002 | Bardy |
| 6,381,496 B1 | 4/2002 | Meadows et al. |
| 6,393,325 B1 | 5/2002 | Mann et al. |
| 6,438,408 B1 | 8/2002 | Mulligan et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,507,757 B1 | 1/2003 | Swain et al. |
| 6,514,218 B2 | 2/2003 | Yamamoto |
| 6,516,749 B1 | 2/2003 | Salasidis |
| 6,539,249 B1 | 3/2003 | Kadhiresan et al. |
| 6,547,755 B1 | 4/2003 | Lippe et al. |
| 6,572,557 B2 | 6/2003 | Tchou et al. |
| 6,574,507 B1 | 6/2003 | Bonnet |
| 6,605,038 B1 | 8/2003 | Teller et al. |
| 6,609,031 B1 | 8/2003 | Law et al. |
| 6,611,783 B2 | 8/2003 | Kelly, Jr. et al. |
| 6,620,151 B2 | 9/2003 | Blischak et al. |
| 6,625,493 B2 | 9/2003 | Kroll et al. |
| 6,635,048 B1 | 10/2003 | Ullestad et al. |
| 6,641,542 B2 | 11/2003 | Cho et al. |
| 6,658,292 B2 | 12/2003 | Kroll et al. |
| 6,659,968 B1 | 12/2003 | McClure |
| 6,662,047 B2 | 12/2003 | Sorensen |
| 6,665,558 B2 | 12/2003 | Kalgren et al. |
| 6,668,188 B2 | 12/2003 | Sun et al. |
| 6,687,538 B1 | 2/2004 | Hrdlicka et al. |
| 6,731,984 B2 | 5/2004 | Cho et al. |
| 6,740,075 B2 | 5/2004 | Lebel et al. |
| 6,748,276 B1 | 6/2004 | Daignault, Jr. et al. |
| 6,751,503 B1 | 6/2004 | Kroll |
| 6,752,766 B2 | 6/2004 | Kowallik et al. |
| 6,773,404 B2 | 8/2004 | Poezevera et al. |
| 6,782,315 B2 | 8/2004 | Lu et al. |
| 6,817,979 B2 | 11/2004 | Nihtilä |
| 6,820,025 B2 | 11/2004 | Bachmann et al. |
| 6,829,507 B1 | 12/2004 | Lidman et al. |
| 6,832,113 B2 | 12/2004 | Belalcazar |
| 6,834,436 B2 | 12/2004 | Townsend |
| 6,853,863 B2 | 2/2005 | Carter et al. |
| 6,878,121 B2 | 4/2005 | Krausman et al. |
| 6,884,596 B2 | 4/2005 | Civelli et al. |
| 6,890,306 B2 | 5/2005 | Poezevera |
| 6,895,341 B2 | 5/2005 | Barrey et al. |
| 6,922,587 B2 | 7/2005 | Weinberg |
| 6,923,784 B2 | 8/2005 | Stein |
| 6,928,324 B2 | 8/2005 | Park et al. |
| 6,937,899 B2 | 8/2005 | Sheldon et al. |
| 6,937,900 B1 | 8/2005 | Pianca et al. |
| 6,945,934 B2 | 9/2005 | Bardy |
| 6,964,641 B2 | 11/2005 | Cho et al. |
| 6,975,904 B1 | 12/2005 | Sloman |
| 6,997,882 B1 | 2/2006 | Parker et al. |
| 6,999,817 B2 | 2/2006 | Park et al. |
| 7,016,730 B2 | 3/2006 | Ternes |
| 7,031,772 B2 | 4/2006 | Condie |
| 7,043,305 B2 | 5/2006 | KenKnight et al. |
| 7,054,687 B1 | 5/2006 | Andersen |
| 7,066,910 B2 | 6/2006 | Bauhahn et al. |
| 7,082,333 B1 | 7/2006 | Bauhahn |
| 7,092,759 B2 | 8/2006 | Nehls et al. |
| 7,095,424 B2 | 8/2006 | Satoh et al. |
| 7,110,820 B2 | 9/2006 | Tcheng et al. |
| 7,117,036 B2 | 10/2006 | Florio |
| 7,123,967 B2 | 10/2006 | Weinberg |
| 7,130,681 B2 | 10/2006 | Gebhardt et al. |
| 7,130,689 B1 | 10/2006 | Turcott |
| 7,141,026 B2 | 11/2006 | Aminian et al. |
| 7,142,921 B2 | 11/2006 | Mattes et al. |
| 7,149,579 B1 | 12/2006 | Koh et al. |
| 7,149,584 B1 | 12/2006 | Koh et al. |
| 7,151,961 B1 | 12/2006 | Whitehurst et al. |
| 7,155,279 B2 | 12/2006 | Whitehurst et al. |
| 7,160,252 B2 | 1/2007 | Cho et al. |
| 7,162,304 B1 | 1/2007 | Bradley |
| 7,167,743 B2 | 1/2007 | Heruth et al. |

| Patent | Date | Inventor |
|---|---|---|
| 7,167,751 B1 | 1/2007 | Whitehurst et al. |
| 7,181,281 B1 | 2/2007 | Kroll |
| 7,189,204 B2 | 3/2007 | Ni et al. |
| 7,207,947 B2 | 4/2007 | Koh et al. |
| 7,210,240 B2 | 5/2007 | Townsend et al. |
| 7,212,862 B2 | 5/2007 | Park et al |
| 7,214,197 B2 | 5/2007 | Prass |
| 7,218,964 B2 | 5/2007 | Hill et al. |
| 7,218,968 B2 | 5/2007 | Condie et al. |
| 7,221,979 B2 | 5/2007 | Zhou et al. |
| 7,231,254 B2 | 6/2007 | DiLorenzo |
| 7,242,983 B2 | 7/2007 | Frei et al. |
| 7,252,640 B2 | 8/2007 | Ni et al. |
| 7,266,412 B2 | 9/2007 | Stypulkowski |
| 7,308,311 B2 | 12/2007 | Sorensen et al. |
| 7,313,440 B2 | 12/2007 | Miesel |
| 7,317,948 B1 | 1/2008 | King et al. |
| 7,330,760 B2 * | 2/2008 | Heruth et al. .................. 607/17 |
| 7,366,569 B2 | 4/2008 | Belalcazar |
| 7,366,572 B2 | 4/2008 | Heruth et al. |
| 7,387,610 B2 | 6/2008 | Stahmann |
| 7,389,147 B2 | 6/2008 | Wahlstrand et al. |
| 7,395,113 B2 | 7/2008 | Heruth |
| 7,403,820 B2 | 7/2008 | DiLorenzo |
| 7,406,351 B2 | 7/2008 | Wesselink |
| 7,415,308 B2 | 8/2008 | Gerber et al. |
| 7,447,545 B2 | 11/2008 | Heruth et al. |
| 7,471,290 B2 | 12/2008 | Wang et al. |
| 7,471,980 B2 | 12/2008 | Koshiol |
| 7,489,970 B2 | 2/2009 | Lee et al. |
| 7,491,181 B2 | 2/2009 | Heruth et al. |
| 7,505,815 B2 | 3/2009 | Lee et al. |
| 7,519,431 B2 | 4/2009 | Goetz et al. |
| 7,542,803 B2 | 6/2009 | Heruth et al. |
| 7,548,786 B2 | 6/2009 | Lee et al. |
| 7,559,901 B2 | 7/2009 | Maile |
| 7,572,225 B2 | 8/2009 | Stahmann |
| 7,577,479 B2 | 8/2009 | Hartley et al. |
| 7,580,752 B2 | 8/2009 | Gerber et al. |
| 7,584,808 B2 | 9/2009 | Dolgin et al. |
| 7,590,453 B2 | 9/2009 | Heruth |
| 7,590,455 B2 | 9/2009 | Heruth et al. |
| 7,590,481 B2 | 9/2009 | Lu et al. |
| 7,591,265 B2 | 9/2009 | Lee et al. |
| 7,603,170 B2 | 10/2009 | Hatlestad et al. |
| 7,623,919 B2 | 11/2009 | Goetz et al. |
| 7,634,379 B2 | 12/2009 | Noble |
| 7,664,546 B2 | 2/2010 | Hartley et al. |
| 7,672,806 B2 | 3/2010 | Tronconi |
| 7,717,848 B2 | 5/2010 | Heruth et al. |
| 7,769,464 B2 | 8/2010 | Gerber et al. |
| 7,792,583 B2 | 9/2010 | Heruth et al. |
| 7,996,070 B2 * | 8/2011 | van Dam et al. ............. 600/509 |
| 2002/0038137 A1 | 3/2002 | Stein |
| 2002/0091308 A1 | 7/2002 | Kipshidze et al. |
| 2002/0107553 A1 | 8/2002 | Hill et al. |
| 2002/0115939 A1 | 8/2002 | Mulligan et al. |
| 2002/0165586 A1 | 11/2002 | Hill et al. |
| 2002/0169485 A1 | 11/2002 | Pless et al. |
| 2002/0170193 A1 | 11/2002 | Townsend et al. |
| 2003/0004423 A1 | 1/2003 | Lavie et al. |
| 2003/0036783 A1 | 2/2003 | Bauhahn et al. |
| 2003/0045910 A1 | 3/2003 | Sorensen et al. |
| 2003/0065370 A1 | 4/2003 | Lebel et al. |
| 2003/0088185 A1 | 5/2003 | Prass |
| 2003/0149457 A1 | 8/2003 | Tcheng et al. |
| 2003/0171791 A1 | 9/2003 | KenKnight et al. |
| 2003/0181960 A1 | 9/2003 | Carter et al. |
| 2003/0204211 A1 | 10/2003 | Condie et al. |
| 2004/0015103 A1 | 1/2004 | Aminian et al. |
| 2004/0049132 A1 | 3/2004 | Barron et al. |
| 2004/0088020 A1 | 5/2004 | Condie et al. |
| 2004/0102814 A1 | 5/2004 | Sorensen et al. |
| 2004/0133248 A1 | 7/2004 | Frei et al. |
| 2004/0138716 A1 | 7/2004 | Kon et al. |
| 2004/0147975 A1 | 7/2004 | Popovic et al. |
| 2004/0199215 A1 | 10/2004 | Lee et al. |
| 2004/0199216 A1 | 10/2004 | Lee et al. |
| 2004/0199217 A1 | 10/2004 | Lee et al. |
| 2004/0199218 A1 | 10/2004 | Lee et al. |
| 2004/0215286 A1 | 10/2004 | Stypulkowski |
| 2004/0220621 A1 | 11/2004 | Zhou et al. |
| 2004/0225332 A1 | 11/2004 | Gebhardt et al. |
| 2004/0257693 A1 | 12/2004 | Ehrlich |
| 2005/0042589 A1 | 2/2005 | Hatlestad et al. |
| 2005/0043767 A1 | 2/2005 | Belalcazar |
| 2005/0060001 A1 | 3/2005 | Singhal et al. |
| 2005/0061320 A1 | 3/2005 | Lee et al. |
| 2005/0113710 A1 | 5/2005 | Stahmann et al. |
| 2005/0113887 A1 | 5/2005 | Bauhahn |
| 2005/0126026 A1 | 6/2005 | Townsend et al. |
| 2005/0137627 A1 | 6/2005 | Koshiol et al. |
| 2005/0145246 A1 | 7/2005 | Hartley et al. |
| 2005/0172311 A1 | 8/2005 | Hjelt et al. |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222638 A1 | 10/2005 | Foley et al. |
| 2005/0228455 A1 | 10/2005 | Kramer et al. |
| 2005/0234514 A1 | 10/2005 | Heruth et al. |
| 2005/0234518 A1 | 10/2005 | Heruth et al. |
| 2005/0240242 A1 | 10/2005 | DiLorenzo |
| 2005/0245988 A1 | 11/2005 | Miesel |
| 2005/0283210 A1 | 12/2005 | Blischak et al. |
| 2006/0190049 A1 | 8/2006 | Gerber et al. |
| 2006/0190050 A1 | 8/2006 | Gerber et al. |
| 2006/0190051 A1 | 8/2006 | Gerber et al. |
| 2006/0195051 A1 | 8/2006 | Schnapp et al. |
| 2006/0206167 A1 | 9/2006 | Flaherty et al. |
| 2006/0212080 A1 | 9/2006 | Hartley et al. |
| 2006/0213267 A1 | 9/2006 | Tronconi et al. |
| 2006/0235289 A1 | 10/2006 | Wesselink et al. |
| 2006/0235472 A1 | 10/2006 | Goetz et al. |
| 2006/0241513 A1 | 10/2006 | Hatlestad et al. |
| 2006/0247732 A1 | 11/2006 | Wesselink |
| 2006/0247739 A1 | 11/2006 | Wahlstrand et al. |
| 2006/0259099 A1 | 11/2006 | Goetz et al. |
| 2006/0262120 A1 | 11/2006 | Rosenberg |
| 2006/0265025 A1 | 11/2006 | Goetz et al. |
| 2006/0276848 A1 | 12/2006 | Min et al. |
| 2006/0287686 A1 | 12/2006 | Cullen et al. |
| 2007/0015976 A1 | 1/2007 | Miesel et al. |
| 2007/0038265 A1 | 2/2007 | Tcheng et al. |
| 2007/0050174 A1 | 3/2007 | Behar |
| 2007/0073355 A1 | 3/2007 | DiLorenzo et al. |
| 2007/0115277 A1 | 5/2007 | Wang et al. |
| 2007/0118056 A1 | 5/2007 | Wang et al. |
| 2007/0123758 A1 | 5/2007 | Miesel et al. |
| 2007/0129622 A1 | 6/2007 | Bourget et al. |
| 2007/0129641 A1 | 6/2007 | Sweeney |
| 2007/0129769 A1 | 6/2007 | Bourget et al. |
| 2007/0129774 A1 | 6/2007 | Bourget et al. |
| 2007/0150026 A1 * | 6/2007 | Bourget et al. ................ 607/46 |
| 2007/0150029 A1 | 6/2007 | Bourget et al. |
| 2007/0213789 A1 | 9/2007 | Nolan et al. |
| 2007/0249968 A1 | 10/2007 | Miesel et al. |
| 2007/0250121 A1 | 10/2007 | Miesel et al. |
| 2007/0250134 A1 | 10/2007 | Miesel et al. |
| 2007/0255118 A1 | 11/2007 | Miesel et al. |
| 2007/0255154 A1 | 11/2007 | Lu et al. |
| 2007/0265664 A1 | 11/2007 | Gerber et al. |
| 2007/0265681 A1 | 11/2007 | Gerber et al. |
| 2007/0276439 A1 | 11/2007 | Miesel et al. |
| 2007/0293737 A1 | 12/2007 | Heruth et al. |
| 2007/0293917 A1 | 12/2007 | Thompson |
| 2008/0071150 A1 | 3/2008 | Miesel et al. |
| 2008/0071324 A1 | 3/2008 | Miesel et al. |
| 2008/0071326 A1 | 3/2008 | Heruth et al. |
| 2008/0071327 A1 | 3/2008 | Miesel et al. |
| 2008/0079444 A1 | 4/2008 | Denison |

| | | |
|---|---|---|
| 2008/0081958 A1 | 4/2008 | Denison et al. |
| 2008/0114219 A1 | 5/2008 | Zhang et al. |
| 2008/0164979 A1 | 7/2008 | Otto |
| 2008/0177355 A1 | 7/2008 | Miesel et al. |
| 2008/0188901 A1 | 8/2008 | Sanghera et al. |
| 2008/0188909 A1 | 8/2008 | Bradley |
| 2008/0194998 A1 | 8/2008 | Holmstrom et al. |
| 2008/0204255 A1 | 8/2008 | Flexer et al. |
| 2008/0269812 A1 | 10/2008 | Gerber et al. |
| 2008/0269843 A1 | 10/2008 | Gerber |
| 2008/0281376 A1 | 11/2008 | Gerber et al. |
| 2008/0281379 A1 | 11/2008 | Wesselink |
| 2008/0281381 A1 | 11/2008 | Gerber et al. |
| 2008/0288200 A1 | 11/2008 | Noble |
| 2008/0300449 A1 | 12/2008 | Gerber et al. |
| 2008/0300470 A1 | 12/2008 | Gerber et al. |
| 2009/0030263 A1 | 1/2009 | Heruth et al. |
| 2009/0036951 A1 | 2/2009 | Heruth et al. |
| 2009/0046056 A1 | 2/2009 | Rosenberg et al. |
| 2009/0076343 A1 | 3/2009 | James et al. |
| 2009/0082829 A1 | 3/2009 | Panken et al. |
| 2009/0099627 A1 | 4/2009 | Molnar et al. |
| 2009/0105785 A1 | 4/2009 | Wei et al. |
| 2009/0118599 A1 | 5/2009 | Heruth et al. |
| 2009/0228841 A1 | 9/2009 | Hildreth |
| 2009/0233770 A1 | 9/2009 | Vincent et al. |
| 2009/0259216 A1 | 10/2009 | Drew et al. |
| 2009/0264789 A1 | 10/2009 | Molnar et al. |
| 2009/0306740 A1 | 12/2009 | Heruth et al. |
| 2010/0010380 A1 | 1/2010 | Panken et al. |
| 2010/0010381 A1 | 1/2010 | Skelton et al. |
| 2010/0010382 A1 | 1/2010 | Panken et al. |
| 2010/0010383 A1 | 1/2010 | Skelton et al. |
| 2010/0010384 A1 | 1/2010 | Panken et al. |
| 2010/0010385 A1 | 1/2010 | Skelton et al. |
| 2010/0010386 A1 | 1/2010 | Skelton et al. |
| 2010/0010387 A1 | 1/2010 | Skelton et al. |
| 2010/0010388 A1 | 1/2010 | Panken et al. |
| 2010/0010389 A1 | 1/2010 | Davis et al. |
| 2010/0010390 A1 | 1/2010 | Skelton et al. |
| 2010/0010391 A1 | 1/2010 | Skelton et al. |
| 2010/0010432 A1 | 1/2010 | Skelton et al. |
| 2010/0010571 A1 | 1/2010 | Skelton et al. |
| 2010/0010572 A1 | 1/2010 | Skelton et al. |
| 2010/0010573 A1 | 1/2010 | Skelton et al. |
| 2010/0010574 A1 | 1/2010 | Skelton et al. |
| 2010/0010575 A1 | 1/2010 | Skelton et al. |
| 2010/0010576 A1 | 1/2010 | Skelton et al. |
| 2010/0010577 A1 | 1/2010 | Skelton et al. |
| 2010/0010578 A1 | 1/2010 | Skelton et al. |
| 2010/0010579 A1 | 1/2010 | Skelton et al. |
| 2010/0010580 A1 | 1/2010 | Skelton et al. |
| 2010/0010583 A1 | 1/2010 | Panken et al. |
| 2010/0010584 A1 | 1/2010 | Skelton et al. |
| 2010/0010585 A1 | 1/2010 | Davis et al. |
| 2010/0010586 A1 | 1/2010 | Skelton et al. |
| 2010/0010587 A1 | 1/2010 | Skelton et al. |
| 2010/0010588 A1 | 1/2010 | Skelton et al. |
| 2010/0010589 A1 | 1/2010 | Skelton et al. |
| 2010/0010590 A1 | 1/2010 | Skelton et al. |
| 2010/0030286 A1 | 2/2010 | Goetz et al. |
| 2010/0121415 A1 | 5/2010 | Skelton et al. |
| 2010/0174155 A1 | 7/2010 | Heruth et al. |

FOREIGN PATENT DOCUMENTS

| | | |
|---|---|---|
| EP | 0564803 | 10/1993 |
| EP | 0845240 | 6/1998 |
| EP | 0849715 | 6/1998 |
| EP | 1195139 | 4/2002 |
| EP | 1291036 | 3/2003 |
| EP | 1308182 | 5/2003 |
| EP | 1391846 | 2/2004 |
| EP | 1437159 | 7/2004 |
| EP | 1731088 | 12/2006 |
| EP | 1870128 | 12/2007 |
| EP | 1938862 | 7/2008 |
| GB | 2330912 | 5/1999 |
| GB | 2408342 | 5/2005 |
| GB | 2447647 | 9/2008 |
| WO | 94/05371 | 3/1994 |
| WO | 96/29007 | 9/1996 |
| WO | 97/04705 | 2/1997 |
| WO | 97/49455 | 12/1997 |
| WO | 98/00197 | 1/1998 |
| WO | 99/56820 | 11/1999 |
| WO | 01/37930 | 5/2001 |
| WO | 02/28282 | 4/2002 |
| WO | 02/41771 | 5/2002 |
| WO | 02/087433 | 11/2002 |
| WO | 02/096512 | 12/2002 |
| WO | 02/100267 | 12/2002 |
| WO | 03/051356 | 6/2003 |
| WO | 03/065891 | 8/2003 |
| WO | 2005/028029 | 3/2005 |
| WO | 2005/035050 | 4/2005 |
| WO | 2005/079487 | 9/2005 |
| WO | 2005/089646 | 9/2005 |
| WO | 2005/089647 | 9/2005 |
| WO | 2005/089860 | 9/2005 |
| WO | 2005/102499 | 11/2005 |
| WO | 2005/120348 | 12/2005 |
| WO | 2007/009088 | 1/2007 |
| WO | 2007/051196 | 5/2007 |
| WO | 2007/064682 | 6/2007 |
| WO | 2007/064936 | 6/2007 |
| WO | 2008/026970 | 3/2008 |

OTHER PUBLICATIONS

"Design Competition: Runners-Up for the Best Three Designs," EPN, vol. 26, No. 1, 1 pg., 2002.

"IBM and Citizen Watch develop Linux-Based WatchPad," http://wwwlinuxdevices.com/news/NS6580187845.html, 5 pp., 2006.

"MiniMitter® Physiological and Behavioral Monitoring for Humans and Animals," http://www.minimitter.com/Products/Actiwatch, 3 pp., 2006.

"Watch," Wikipedia, 6 pp., http://en.wikipedia.org/wiki/Watch, 2006.

Aminian et al., "Physical Activity Monitoring Based on Accelerometry: Validation and Comparison with Video Observation," Medical & Biological Engineering and Computing, vol. 37, No. 2, pp. 304-308, 1999.

Amzica, "Physiology of Sleep and Wakefulness as it Relates to the Physiology of Epilepsy," Journal of Clinical Neurophysiology, American Clinical Neurophysiology Society, 19(6)1, pp. 488-503, 2002.

Ang et al., "Physical model of a MEMS accelerometer for low-g motion tracking applications," 2004 IEEE International Conference on Robotics and Automation, vol. 2, pp. 1345-1351, 2004.

Buchser et al., "Improved Physical Activity in Patients Treated for Chronic Pain by Spinal Cord Stimulation," Neuromodulation, vol. 8, Issue 1, pp. 40-48, Mar. 2005.

Crago et al., "An Elbow Extension Neuroprosthesis for Individuals with Tetraplegia," IEEE Transactions on Rehabilitation Engineering, vol. 6, No. 1, pp. 1-6, Mar. 1998.

Dejnabadi et al., "Estimation and Visualization of Sagittal Kinematics of Lower Limbs Orientation Using Body-Fixed Sensors," IEEE Transactions on Biomedical Engineering, vol. 53, No. 7, pp. 1385-1393, Jul. 2006.

Dinner, "Effect of Sleep on Epilepsy," Journal of Clinical Neurophysiology, American Clinical Neurophysiology Society, 19(6), pp. 504-513, 2002.

Foerster et al., "Motion Pattern and Posture: Correctly Assessed by Calibrated Accelerometers," Forschungsgrupe Psychophysiologie, Universität Freiburg, Germany, Mar. 2000, 28 pp.

Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, 2002.

Fourcade et al., "Modeling Phase Transitions in Human Posture," Studies in Perception and Action VII, Sheena Rogers & Judith Effken (eds), Lawrence Erlbaum Associated, Inc., pp. 99-103, 2003.

Giansanti et al., "The development and test of a device for the reconstruction of 3-D position and orientation by means of a kinematic sensor assembly with rate gyroscopes and accelerometers," IEEE Transactions on Biomedical Engineering, v. 52, No. 7, pp. 1271-1277, Jul. 2005.

Goodrich et al., "The Prediction of Pain Using Measures of Sleep Quality," Pain Digest, 8:23-25, 1998.

Heinz et al., "Using Wearable Sensors for Real-time Recognition Tasks in Games of Martial Arts—An Initial Experiment," Institute for Computer Systems and Networks (CSN), UMIT—University of Health Systems, Medical Informatics and Technology Hall in Tyrol, Austria, 2006 5 pp. http://eis.comp.lancs.ac.uk/fileadmin/relate/publication/2006-WearableSensors.pdf.

Hendelman et al., "Validity of Accelerometry for the Assessment of Moderate Intensity Physical Activity in the Field," Medicine & Science in Sports & Exercise, pp. S442-S449, 2000.

Hinckley, K., Pierce, J., Sinclair, M., Horvitz, E., *Sensing Techniques for Mobile Interaction*, ACM UIST 2000 Symposium on User Interface Software & Technology, CHI Letters 2 (2), pp. 91-100.

Husak, "Model of Tilt Sensor Systems," ICECS 2002, $9^{th}$ IEEE International Conference on Electronics, Circuits and Systems, vol. 1, pp. 227-230, 2002.

Karantonis et al., "Implementation of a Real-Time Human Movement Classifier Using a Triaxial Accelerometer for Ambulatory Monitoring," IEEE Transactions on Information Technology in Biomedicine, vol. 10, No. 1, pp. 156-167, Jan. 2006.

Kassam, "2005 EDP Topic "MK4": Tremor Data-Logger for Parkinson's Disease Patients," http://www.ee.ryerson.ca/~courses/cdp2005/MK4.html, 3 pp., 2005.

Kerr et al., "Analysis of the sit-stand-sit movement cycle in normal subjects," Clinical Biomechanics, vol. 12, No. 4, pp. 236-245, 1977.

Kiani et al., "Computerized Analysis of Daily Life Motor Activity for Ambulatory Monitoring," Technology and Health Care 5, pp. 307-318, 1997.

Kitchin et al., "Compensating for the 0 g Offset Drift of the ADXL50 Accelerometer," Analog Devices Application Note AN-380, 2 pp.

Lau, "Strategies for Generating Prolonged Functional Standing Using Intramuscular Stimulation or Intraspinal Microstimulation," IEEE Transactions on Neural Systems and Rehabilitation Engineering, vol. 15 No. 2, pp. 273-285, Jun. 2007.

Leiper et al., "Sensory Feedback for Head Control in Cerebral Palsy," Physical Therapy, vol. 61, No. 4, pp. 512-518, Apr. 1981.

Lorussi, "Wearable, Redundant Fabric-Based Sensor Arrays for Reconstruction of Body Segment Posture," IEEE Sensors Journal, vol. 4, No. 6, pp. 808-817, Dec. 2004.

Mathie et al., "A Pilot Study of Long-Term Monitoring of Human Movements in the Home Using Accelerometer," Journal of Telemedicine and Telecare 10:144-151, Jun. 2007.

Mathie et al., "Determining Activity Using a Triaxial Accelerometer," Proceedings of the Second Joint EMBS/BMES Conference, Houston, TX, pp. 2481-2482, Oct. 23-26, 2002.

Mattmann et al., "Recognizing Upper Body Postures Using Textile Strain Sensors," Proceedings Eleventh IEEE International Symposium on Wearable Computers, ISWC, pp. 29-36, 2007.

Mendez et al., "Interactions Between Sleep and Epilepsy," Journal of Clinical Neurophysiology, American Clinical Neurophysiology Society, 18(2), pp. 106-127, 2001.

Paraschiv-Ionescu et al., "Ambulatory System for the Quantitative and Qualitative Analysis of Patients Treated with Spinal Cord Stimulation," Gait and Posture, vol. 20, Issue 2, pp. 113-125, Oct. 2004.

Slyper et al., "Action Capture with Accelerometers," Eurographics/ACM SIGGRAPH Symposium on Computer Animation, Carnegie Mellon University, 7 pp. 2008.

Smith et al., "How do sleep disturbance and chronic pain inter-relate? Insights from the longitudinal and cognitive-behavioral clinical trials literature," Sleep Medicine Reviews, YSMRV 286, pp. 1-14, 2003.

Smith et al., "Presleep cognitions in Patients with Insomnia Secondary to Chronic Pain," Journal of Behavioral Medicine, vol. 24, No. 1, pp. 93-114, 2001.

Emmanuel Munguia Tapia, "Activity Recognition from Accelerometer Data for Videogame Applications," http://alumni.media.mit.edu/~emunguia/html/videogames.htm, 7 pp., Dec. 2, 2003, printed Oct. 1, 2009.

Trolier-Mckinstry et al., "Thin Film Piezoelectrics for MEMS," Journal of Electroceramics, v. 12, No. 1-2, pp. 7-17, Jan./Mar. 2004.

Tuck, "Implementing Auto-Zero Calibration Technique for Accelerometers," Freescale Semiconductor Application Note AN3447, 5 pp., Mar. 2007.

Tuisku, "Motor Activity Measured by Actometry in Neuropsychiatric Disorders," Department of Psychiatry, University of Helsinki, Helsinki, Finland, 115 pp., 2002.

Vega-Gonzalez, "Upper Limb Activity Monitoring," Arch Phys Med Rehabil, vol. 86, pp. 541-548, Mar. 2005.

Velten et al., "A New Three-Axis Accelerometer," Sensor '99—$9^{th}$ Int'l Traide Fair and Conference for Sensors/Transducers & Systems, Nürnberg, Germany, May 18-20, 1999, Sensor '99 Proceedings II, A 5.2, pp. 47-52, 1999.

PCT/US09/49991: International Search Report and Written Opinion dated Oct. 5, 2009, 15 pp.

U.S. Appl. No. 12/815,834, filed Jun. 15, 2010, Gerber et al.
U.S. Appl. No. 12/433,750, filed Apr. 30, 2009, Skelton et al.
U.S. Appl. No. 12/433,103, filed Apr. 30, 2009, Skelton et al.
U.S. Appl. No. 12/433,632, filed Apr. 30, 2009, Skelton et al.
U.S. Appl. No. 12/433,558, filed Apr. 30, 2009, Skelton et al.
U.S. Appl. No. 12/433,623, filed Apr. 30, 2009, Skelton et al.
U.S. Appl. No. 12/433,854, filed Apr. 30, 2009, Skelton et al.
U.S. Appl. No. 12/433,749, filed Apr. 30, 2009, Skelton et al.
U.S. Appl. No. 12/433,855, filed Apr. 30, 2009, Skelton et al.
U.S. Appl. No. 12/433,501, filed Apr. 30, 2009, Skelton et al.
U.S. Appl. No. 12/433,520, filed Apr. 30, 2009, Skelton.
U.S. Appl. No. 12/433,551, filed Apr. 30, 2009, Davis et al.
U.S. Appl. No. 12/433,588, filed Apr. 30, 2009, Skelton et al.
U.S. Appl. No. 12/433,599, filed Apr. 30, 2009, Skelton et al.
U.S. Appl. No. 12/433,442, filed Apr. 30, 2009, Skelton et al.
U.S. Appl. No. 12/433,756, filed Apr. 30, 2009, Panken et al.
U.S. Appl. No. 12/433,808, filed Apr. 30, 2009, Skelton et al.
U.S. Appl. No. 12/433,725, filed Apr. 30, 2009, Skelton et al.
U.S. Appl. No. 12/433,530, filed Apr. 30, 2009, Skelton et al.
U.S. Appl. No. 12/433,325, filed Apr. 30, 2009, Skelton et al.
U.S. Appl. No. 12/433,373, filed Apr. 30, 2009, Skelton et al.
U.S. Appl. No. 12/433,651, filed Apr. 30, 2009, Skelton et al.
U.S. Appl. No. 12/433,673, filed Apr. 30, 2009, Skelton et al.
U.S. Appl. No. 12/433,785, filed Apr. 30, 2009, Davis et al.
U.S. Appl. No. 12/433,827, filed Apr. 30, 2009, Skelton et al.
U.S. Appl. No. 12/433,848, filed Apr. 30, 2009, Skelton et al.
U.S. Appl. No. 12/433,840, filed Apr. 30, 2009, Skelton et al.
U.S. Appl. No. 12/433,839, filed Apr. 30, 2009, Skelton et al.
U.S. Appl. No. 12/433,803, filed Apr. 30, 2009, Skelton et al.
U.S. Appl. No. 12/433,815, filed Apr. 30, 2009, Skelton et al.
U.S. Appl. No. 12/433,684, filed Apr. 30, 2009, Skelton et al.
U.S. Appl. No. 12/771,854, filed Apr. 30, 2010, Skelton.
U.S. Appl. No. 12/433,017, filed Apr. 30, 2009, Skelton et al.
U.S. Appl. No. 12/433,004, filed Apr. 30, 2009, Panken et al.
U.S. Appl. No. 12/548,227, filed Aug. 26, 2009, Skelton et al.
U.S. Appl. No. 12/433,038, filed Apr. 30, 2009, Panken.
U.S. Appl. No. 12/433,029, filed Apr. 30, 2009, Panken et al.
U.S. Appl. No. 12/432,993, filed Apr. 30, 2010, Panken et al.
U.S. Appl. No. 12/769,461, filed Apr. 28, 2010, Sahasrabudhe et al.
U.S. Appl. No. 12/769,391, filed Apr. 28, 2010, Sahasrabudhe et al.
U.S. Appl. No. 12/769,484, filed Apr. 28, 2010, Panken et al.

* cited by examiner

MODIFICATION PROFILES FOR
POSTURE-RESPONSIVE THERAPY

This application claims the benefit of U.S. Provisional Application No. 61/080,070, entitled, "MODIFICATION PROFILES FOR POSTURE-RESPONSIVE THERAPY," and filed on Jul. 11, 2008, the entire content of which is incorporated herein by reference.

TECHNICAL FIELD

The disclosure relates to medical devices and, more particularly, to programmable medical devices that deliver therapy.

BACKGROUND

A variety of medical devices are used for chronic, e.g., long-term, delivery of therapy to patients suffering from a variety of conditions, such as chronic pain, tremor, Parkinson's disease, epilepsy, urinary or fecal incontinence, sexual dysfunction, obesity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician.

In some cases, the patient may be allowed to activate and/or modify the therapy delivered by the medical device. For example, a patient can be provided with a patient programming device. The patient programming device communicates with a medical device to allow the patient to activate therapy and/or adjust therapy parameters. For example, an implantable medical device (IMD), such as an implantable neurostimulator, may be accompanied by an external patient programmer that permits the patient to activate and deactivate neurostimulation therapy and/or adjust the intensity of the delivered neurostimulation. The patient programmer may communicate with the IMD via wireless telemetry to control the IMD and/or retrieve information from the IMD.

SUMMARY

In general, the disclosure describes techniques for modifying therapy provided to a patient by a medical device. The techniques are applicable to electrical stimulation therapy or other therapies. In some examples, modification of therapy includes adjustment of one or more therapy parameter values that define one or more characteristics of therapy delivered to a patient. In some examples, the therapy modification is based on activity of a patient that is detected by an IMD, such as a change in a detected posture state occupied by the patient.

Different therapy modifications may be applied for different changes in detected posture state. For example, an IMD may modify therapy based on a detected transition from one posture state to another posture state, and apply different modifications for different transitions. In some aspects, the modification includes a profile, such as a ramp up or ramp down in a parameter value over a period of time. The profile may be different for different posture transitions. A ramp slope may be steeper for one transition than for another transition. When a patient transitions from an upright to a lying posture state, for example, the profile may be especially abrupt compared to when the patient transitions between lying posture states or from a lying posture state to an upright posture state.

In one example, the disclosure relates to a method comprising delivering therapy to a patient from a medical device and modifying the therapy according to a modification profile in response to a posture state transition of the patient, wherein the modification profile varies according to a type of the posture state transition.

In another example, the disclosure relates to a therapy system comprising a therapy delivery module configured to deliver therapy to a patient; a posture state module configured to detect a posture state transition of the patient; and a processor configured to modify the therapy according to a modification profile in response to the posture state transition, wherein the modification profile varies according to a type of the posture state transition.

In another example, the disclosure relates to a computer-readable storage medium comprising instructions for causing one or more processors to perform a method, the method comprising controlling a medical device to deliver therapy to a patient and modifying the therapy according to a modification profile in response to a posture state transition of the patient, wherein the modification profile varies according to a type of the posture state transition.

In another example, the disclosure relates to a therapy system comprising means for delivering therapy to a patient and means for modifying the therapy according to a modification profile in response to a posture state transition of the patient, wherein the modification profile varies according to a type of the posture state transition.

In another example, the disclosure is directed to a method comprising delivering therapy to a patient from a medical device; detecting a posture state transition of the patient; selecting a modification profile based on the posture state transition; and modifying the therapy according to the modification profile based on the detection of the posture state transition.

In another example, the disclosure is directed to a therapy system comprising a therapy delivery module configured to deliver therapy to a patient from a medical device; a posture state module configured to detect a posture state transition of the patient; and a processor configured to select a modification profile based on the detection of the posture state transition and modify the therapy according to the modification profile based on the detection of the posture state transition.

In another example, the disclosure is directed to a therapy system comprising means for delivering therapy to a patient; means for detecting a posture state transition of the patient; means for selecting a modification profile based on the posture state transition; and means for modifying the therapy according to the modification profile based on the detection of the posture state transition.

In another example, the disclosure is directed to a computer-readable medium comprising instructions. The instructions cause a programmable processor to perform any of the techniques described herein. The instructions may be encoded in the computer-readable medium.

The details of one or more examples of systems, devices, and techniques are set forth in the accompanying drawings and the description below. Other features, objects, and advantages of the disclosure will be apparent from the description and drawings, and from the claims.

DETAILED DESCRIPTION

Figure 1A:
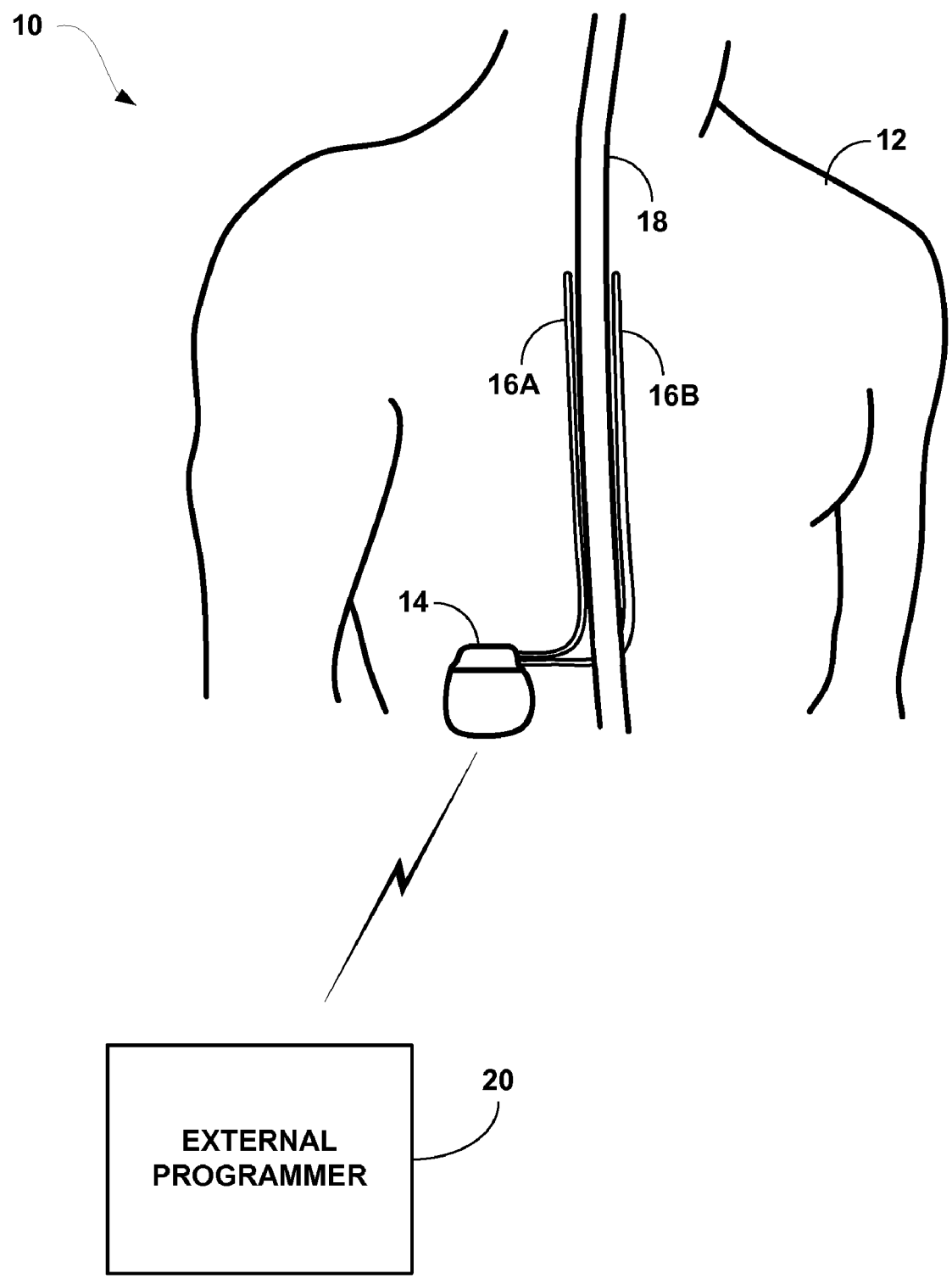
FIG. 1A is a conceptual diagram illustrating an example implantable stimulation system including two implantable stimulation leads.

In some medical devices that deliver electrical stimulation therapy, therapeutic efficacy may change as the patient changes posture states. In general, a posture state may refer to a patient posture or a combination of posture and activity. For example, some posture states, such as upright, may be subcategorized as upright and active or upright and inactive. Other posture states, such as lying down posture states, may or may not have an activity component. Efficacy may refer, in general, to a combination of complete or partial alleviation of symptoms alone, or in combination with a degree of undesirable side effects.

Changes in posture state may cause changes in efficacy due to changes in distances between electrodes or other therapy delivery elements, e.g., due to temporary migration of leads or catheters caused by forces or stresses associated with different postures, or from changes in compression of patient tissue in different posture states. Also, posture state changes may present changes in symptoms or symptom levels, e.g., pain level. To maintain therapeutic efficacy, it may be desirable to adjust therapy parameters based on different postures and/or activities engaged by the patient. A therapy system may adjust therapy by modifying values for one or more specific therapy parameters, e.g., by specifying adjustments to a specific therapy parameter or by selecting different therapy programs or groups of programs that define different sets of therapy parameter values. A therapy program may define respective values for a set of therapy parameters.

A change in efficacy due to changes in posture state may require the patient to continually manage therapy by manually adjusting certain therapy parameters, such as amplitude, pulse rate, or pulse width, or selecting different therapy programs to achieve more efficacious therapy throughout many different posture states. In some cases, a medical device employs a posture state detector that detects the patient posture state. The medical device adjusts therapy parameters in response to different posture states, which are determined with the posture state detector. Therapy adjustments in response to different posture states may be fully automatic, semi-automatic in the sense that a user may provide approval of proposed changes, or user-directed in the sense that the patient may manually adjust therapy based on the posture state indication.

In general, the disclosure describes techniques for modifying therapy provided to a patient by a medical device. The techniques are applicable to electrical stimulation therapy or other therapies, such as therapeutic agent delivery therapy. Modification of therapy may include adjustment of one or more therapy parameter values that define one or more characteristics of stimulation therapy delivered to a patient. The therapy modification may be based on activity of a patient that is detected by an implantable medical device (IMD), such as a change in a detected posture state occupied by the patient.

Different therapy modifications may be applied for different changes in detected posture state. An IMD may modify one or more therapy parameter values based on a transition from one posture state to another posture state, and apply different types of modifications for different transitions. In some aspects, the modification may include a profile, such as a ramp up or ramp down in a parameter value over a period of time. The profile may be different for different posture transitions. A ramp slope may be steeper for one transition than for another transition. When a patient transitions from an upright to a lying posture state, for example, the profile may be especially abrupt.

The posture-based therapy modification techniques described in this disclosure are generally described in terms of application to electrical stimulation therapies for purposes of illustration. However, such techniques may be applied to other types of therapies, such as therapeutic fluid delivery. Therapy parameter values associated with electrical stimulation may include voltage or current amplitude, electrode configuration, and frequency. In the case of electrical stimulation pulses, therapy parameter values may include voltage or current pulse amplitude, pulse rate, pulse width and electrode configuration. Electrode configuration generally refers to a combination of electrodes and electrode polarities used to deliver stimulation.

Stimulation therapy delivered to a patient may be modified for any of a variety of reasons. In some cases, symptoms such as pain intensity change based on the posture state of the patient. For example, a patient may experience a greater degree of pain while walking compared to standing, while standing compared to sitting, or while sitting compared to a lying posture state. In such cases, it may be desirable to adjust one or more therapy parameter values in order to maintain therapeutic efficacy across multiple posture states. If pain is more intense in a given posture state, for example, stimulation amplitude may be increased to provide more effective pain relief. Posture state changes, in addition to presenting changes in symptoms, may cause implanted therapy elements such as leads and electrodes to migrate relative to one another or relative to a target tissue site.

For example, compression, expansion, or other changes to tissue may render therapy more or less intense due to lead or catheter migration. As an illustration, for spinal cord stimulation (SCS), when a patient transitions from an upright posture state to a lying posture state in which the patient is lying on his back, leads may be compressed inward toward the spinal cord, possibly resulting in an acute increase in stimulation intensity.

To maintain therapeutic efficacy, the stimulation therapy delivered to a patient may be posture-responsive in the sense that one or more therapy parameter values may be modified when a patient transitions between different posture states. For example, an implantable electrical stimulation system may be configured to detect a posture state of a patient and automatically modify stimulation therapy based on the detected posture state.

As a result of the posture-responsive therapy delivery, the values of one or more stimulation parameters of a stimulation signal being delivered as part of a therapy may change over time, e.g., according to a patient's posture state sensed by an implantable stimulation system. As an example, a patient may experience more pain while walking compared to standing. In such cases, an IMD may be configured to automatically modify the stimulation therapy to a relatively higher stimulation intensity when it detects that the patient has transitioned from standing to walking, e.g., by delivering therapy having a higher stimulation amplitude value when the patient is walking compared to the stimulation amplitude value when the patient is standing, to address the increased pain experienced by the patient.

As a further example, an IMD may be configured to automatically modify the stimulation therapy to a lower stimulation intensity when the stimulation system detects that the patient has ceased walking and returned to a standing posture state. In this manner, stimulation therapy delivered to a patient via an IMD may be automatically modified to deliver stimulation appropriate to the posture state exhibited by a patient.

Therapy may be modified according to a modification profile. The profile of the modification may refer to any of a variety of characteristics of the modification, such as timing (e.g., dwell time), slope, or the like. For some posture state transitions, for example, the modification profile is characterized by a gradual slope in the therapy parameter value over an extended period of time. For other posture state transitions, the modification profile is characterized by an abrupt increase or decrease in a therapy parameter value. In this case, the therapy parameter value may be more immediately (e.g., instantaneously) modified, rather than gradually ramped upward or downward.

An immediate change in the therapy parameter value can be characterized by, for example, a jump from therapy delivery according to a first therapy parameter value to therapy delivery according to a second therapy parameter value. In contrast, a gradual change in the therapy parameter value can be accomplished by, for example, shifting from the therapy parameter value to a second therapy parameter value over time. The shift from the first therapy parameter value to the second therapy parameter value can involve, for example, therapy delivery according to intermediate therapy parameter values between the first and second therapy parameter values. In other examples, the therapy parameter value may be ramped from an existing therapy parameter value to a desired parameter value rather than ramping the existing parameter value down to approximately zero and then ramping up from zero to the new stimulation parameter, e.g., as an immediate change in the therapy. For example, in the case of an adjustment in which the desired parameter value is higher than the existing parameter value of the stimulation being delivered, an IMD may increase the parameter value by ramping up to the desired value according to a constant rate of change during a transition period.

When therapy delivery to the patient is gradually changed, the modification profile can define the amount of time required for the parameter to be increased from the existing parameter value to the desired parameter value at the defined rate of change. This parameter of the modification profile may be referred to as a transition time. By gradually ramping a stimulation parameter to a desired value over time rather than making an adjustment to a desired value substantially immediately, an IMD may effectively adjust the stimulation parameter based on patient posture state without the patient experiencing undesirable side effects that may result from making abrupt changes to a stimulation parameter, such as stimulation amplitude, too quickly.

In some examples, an IMD may make an adjustment to a stimulation parameter at different rates of change, i.e., different ramps, depending on one or more properties relating to the adjustment. As one example, the specific rate of change with which an IMD adjusts a stimulation parameter may correspond to a particular posture state transition that resulted in the parameter adjustment. As another example, the specific rate of change with which an IMD adjusts a stimulation parameter may correspond to the nature or type of parameter adjustment, e.g., an increase or decrease. In this manner, not only may the stimulation therapy delivered to a patient be modified based on particular posture state transitions but also particular types of modifications in therapy parameter values.

In addition, in some circumstances, an abrupt modification profile may be desirable, such as when a patient transitions from an upright posture state to a lying down (back) posture state. In this case, it may be desirable to reduce stimulation amplitude to reduce stimulation intensity in the event tissue compression places the electrodes closer to the target tissue. Moreover, it may be desirable to reduce stimulation amplitude abruptly rather than by a gradual ramp in order to reduce the likelihood that the patient will experience discomfort due to transfer of a greater effective amount of stimulation energy upon tissue compression.

Hence, the disclosure describes a variety of techniques for posture-responsive therapy modification that make use of different modification profiles for different posture state transitions. By applying different modification profiles for different posture state transitions, such techniques may support consistent therapeutic efficacy as a patient transitions between different posture states.

FIG. 1A is a schematic diagram illustrating an implantable stimulation system 10 including a pair of implantable electrode arrays in the form of stimulation leads 16A and 16B. Although the techniques described in this disclosure are generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable SCS system for purposes of illustration, but without limitation as to other types of medical devices.

As shown in FIG. 1A, system 10 includes an IMD 14 and external programmer 20 shown in conjunction with a patient 12, who is ordinarily a human patient. In the example of FIG. 1A, IMD 14 is an implantable electrical stimulator that delivers SCS, e.g., for relief of chronic pain or other symptoms. Again, although FIG. 1A shows an IMD, other examples may include an external stimulator, e.g., with percutaneously implanted leads. Stimulation energy is delivered from IMD 14 to spinal cord 18 of patient 12 via one or more electrodes of implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1A is directed to SCS therapy, system 10 may alternatively be directed to any other condition that may benefit from stimulation therapy. For example, system 10 may be used to treat tremor, Parkinson's disease, epilepsy, urinary or fecal incontinence, sexual dysfunction, obesity, gastroparesis, or psychiatric disorders (e.g., depression, mania, obsessive compulsive disorder, anxiety disorders, and the like). In this manner, system 10 may be configured to provide therapy taking the form of deep brain stimulation (DBS), pelvic floor stimulation, gastric stimulation, or any other stimulation therapy.

Each of leads 16 may include electrodes (not shown in FIG. 1), and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms, such as continuous waveforms. Programs that control delivery of other therapies by IMD 12 may include other parameters, e.g., such as dosage amount, rate, or the like for drug delivery.

In the example of FIG. 1A, leads 16 carry one or more electrodes that are placed adjacent to the target tissue of the spinal cord. One or more electrodes may be disposed at a distal tip of a lead 16 and/or at other positions at intermediate points along the lead. Electrodes of leads 16 transfer electrical stimulation generated by IMD 14 to tissue of patient 12. The electrodes may be electrode pads on a paddle lead, circular (e.g., ring) electrodes surrounding the body of leads 16, conformable electrodes, cuff electrodes, segmented electrodes, or any other type of electrodes capable of forming unipolar, bipolar or multipolar electrode configurations for therapy. In general, ring electrodes arranged at different axial positions at the distal ends of leads 16 will be described for purposes of illustration.

Leads 16 may be implanted within patient 12 and directly or indirectly (e.g., via a lead extension) coupled to IMD 14. Alternatively, as mentioned above, leads 16 may be implanted and coupled to an external stimulator, e.g., through a percutaneous port. In some cases, an external stimulator is a trial or screening stimulation that used on a temporary basis to evaluate potential efficacy to aid in consideration of chronic implantation for a patient. In additional examples, IMD 14 may be a leadless stimulator with one or more arrays of electrodes arranged on a housing of the stimulator rather than leads that extend from the housing.

IMD 14 delivers electrical stimulation therapy to patient 12 via selected combinations of electrodes carried by one or both of leads 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1A, the target tissue is tissue proximate spinal cord 18, such as within an intrathecal space or epidural space of spinal cord 18, or, in some examples, adjacent nerves that branch off of spinal cord 18. Leads 16 may be introduced into spinal cord 18 in via any suitable region, such as the thoracic, cervical or lumbar regions. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns). Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

In the example of FIG. 1A, stimulation energy is delivered by IMD 14 to the spinal cord 18 to reduce the amount of pain perceived by patient 12. As described above, IMD 14 may be used with a variety of different therapies, such as peripheral nerve stimulation (PNS), peripheral nerve field stimulation (PNFS), DBS, cortical stimulation (CS), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate in the case of stimulation pulses.

In some examples, IMD 14 generates and delivers stimulation therapy according to one or more programs. A program defines values for one or more parameters that define an aspect of the therapy delivered by IMD 14 according to that program. For example, a program that controls delivery of stimulation by IMD 14 in the form of pulses may define a voltage or current pulse amplitude, a pulse width, a pulse rate, for stimulation pulses delivered by IMD 14 according to that program. Moreover, therapy may be delivered according to multiple programs, wherein multiple programs are contained within each of a plurality of groups.

Each program group may support an alternative therapy selectable by patient 12, and IMD 14 may deliver therapy according to the multiple programs. IMD 14 may rotate through the multiple programs of the group when delivering stimulation such that numerous conditions of patient 12 are treated. As an illustration, in some cases, stimulation pulses formulated according to parameters defined by different programs may be delivered on a time-interleaved basis. For example, a group may include a program directed to leg pain, a program directed to lower back pain, and a program directed to abdomen pain. In this manner, IMD 14 may treat different symptoms substantially simultaneously.

During use of IMD 14 to treat patient 12, movement of patient 12 among different posture states may affect the ability of IMD 14 to deliver consistent efficacious therapy. For example, posture state changes may present changes in symptoms or symptom levels, e.g., pain level. As another example, a patient posture state may affect the relative location between the electrodes of leads 16 and a target therapy site. For example, leads 16 may migrate toward IMD 14 when patient 12 bends at the waist, resulting in displacement of electrodes relative to the target stimulation site and possible disruption in delivery of effective therapy. Stimulation energy transferred to target tissue may be reduced due to electrode migration, which may reduce therapeutic efficacy in terms of relief of symptoms (e.g., pain) or an increase in undesirable side effects.

As another example of how posture state may affect the relative location between the electrodes of leads 16 and a target therapy site, leads 16 may be compressed towards spinal cord 18 when patient 12 lies down. Such compression may cause an increase in the amount of stimulation energy transferred to the target tissue. An increase in stimulation energy transferred to the target stimulation site may cause unusual sensations or an otherwise undesirable intensity of therapy, which may be both considered undesirable side effects that undermine overall efficacy. Thus, in some examples, the amplitude of stimulation therapy may need to be decreased when patient 12 is lying down to avoid causing patient 12 additional pain or unusual sensations resulting from the increased compression near electrodes of leads 16. The additional pain or unusual sensations may be considered undesirable side effects that undermine overall efficacy.

IMD 14 includes a posture state module that detects the patient posture state. The IMD automatically adjusts stimulation according to the detected posture state. The patient posture and activity level can, but need not include an activity component. Example posture states may include "Upright," "Upright and Active," "Lying Down," and so forth. IMD 14 includes a posture responsive therapy mode that, when activated, results in adjustment of one or more stimulation parameter values based on a detected posture state. The posture responsive therapy may help mitigate changes in the efficacy of therapy attributable to patient posture changes. For example, the posture state module may include one or more accelerometers (e.g., one or more single axis, two-axis or three-axis accelerometers) that detect when patient 12 occupies a posture state for which it is appropriate to decrease the stimulation amplitude, e.g., when patient 12 lies down. IMD 14 may automatically reduce stimulation amplitude upon detecting patient 12 is lying down, thereby eliminating the need for patient 12 to manually adjust the therapy, which may be cumbersome. In addition, automatic adjustment of stimulation parameters based on a detected patient posture may also provide more responsive therapy because IMD 14 may detect a change in patient posture and modify therapy parameters faster than patient 12 may be able to manually modify the therapy parameter values.

As will be described in greater detail below, in some examples, IMD 14 is configured to automatically decrease stimulation amplitude when it detects that patient 12 has changed posture states to a lying state. The amplitude adjustment may be configured to be decreased at a rate suitable to prevent undesirable effects, e.g., such as the effects due to the compression of leads 16 towards spinal cord 18 when patient lies down. In some examples, IMD 14 is configured to decrease the stimulation amplitude to a suitable amplitude value substantially immediately upon detection by IMD 14 that patient 12 is lying down. In other examples, the stimulation amplitude is not decreased substantially immediately by IMD 14 upon detection of patient 12 lying down, but instead IMD 14 decreases the stimulation amplitude to a suitable amplitude level at a rate of change that is suitable to prevent patient 12 from experiencing undesirable stimulation effects, e.g., due to increased transfer of stimulation energy to tissue of patient 12. In some examples, IMD 14 substantially instantaneously decreases the stimulation amplitude to a suitable amplitude value when IMD detects that patient 12 is lying down.

Many other examples of reduced efficacy due to increase coupling or decreased coupling of stimulation energy to target tissue may occur due to changes in posture and/or activity level associated with patient posture state. To avoid or reduce possible disruptions in effective therapy due to posture state changes, IMD 14 includes a posture state module that detects the posture state of patient 12 and causes the IMD 14 to automatically adjust stimulation according to the detected posture state. For example, a posture state module may include a posture state sensor such as an accelerometer that detects when patient 12 lies down, stands up, or otherwise changes posture.

In response to a posture state indication by the posture state module, IMD 14 may change program group, program, stimulation amplitude, pulse width, pulse rate, and/or one or more other parameters, groups or programs to maintain therapeutic efficacy. When patient 12 lies down, for example, IMD 14 may automatically reduce stimulation amplitude so that patient 12 does not need to reduce stimulation amplitude manually. In some cases, IMD 14 may communicate with external programmer 20 to present a proposed change in stimulation in response to a posture state change, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

Referring still to FIG. 1A, a user, such as a clinician or patient 12, may interact with a user interface of external programmer 20 to program IMD 14. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy modifications relating to changes in the posture state of patient 12. As another example, a user may select programs or program groups. Again, a program may be characterized by an electrode combination, electrode polarities, voltage or current amplitude, pulse width, pulse rate, and/or duration. A group may be characterized by multiple programs that are delivered simultaneously or on an interleaved or rotating basis.

In some cases, external programmer 20 may be characterized as a physician or clinician programmer if it is primarily intended for use by a physician or clinician. In other cases, external programmer 20 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

Figure 1B:
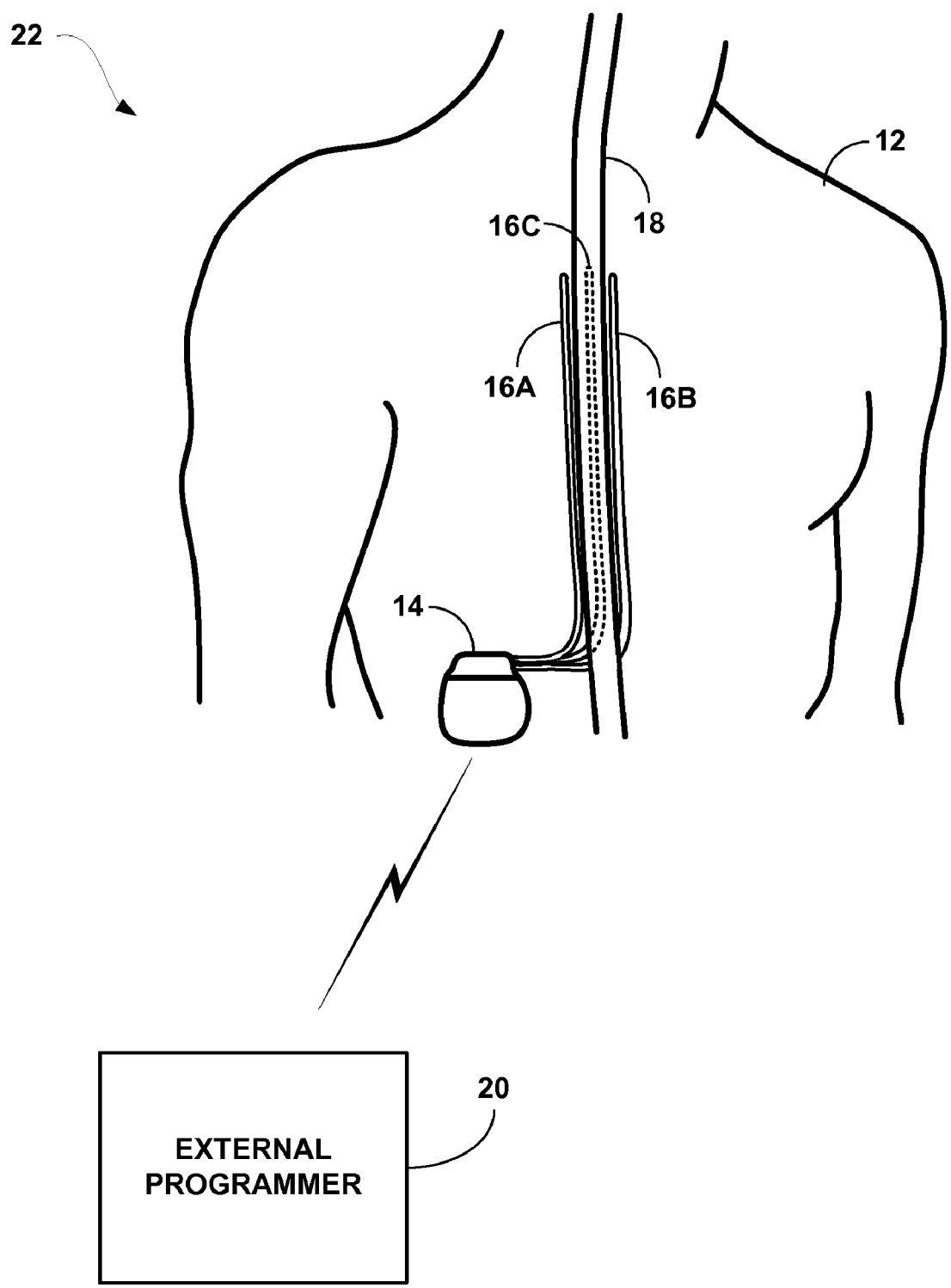
FIG. 1B is a conceptual diagram illustrating an example implantable stimulation system including three implantable stimulation leads.

FIG. 1B is a conceptual diagram illustrating an implantable stimulation system 22 including three implantable stimulation leads 16A, 16B, 16C (collectively leads 16). System 22 generally conforms to system 10 of FIG. 1A, but includes a third lead. Accordingly, IMD 14 may deliver stimulation via combinations of electrodes carried by all three leads 16, or a subset of the three leads. The third lead, e.g., lead 16C, may include a greater number of electrodes than leads 16A and 16B and be positioned between leads 16A and 16B or on one side of either lead 16A or 16B. The number and configuration of leads 16 may be stored within external programmer 20 to allow programmer 20 to appropriately program stimulation therapy or assist in the programming of stimulation therapy.

In some examples, leads 16A and 16B each include four electrodes, while lead 16C includes eight or sixteen electrodes, thereby forming a so-called 4-8-4 or 4-16-4 lead configuration. Other lead configurations, such as 8-16-8, 8-4-8, 16-8-16, 16-4-16, are possible, whereby the number in the configuration indication refers to the number of electrodes in a particular electrode column, which may be defined by a lead 16A-16C. In some cases, electrodes on lead 16C may be smaller in size and/or closer together than the electrodes of leads 16A or 16B. Movement of lead 16C due to changing activities or postures of patient 12 may, in some instances, more severely affect stimulation efficacy than movement of leads 16A or 16B. Patient 12 may further benefit from the ability of IMD 14 to detect posture states and associated changes and automatically adjust stimulation therapy to maintain therapy efficacy in a three lead system 22.

Figure 1C:
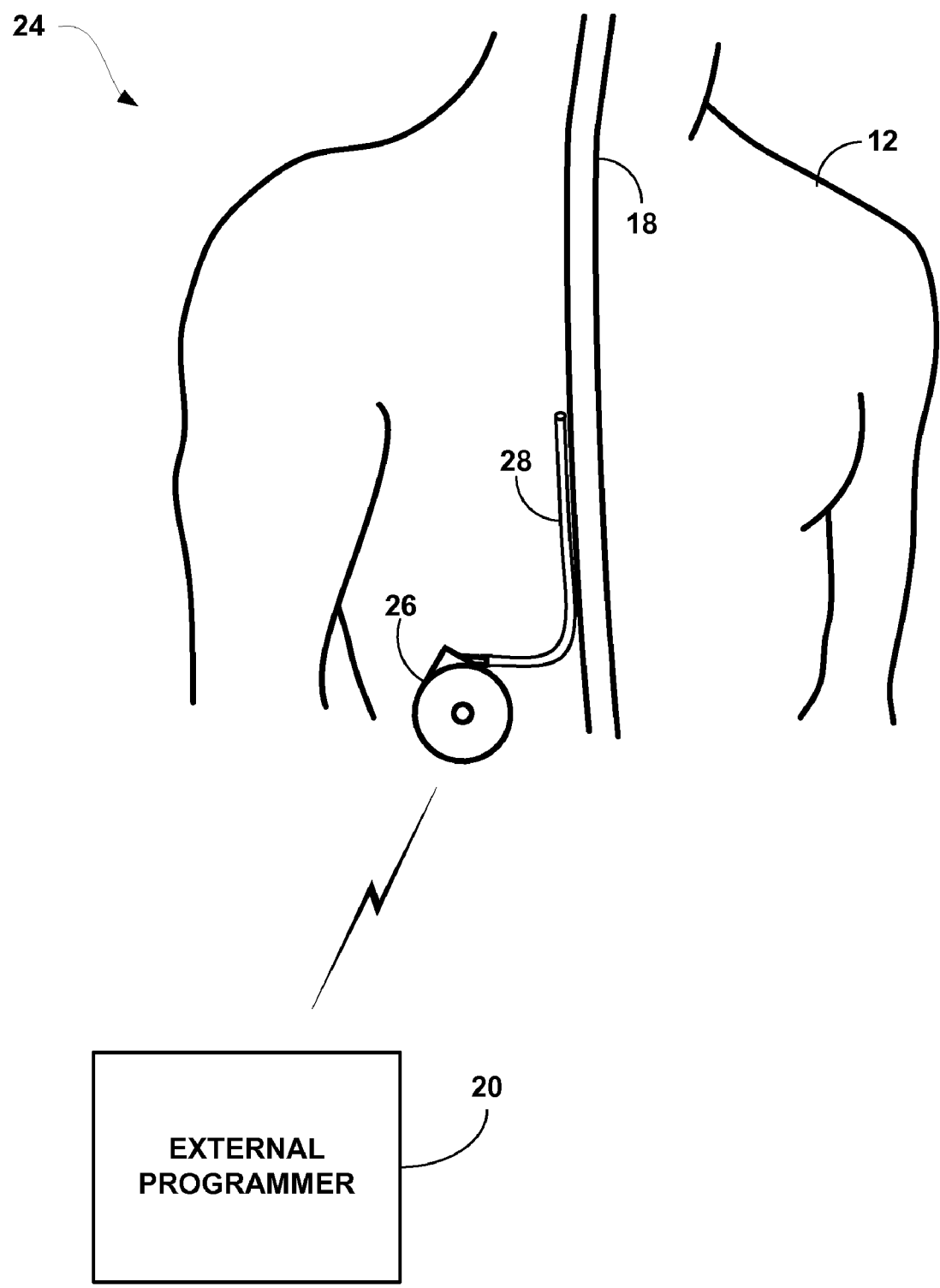
FIG. 1C is a conceptual diagram illustrating an example implantable drug delivery system including a delivery catheter.

FIG. 1C is a conceptual diagram illustrating an implantable drug delivery system 24 including one delivery catheter 28 coupled to IMD 26. As shown in the example of FIG. 1C, drug delivery system 24 is substantially similar to systems 10 and 22. However, drug delivery system 24 performs the similar therapy functions via delivery of one or more therapeutic agents instead of electrical stimulation therapy. IMD 26 functions as a drug pump in the example of FIG. 1C, and IMD 26 communicates with external programmer 20 to initialize therapy or modify therapy during operation. In addition, IMD 26 may be refillable to allow chronic drug delivery.

A fluid delivery port of catheter 28 may be positioned within an intrathecal space or epidural space of spinal cord 18, or, in some examples, adjacent nerves that branch off of spinal cord 18. Although IMD 26 is shown as coupled to only one catheter 28 positioned along spinal cord 18, additional catheters may also be coupled to IMD 26. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. In some examples, IMD 26 may be an external device that includes a percutaneous catheter that to deliver a therapeutic agent to patient 12, e.g., in the same manner as catheter 28. Alternatively, the percutaneous catheter can be coupled to catheter 28, e.g., via a fluid coupler. In other examples, IMD 26 may include both electrical stimulation capabilities as described in IMD 14 (FIG. 1A) and drug delivery therapy.

IMD 26 may also operate using parameters that define the method of drug delivery. IMD 26 may include programs, or groups of programs, that define different delivery methods for patient 14. For example, a program that controls delivery of a drug or other therapeutic agent may include a titration rate or information controlling the timing of bolus deliveries. Patient 14 may use external programmer 20 to adjust the programs or groups of programs to regulate the therapy delivery.

Similar to IMD 14, IMD 26 includes a posture state module that monitors the patient 12 posture state and adjusts therapy accordingly. For example, the posture state module may indicate that patient 12 transitions from lying down to standing up. IMD 26 may automatically increase the rate of drug delivered to patient 12 in the standing position if patient 12 has indicated that pain increased when standing. This automated adjustment to therapy based upon posture state may be activated for all or only a portion of the programs used by IMD 26 to deliver therapy.

Similar to the examples described with respect to adjustment of one or more electrical stimulation parameters to modify electrical stimulation therapy during a transition period, based on patient's 12 detected posture state, one or more parameters associated with the drug delivery therapy provided by IMD 26 may be modified with different modification profiles. The modification profiles may be, for example, selected based on a type of detected patient posture transition. Different modification profiles may determine whether the parameter value is ramped, rather than immediately changed, to a desired value from the beginning value. In the case of ramping, different modification profiles may determine different ramp rates, slopes, timing (e.g., dwell time), or the like.

As an example, the rate of drug delivery to patient 12 may be increased to a desirable rate from a lesser rate based on a detected patient transition from lying down to standing up according to a ramp defined for such a posture transition. In particular, the drug delivery rate may be adjusted to the desired level by ramping up the rate of drug delivery at a constant rate of change. Such adjustments to the drug delivery rate parameter may be automatically made by IMD 26 to modify the drug delivery therapy provided to patient 12 based on the posture state detected by IMD 26.

The techniques described herein for modifying therapy delivery by IMD 14 (FIG. 1A), which provides electrical stimulation therapy, may also be implemented to modify therapy delivery by IMD 26 selected based on a type of detected patient posture transition.

Figure 2:
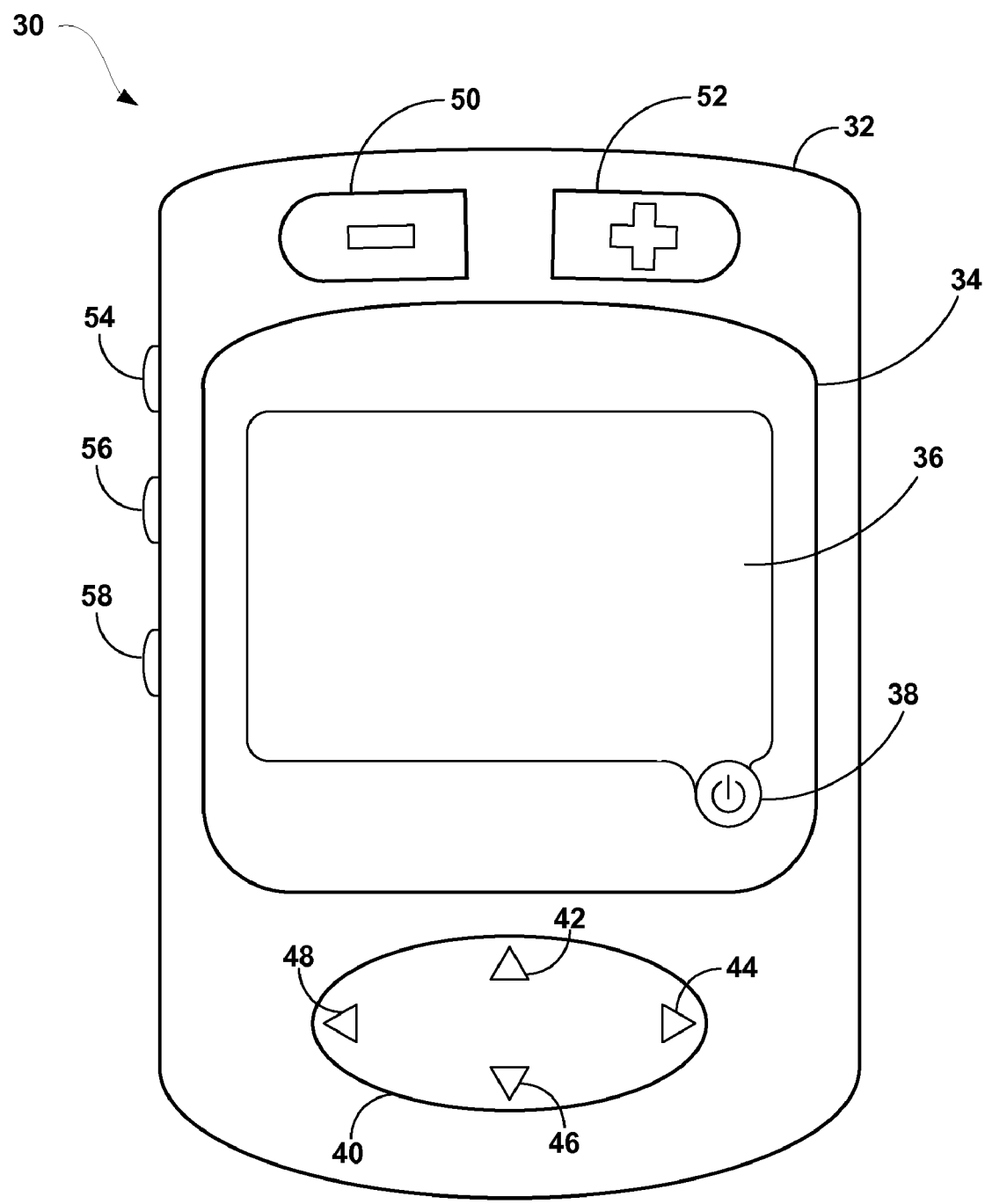
FIG. 2 is a conceptual diagram illustrating an example patient programmer for programming stimulation therapy delivered by an implantable medical device.

FIG. 2 is a conceptual diagram illustrating an example patient programmer 30 for programming stimulation therapy delivered by an IMD. Patient programmer 30 is an example of external programmer 20 illustrated in FIGS. 1A, 1B and 1C and may be used with either IMD 14 or IMD 26. In alternative examples, patient programmer 30 may be used with an external medical device. As shown in FIG. 2, patient programmer 30 provides a user interface (not shown) for a user, such as patient 12, to manage and program stimulation therapy. Patient programmer 30 is protected by housing 32, which encloses circuitry necessary for patient programmer 30 to operate.

Patient programmer 30 also includes display 36, power button 38, increase button 52, decrease button 50, sync button 58, stimulation ON button 54, and stimulation OFF button 56.

Cover 34 protects display 36 from being damaged during use of patient programmer 30. Patient programmer 30 also includes control pad 40 which allows a user to navigate through items displayed on display 36 in the direction of arrows 42, 44, 46, and 48. In some examples, the buttons and pad 40 may take the form of soft keys (e.g., with functions and contexts indicated on display 36), with functionality that may change, for example, based on current programming operation or user preference. In alternative examples, display 36 is a touch screen with which patient 12 may directly interact without the use of control pad 40. A touch screen display may eliminate the use of buttons, such as increase button 52 and decrease button 50, although buttons may be used in addition to a touch screen display.

In the illustrated example, patient programmer 30 is a hand held device. Patient programmer 30 may accompany patient 12 throughout a daily routine. In some cases, patient programmer 30 may be used by a clinician when patient 12 visits the clinician in a hospital or clinic. In other examples, patient programmer 30 may be a clinician programmer that remains with the clinician or in the clinic and is used by the clinician and/or patient 12 when the patient is in the clinic. In the case of a clinician programmer, small size and portability may be less important. Accordingly, a clinician programmer may be sized larger than a patient programmer, and it may provide a larger screen for more full-featured programming.

Housing 32 may be constructed of a polymer, metal alloy, composite, or combination material suitable to protect and contain components of patient programmer 30. In addition, housing 32 may be partially or completely sealed such that fluids, gases, or other elements may not penetrate the housing and affect components therein. Power button 38 may turn patient programmer 30 ON or OFF as desired by patient 12. Patient 12 may control the illumination level, or backlight level, of display 36 by using control pad 40 to navigate through the user interface and increase or decrease the illumination level with decrease and increase buttons 50 and 52.

In some examples, illumination may be controlled by a knob that rotates clockwise and counter-clockwise to control patient programmer 30 operational status and display 36 illumination. Patient programmer 30 may be prevented from turning OFF during telemetry with IMD 14 or another device to prevent the loss of transmitted data or the stalling of normal operation. Alternatively, patient programmer 30 and IMD 14 may include instructions that handle possible unplanned telemetry interruption, such as battery failure or inadvertent device shutdown.

Display 36 may include any one or more of a liquid crystal display (LCD), dot matrix display, organic light-emitting diode (OLED) display, touch screen, or similar monochrome or color display capable of providing visible information to patient 12. Display 36 may provide a user interface regarding current stimulation therapy, posture state information, provide a user interface for receiving feedback or medication input from patient 12, display an active group of stimulation programs, and display operational status of patient programmer 30 or IMDs 14 or 26. For example, patient programmer 30 may provide a scrollable list of groups, and a scrollable list of programs within each group, via display 36. In addition, display may present a visible posture state indication.

Patient 12 or another user may interact with control pad 40 to navigate through items displayed on display 36. Patient 12 may press control pad 40 on any of arrows 42, 44, 46, and 48 in order to move between items presented on display 36 or move to another screen not currently shown on the display. In some examples, pressing the middle of control pad 40 selects any items highlighted in display 36. In other examples, scroll bars, a scroll wheel, individual buttons, or a joystick may perform the complete or partial functions of control pad 40. In alternative examples, control pad 40 may be a touch pad that allows patient 12 to move a cursor within the user interface displayed on display 36 to manage therapy.

Decrease button 50 and increase button 52 provide an input mechanism for patient 12. In general, activation of decrease button 50 (e.g., by pressing button 50) decreases the value of a highlighted stimulation parameter every time the decrease button is pressed. In contrast, activation of increase button 52 increases the value of a highlighted stimulation parameter one step every time the increase button is pressed. While buttons 50 and 52 may be used to control the value of any stimulation parameter, buttons 50 and 52 may also control patient feedback input. When either button 50 or 52 is selected, patient programmer 30 may initialize communication with IMD 14 or 26 to change therapy accordingly.

When depressed by patient 12, stimulation ON button 54 directs programmer 30 to generate a command for communication to IMD 14, where the command instructs IMD 14 to turn on stimulation therapy. Stimulation OFF button 56 turns off stimulation therapy when depressed by patient 12. Sync button 58 forces patient programmer 30 to communicate with IMD 14. When patient 12 enters an automatic posture response screen of the user interface, pressing sync button 58 turns on the automatic posture response to allow IMD 14 to automatically change therapy according to the posture state of patient 12. Pressing sync button 58 again, when the automatic posture response screen is displayed, turns off the automatic posture response. In the example of FIG. 2, patient 12 may use control pad 40 to adjust the volume, contrast, illumination, time, and measurement units of patient programmer 30.

In some examples, buttons 54 and 56 may be configured to perform operational functions related to stimulation therapy or the use of patient programmer 30. For example, buttons 54 and 56 may control the volume of audible sounds produced by programmer 20, wherein button 54 increases the volume and button 56 decreases the volume. Button 58 may be pressed to enter an operational menu that allows patient 12 to configure the user interface of patient programmer 30 to the desires of patient 12. For example, patient 12 may be able to select a language, backlight delay time, display brightness and contrast, or other similar options. In alternative examples, buttons 50 and 52 may control all operational and selection functions, such as those related to audio volume or stimulation therapy.

Patient programmer 30 may take other shapes or sizes not described herein. For example, patient programmer 30 may take the form of a clam-shell shape, similar to some cellular phone designs. When patient programmer 30 is closed, some or all elements of the user interface may be protected within the programmer. When patient programmer 30 is opened, one side of the programmer may contain a display while the other side may contain input mechanisms. In any shape, patient programmer 30 may be capable of performing the requirements described herein. Alternative examples of patient programmer 30 may include other input mechanisms such as a keypad, microphone, camera lens, or any other media input that allows the user to interact with the user interface provided by patient programmer 30.

In alternative examples, the buttons of patient programmer 30 may perform different functions than the functions provided in FIG. 2 and/or may have a different arrangement. In addition, other examples of patient programmer 30 may include different button layouts or different numbers of buttons. For example, patient programmer 30 may even include a single touch screen that incorporates all user interface functionality with a limited set of buttons or no other buttons.

Figure 3:
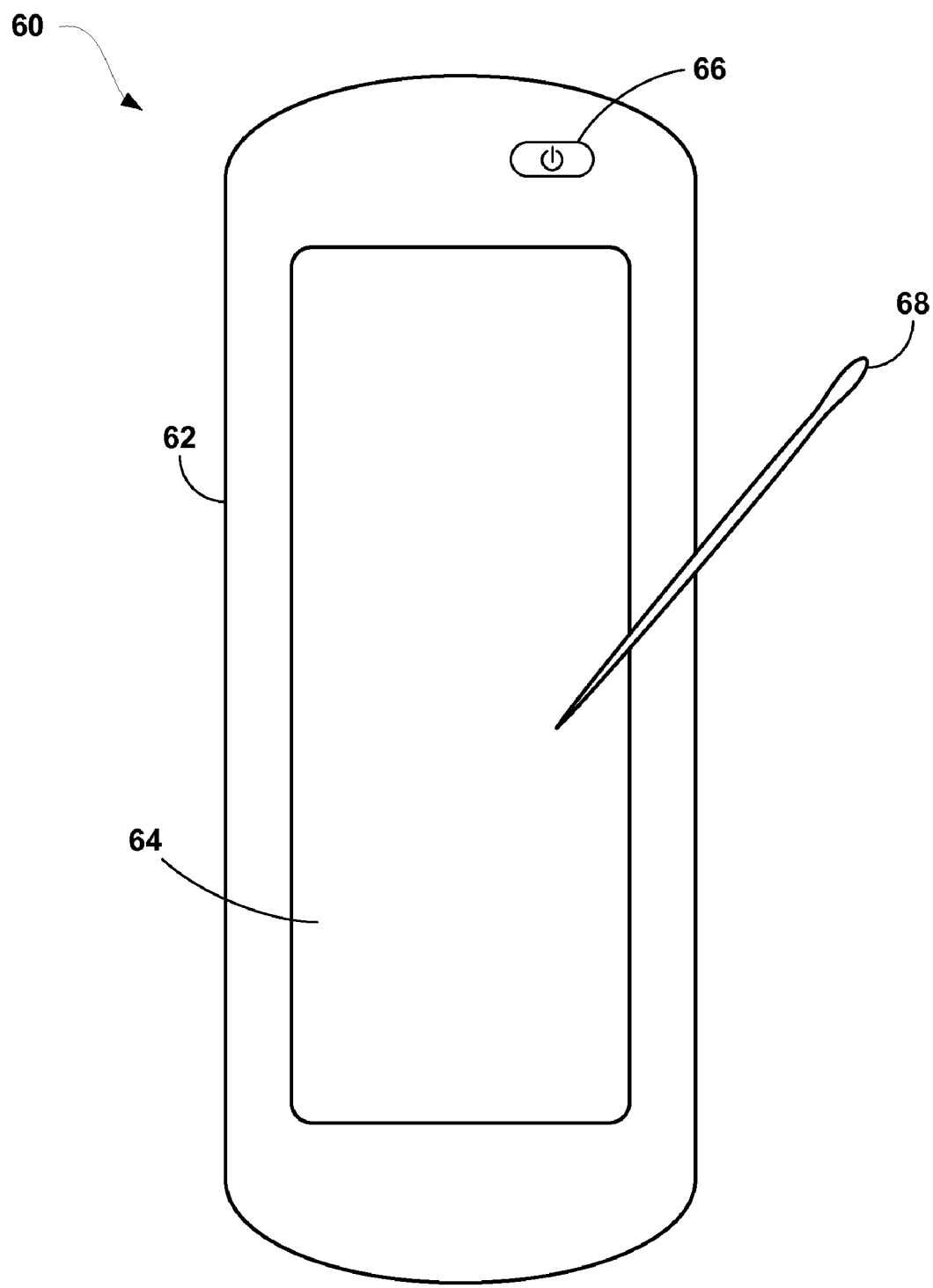
FIG. 3 is a conceptual diagram illustrating an example clinician programmer for programming stimulation therapy delivered by an implantable medical device.

FIG. 3 is a conceptual diagram illustrating an example clinician programmer 60 for programming stimulation therapy delivered by an IMD. Clinician programmer 60 is an example of external programmer 20 illustrated in FIGS. 1A, 1B and 1C and may be used with either IMD 14 or IMD 26. In alternative examples, clinician programmer 60 may be used with an external medical device. As shown in FIG. 3, clinician programmer 60 provides a user interface (not shown) for a user, such as a clinician, physician, technician, or nurse, to manage and program stimulation therapy. Clinician programmer 60 is protected by housing 62, which encloses circuitry necessary for clinician programmer 60 to operate.

Clinician programmer 60 includes display 64 and power button 66. In the example of FIG. 3, display 64 is a touch screen that accepts user input via touching certain areas within display 64. The user may use stylus 68 to touch display 64 and select virtual buttons, sliders, keypads, dials, or other such representations presented by the user interface shown by display 64. In some examples, the user may be able to touch display 64 with a finger, pen, or any other pointing device. In alternative examples, clinician programmer 60 may include one or more buttons, keypads, control pads, touch pads, or other devices that accept user input, similar to patient programmer 30.

In the illustrated example, clinician programmer 60 is a hand held device. Clinician programmer 60 may be used within the clinic or on in-house patient calls. Clinician programmer 60 may be used to communicate with multiple IMDs 14 and 26 within different patients. In this manner, clinician programmer 60 may be capable of communicating with many different devices and retain patient data separate for other patient data. In some examples, clinician programmer 60 may be a larger device that may be less portable, such as a notebook computer, workstation, or even a remote computer that communicates with IMD 14 or 26 via a remote telemetry device.

Most, if not all, of clinician programmer 60 functions may be completed via the touch screen of display 64. The user may program stimulation therapy (e.g., selecting stimulation parameter values), modify programs or groups, retrieve stored therapy data, retrieve posture state information from an IMD or another device, define posture states and other activity information, change the contrast and backlighting of display 64, or any other therapy related function. In addition, clinician programmer 60 may be capable of communicating with a networked server in order to send or receive an email or other message, retrieve programming instructions, access a help guide, send an error message, or perform any other function that may be beneficial to prompt therapy.

Housing 62 may be constructed of a polymer, metal alloy, composite, or combination material suitable to protect and contain components of clinician programmer 60. In addition, housing 62 may be partially or completely sealed such that fluids, gases, or other elements may not penetrate the housing and affect components therein. Power button 66 may turn clinician programmer 60 ON or OFF as desired by the user. Clinician programmer 60 may require a password, biometric input, or other security measure to be entered and accepted before the user can use clinician programmer 60.

Clinician programmer 60 may take other shapes or sizes not described herein. For example, clinician programmer 60 may take the form of a clam-shell shape, similar to some cellular phone designs. When clinician programmer 60 is closed, at least a portion of display 64 is protected within housing 62. When clinician programmer 60 is opened, one side of the programmer may contain a display while the other side may contain input mechanisms. In any shape, clinician programmer 60 may be capable of performing the requirements described herein.

Figure 4:
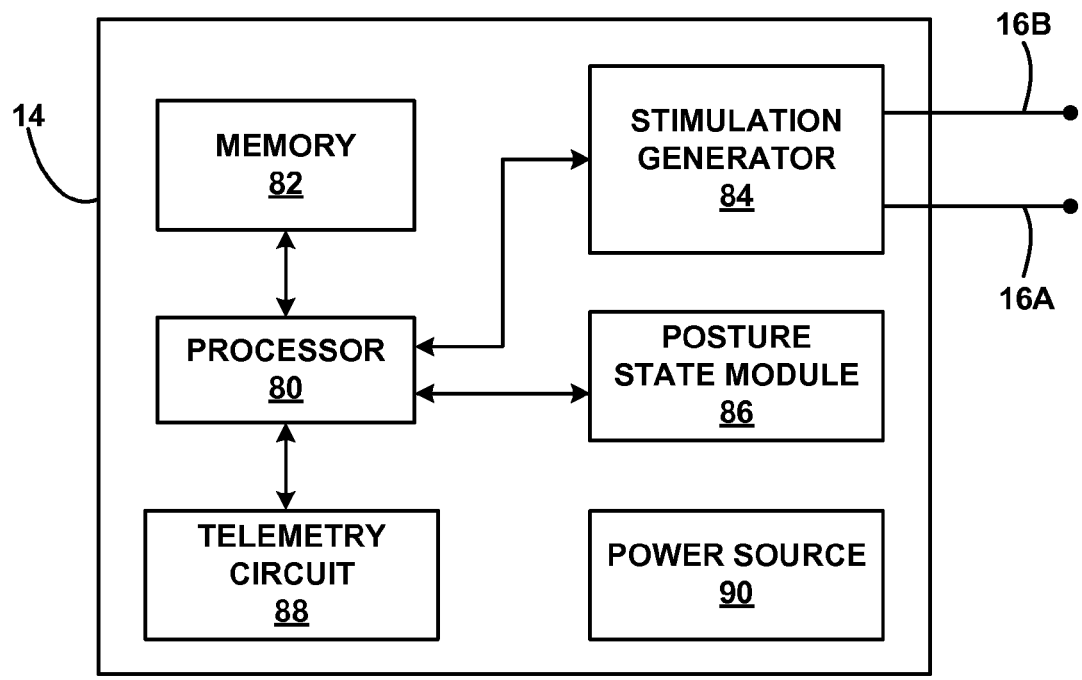
FIG. 4 is a functional block diagram illustrating various components of an example implantable electrical stimulator.

FIG. 4 is a functional block diagram illustrating various components of an IMD 14. In the example of FIG. 4, IMD 14 includes a processor 80, memory 82, stimulation generator 84, posture state module 86, telemetry circuit 88, and power source 90. The stimulation generator 84 forms a therapy delivery module.

Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 82 may store instructions for execution by processor 80, stimulation therapy data, posture state information (e.g., posture state definitions, information associating posture states with therapy programs, and the like), posture state indications, and any other information regarding therapy or patient 12. Therapy information may be recorded for long-term storage and retrieval by a user, and the therapy information may include any data created by or stored in IMD 14. Memory 82 may include separate memories for storing instructions, posture state information, program histories, and any other data that may benefit from separate physical memory modules.

As one example, memory 82 may store instructions for execution by processor 80 that define one or more properties of a ramp relating to parameter adjustments, e.g., such as a rate of parameter change during a transition period. Such instructions may allow for the modification of stimulation therapy delivered by IMD 14 based on a detected posture state by making adjustments to stimulation amplitude during a transition period, in which the parameter value is ramped at the specified rate of change. As another example, memory 82 may store instructions for execution by processor 80 that define a transition period over which stimulation generator 84 transitions from therapy delivery defined by a first program to therapy delivery defined by a different therapy program in response to a posture state transition.

Processor 80 controls stimulation generator 84 to deliver electrical stimulation via electrode combinations formed by electrodes in one or more electrode arrays. For example, stimulation generator 84 may deliver electrical stimulation therapy via electrodes on one or more leads 16, e.g., as stimulation pulses or continuous waveforms. Components described as processors within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination. The functions attributed to processors described herein may be embodied as software, firmware, hardware, or any combination thereof.

Stimulation generator 84 may include stimulation generation circuitry to generate stimulation pulses or continuous waveforms and, in some examples, switching circuitry to switch the stimulation across different electrode combinations, e.g., in response to control by processor 80. In particular, processor 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources to drive more than one electrode combination at one time. In this case, stimulation generator 84 may decrease current to the first electrode combination and simultaneously increase current to the second electrode combination to shift the stimulation therapy.

An electrode configuration, e.g., electrode combination and associated electrode polarities, may be represented by a data stored in a memory location, e.g., in memory 82, of IMD 14. Processor 80 may access the memory location to determine the electrode combination and control stimulation generator 84 to deliver electrical stimulation via the indicated electrode combination. To adjust electrode combinations, amplitudes, pulse rates, or pulse widths, processor 80 may command stimulation generator 84 to make the appropriate changes to therapy according to instructions within memory 82 and rewrite the memory location to indicate the changed therapy. In other examples, rather than rewriting a single memory location, processor 80 may make use of two or more memory locations. As previously mentioned, in some example, the instructions stored in memory 82 may allow processor to control stimulation generator 84 to make parameter adjustments over a transition period, in which the parameter is ramped to the desired value.

When activating stimulation, processor 80 may access not only the memory location specifying the electrode combination but also other memory locations specifying various stimulation parameters such as voltage or current amplitude, pulse width and pulse rate. Stimulation generator 84, e.g., under control of processor 80, then makes use of the electrode combination and parameters in formulating and delivering the electrical stimulation to patient 12.

According to examples described herein, such stimulation parameters may be adjusted to modify stimulation therapy delivered by IMD 14 based on the detected posture state of patient 12. In some examples, processor 80 may detect a posture state of patient 12 via posture state module 86 that indicates that a modification of the stimulation therapy is appropriate, e.g., according to instructions stored in memory 82. Processor 80 may access instructions for modifying the stimulation therapy based on the patient 12 posture state, e.g., by changing from a stimulation program appropriate for the previous posture state to a stimulation program appropriate for patient's current posture state.

Depending on the parameter values defined by the respective program, an adjustment may be made to one or more or the parameter values as a result of a detected change in patient posture. Processor 80 may also access for execution of the parameter adjustment over a transition period, e.g., by ramping the parameter from the existing value to the desired value of the new program according to a specific rate of change. Based on those instructions, processor 80 may control the stimulation parameter adjustment by sending an appropriate command to stimulation generator 84, which receives the command and ramps the respective stimulation parameter according to specified rate of change, thereby modifying the stimulation therapy being delivered to patient 12 based on the detected posture state of patient 12.

An exemplary range of electrical stimulation parameters likely to be effective in treating chronic pain, e.g., when applied to spinal cord 18, are listed below. While stimulation pulses are described, stimulation signals may be of any of a variety of forms such as sine waves or the like.

1. Pulse Rate: between approximately 0.5 Hz and approximately 1200 Hz, more preferably between approximately 5 Hz and approximately 250 Hz, and still more preferably between approximately 30 Hz and approximately 130 Hz.

2. Amplitude: between approximately 0.1 volts and approximately 50 volts, more preferably between approximately 0.5 volts and approximately 20 volts, and still more preferably between approximately 1 volt and approximately 10 volts. In other examples, a current amplitude may be defined as the biological load in the voltage that is delivered. For example, the range of current amplitude may be between approximately 0.1 milliamps (mA) and approximately 50 mA.

3. Pulse Width: between approximately 10 microseconds and approximately 5000 microseconds, more preferably between approximately 100 microseconds and approximately 1000 microseconds, and still more preferably between approximately 180 microseconds and approximately 450 microseconds.

In other applications, different ranges of parameter values may be used. For DBS, as one example, alleviation or reduction of symptoms associated with Parkinson's disease, essential tremor, epilepsy, psychiatric disorders or other disorders may make use of stimulation having a pulse rate in the range of approximately 0.5 to approximately 1200 Hz, such as between approximately 5 to approximately 250 Hz, or between approximately 30 to approximately 185 Hz, and a pulse width in the range of approximately 10 microseconds and 5000 microseconds, such as between approximately 60 microseconds and approximately 1000 microseconds, or between approximately 60 microseconds and approximately 450 microseconds, or between approximately 60 microseconds and approximately 150 microseconds. Amplitude ranges such as those described above with reference to SCS, or other amplitude ranges, may be used for different DBS applications.

Processor 80 accesses stimulation parameters in memory 82, e.g., as programs and groups of programs. Upon selection of a particular program group, processor 80 may control stimulation generator 84 to generate and deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processor 80 also may control telemetry circuit 88 to send and receive information to and from external programmer 20. For example, telemetry circuit 88 may send information to and receive information from patient programmer 30.

Posture state module 86 allows IMD 14 to sense the patient posture state, e.g., posture, activity or any other static position or motion of patient 12. In the example of FIG. 4, posture state module 86 includes one or more accelerometers, such as three-axis accelerometers, capable of detecting static orientation or vectors in three-dimensions. Example accelerometers include a micro-electro-mechanical accelerometer. In other examples, posture state module 86 may alternatively or additionally include one or more gyroscopes, piezoelectric crystals, pressure transducers or other sensors to sense the posture state of patient 12. Posture state information generated by posture state module 86 and processor 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 (e.g., via patient programmer 30), or some combination thereof. As an example, processor 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture. IMD 14 may also store which group or program was being used to deliver therapy when patient 12 was in the sensed posture. Further, processor 80 may also adjust therapy for a new posture when posture state module 86 indicates that patient 12 has in fact changed postures. Therefore, IMD 14 may be configured to provide posture responsive stimulation therapy to patient 12. Stimulation adjustments in response to posture state may be automatic or semi-automatic (subject to patient approval). In many cases, fully automatic adjustments may be desirable so that IMD 14 may react more quickly to posture state changes.

A posture state parameter value from posture state module 86 that indicates the posture state may constantly vary throughout the day of patient 12. However, a certain activity (e.g., walking, running, or biking) or a posture (e.g., standing, sitting, or lying down) may include multiple posture state parameter values from posture state module 86. Memory 82 may include definitions for each posture state of patient 12. In one example, the definition of each posture state may be illustrated as a cone in three-dimensional space. Whenever the posture state parameter value, e.g., a vector, from the three-axis accelerometer of posture state module 86 resides within a predefined cone, processor 80 indicates that patient 12 is in the posture state of the cone. In other examples, posture state parameter value from the 3-axis accelerometer may be compared to a look-up table or equation to determine the posture state in which patient 12 currently resides.

Posture responsive stimulation may allow IMD 14 to implement a certain level of automation in therapy adjustments. Automatically adjusting stimulation may free patient 12 from the constant task of manually adjusting therapy each time patient 12 changes posture or starts and stops a certain posture state. Such manual adjustment of stimulation parameters can be tedious, requiring patient 14 to, for example, depress one or more keys of patient programmer 30 multiple times during the patient posture state to maintain adequate symptom control. In some examples, patient 12 may eventually be able to enjoy posture state responsive stimulation therapy without the need to continue making changes for different postures via patient programmer 30. Instead, patient 12 may transition immediately or over time to fully automatic adjustments based on posture state.

Although posture state module 86 is described as containing the 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple posture state sensors placed at various locations on or within the body of patient 12.

In other examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processor 80, in some examples, to confirm or reject changes in sensed posture state that may result from vibration, patient travel (e.g., in an aircraft, car or train), or some other false positive of posture state.

In some examples, processor 80 processes the analog output of the posture state sensor in posture state module 86 to determine activity and/or posture data. For example, where the posture state sensor comprises an accelerometer, processor 80 or a processor of posture state module 86 may process the raw signals provided by the posture state sensor to determine activity counts. In some examples, processor 80 may process the signals provided by the posture state sensor to determine velocity of motion information along each axis.

In one example, each of the x, y, and z signals provided by the posture state sensor has both a DC component and an AC component. The DC components describes the gravitational force exerted upon the sensor and can thereby be used to determine orientation of the sensor within the gravitational field of the earth. Assuming the orientation of the sensor is relatively fixed with respect to the patient, the DC components of the x, y and z signals may be utilized to determine the patient's orientation within the gravitational field, and hence to determine the posture of the patient.

The AC component of the x, y and z signals yields information about patient motion. In particular, the AC component of a signal may be used to derive a value for an activity describing the patient's motion. This activity may involve a level, direction of motion, or acceleration of the patient.

One method for determining the patient activity is by determining an activity count. An activity count may be used to indicate the activity or activity level of patient 12. For example, a signal processor may sum the magnitudes of the AC portion of an accelerometer signal for N consecutive samples. For instance, assuming sampling occurs as 25 Hz, N may be set to 25, so that count logic provides the sum of the samples that are obtained in one second. This sum may be referred to as an "activity count". The number "N" of consecutive samples may be selected by the processor based on the current posture state, if desired. The activity count may be the activity portion of the activity parameter value that is added to the posture portion. The resulting activity parameter value may then incorporate both activity and posture to generate an accurate indication of the motion of patient 12.

As another example, the activity parameter value may be defined describing direction of motion. This activity parameter value may be associated with a vector and an associated tolerance, which may be a distance from the vector. Another example of an activity parameter value relates to acceleration. The value quantifying a level of change of motion over time in a particular direction may be associated with this parameter referenced in the activity parameter value.

IMD 14 wirelessly communicates with external programmer 20, e.g., patient programmer 30 or clinician programmer 60, or another device by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some examples, power requirements may be small enough to allow IMD 14 to utilize patient motion and implement a kinetic energy-scavenging device to trickle charge a rechargeable battery. In other examples, traditional batteries may be used for a limited period of time. As a further alternative, an external inductive power supply could transcutaneously power IMD 14 when needed or desired.

Figure 5:
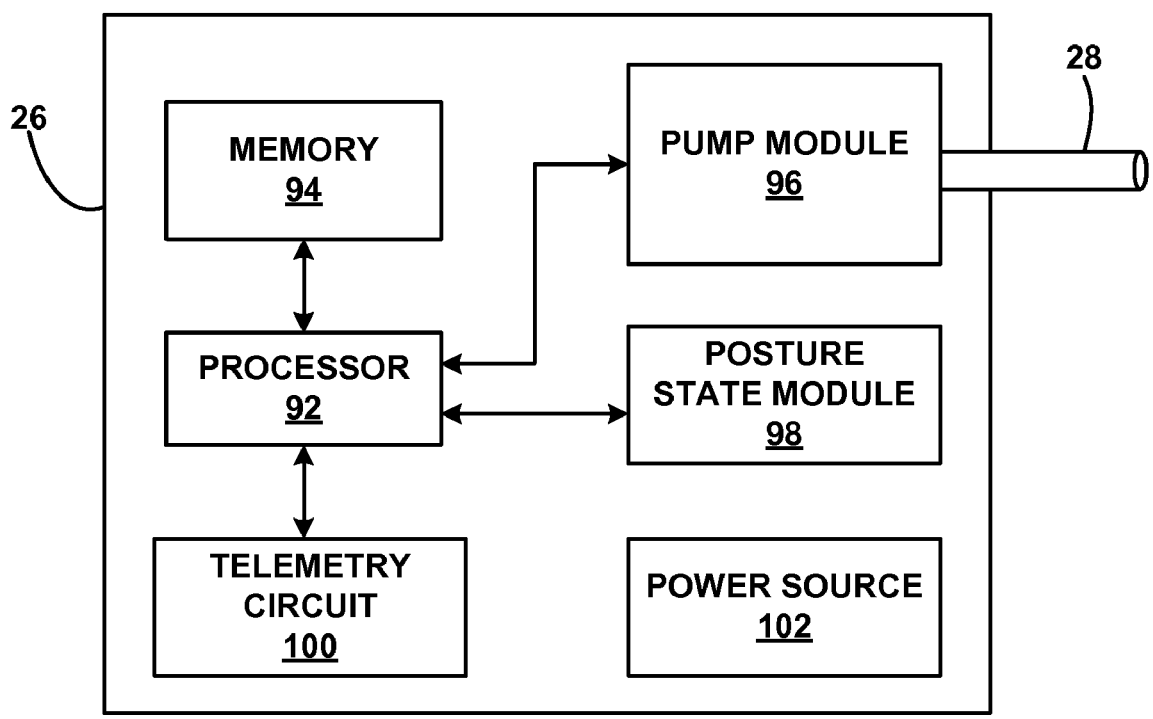
FIG. 5 is a functional block diagram illustrating various components of an example implantable drug pump.

FIG. 5 is a functional block diagram illustrating various components of an IMD 26, which delivers a therapeutic agent to patient 12. IMD 26 is a drug pump that operates substantially similar to IMD 14 of FIG. 4, but delivers a therapeutic agent instead of electrical stimulation. IMD 26 includes processor 92, memory 94, pump module 96, posture state module 98, telemetry circuit 100, and power source 102. Instead of stimulation generator 84 of IMD 14, IMD 26 includes pump module 96 for delivering drugs or some other therapeutic agent via catheter 28. Pump module 96 may include a reservoir to hold the drug and a pump mechanism to force drug out of catheter 28 and into patient 12.

Processor 92 controls pump module 96 according to therapy instructions stored within memory 94. For example, memory 94 may contain the programs or groups of programs that define the drug delivery therapy for patient 12. A program may indicate the bolus size or flow rate of the drug, and processor 92 may accordingly deliver therapy. Processor 92 may also use posture state information from posture state 98 to adjust drug delivery therapy when patient 12 changes posture states, e.g., adjusts his or her posture.

Figure 6:
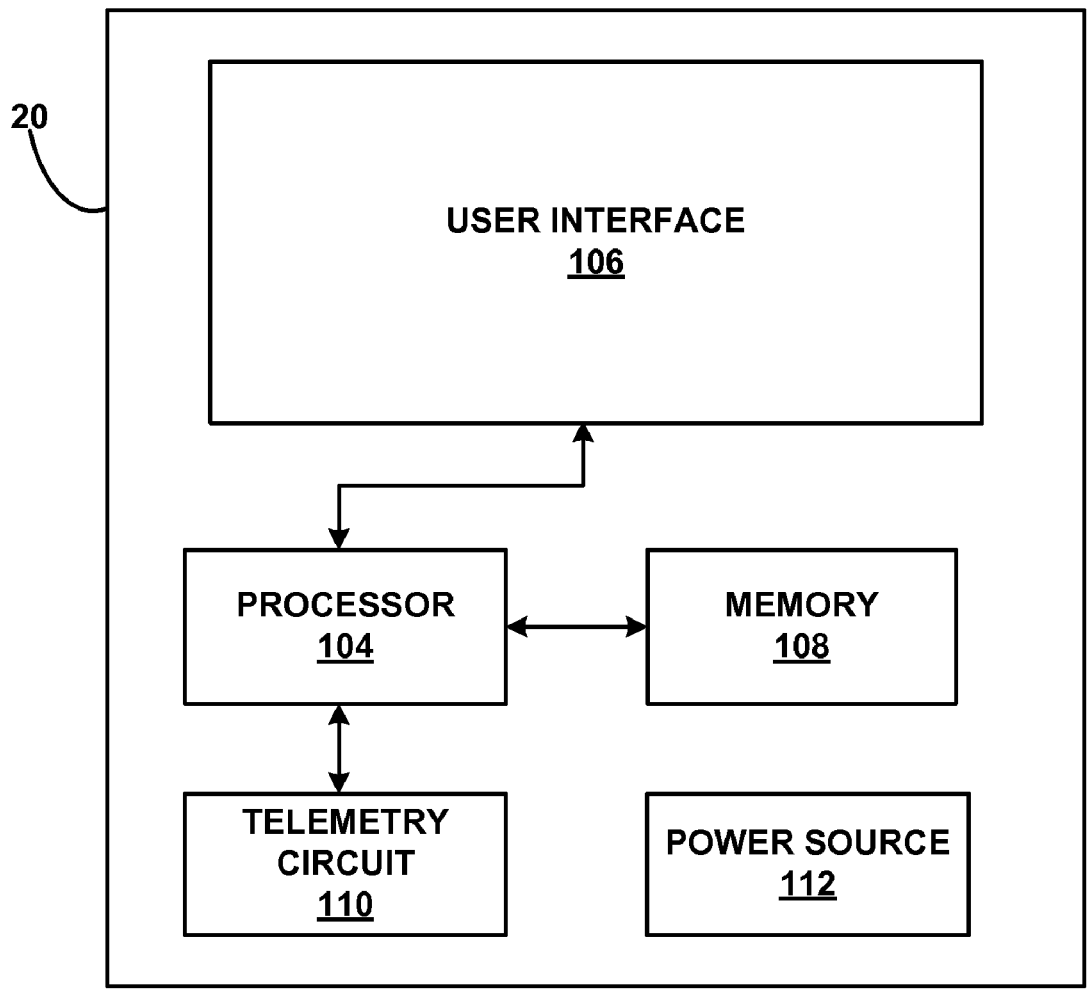
FIG. 6 is a functional block diagram illustrating various components of an example external programmer for an implantable medical device.

FIG. 6 is a functional block diagram illustrating various components of an external programmer 20 for IMDs 14 or 26. Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming the IMD. As shown in FIG. 6, external programmer 20 includes processor 104, memory 108, telemetry circuit 110, user interface 106, and power source 112. External programmer 20 may be embodied as patient programmer 30 (FIG. 2) or clinician programmer 60 (FIG. 3).

Processor 104 processes instructions by memory 108 and may store user input received through user interface 106 into the memory when appropriate for the current therapy. In addition, processor 104 provides and supports any of the functionality described herein with respect to each example of user interface 106. Processor 104 may comprise any one or more of a microprocessor, DSP, ASIC, FPGA, or other digital logic circuitry, and the functions attributed to programmer 104 may be embodied as software, firmware, hardware or any combination thereof.

Memory 108 may include any one or more of a RAM, ROM, EEPROM, flash memory or the like. Memory 108 may include instructions for operating user interface 106, telemetry module 110 and managing power source 112. Memory 108 may store program instructions that, when executed by processor 104, cause processor 104 and programmer 20 to provide the functionality ascribed to them herein. Memory 108 also includes instructions for generating and delivering programming commands to IMD 14, such as a programming command that instructs IMD 14 to activate or deactivate a posture responsive therapy mode. Memory 108 may also include a removable memory portion that may be used to provide memory updates or increases in memory capacities. A removable memory may also allow patient data to be easily transferred to another computing device, or to be removed before programmer 20 is used to program therapy for another patient.

A clinician, patient 12 or another user (e.g., a patient caretaker) interacts with user interface 106 in order to manually change the stimulation parameter values of a program, change programs within a group, turn posture responsive stimulation ON or OFF, view therapy information, view posture state information, or otherwise communicate with IMDs 14 or 26.

User interface 106 may include a screen and one or more input mechanisms, such as buttons as in the example of patient programmer 30, that allow external programmer 20 to receive input from a user. Alternatively, user interface 106 may additionally or only utilize a touch screen display, as in the example of clinician programmer 60. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Telemetry circuit 110 allows the transfer of data to and from IMD 14, or IMD 26. Telemetry circuit 110 may communicate automatically with IMD 14 at a scheduled time or when the telemetry circuit detects the proximity of the stimulator. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

Although not shown in FIG. 6, in some examples, external programmer 20 may include a charger module capable of recharging a power source, such as a rechargeable battery that may be included in power source 90 of IMD 14. Hence, in some cases, the programmer may be integrated with recharging components to form a combined programmer/recharger unit.

Figure 7:
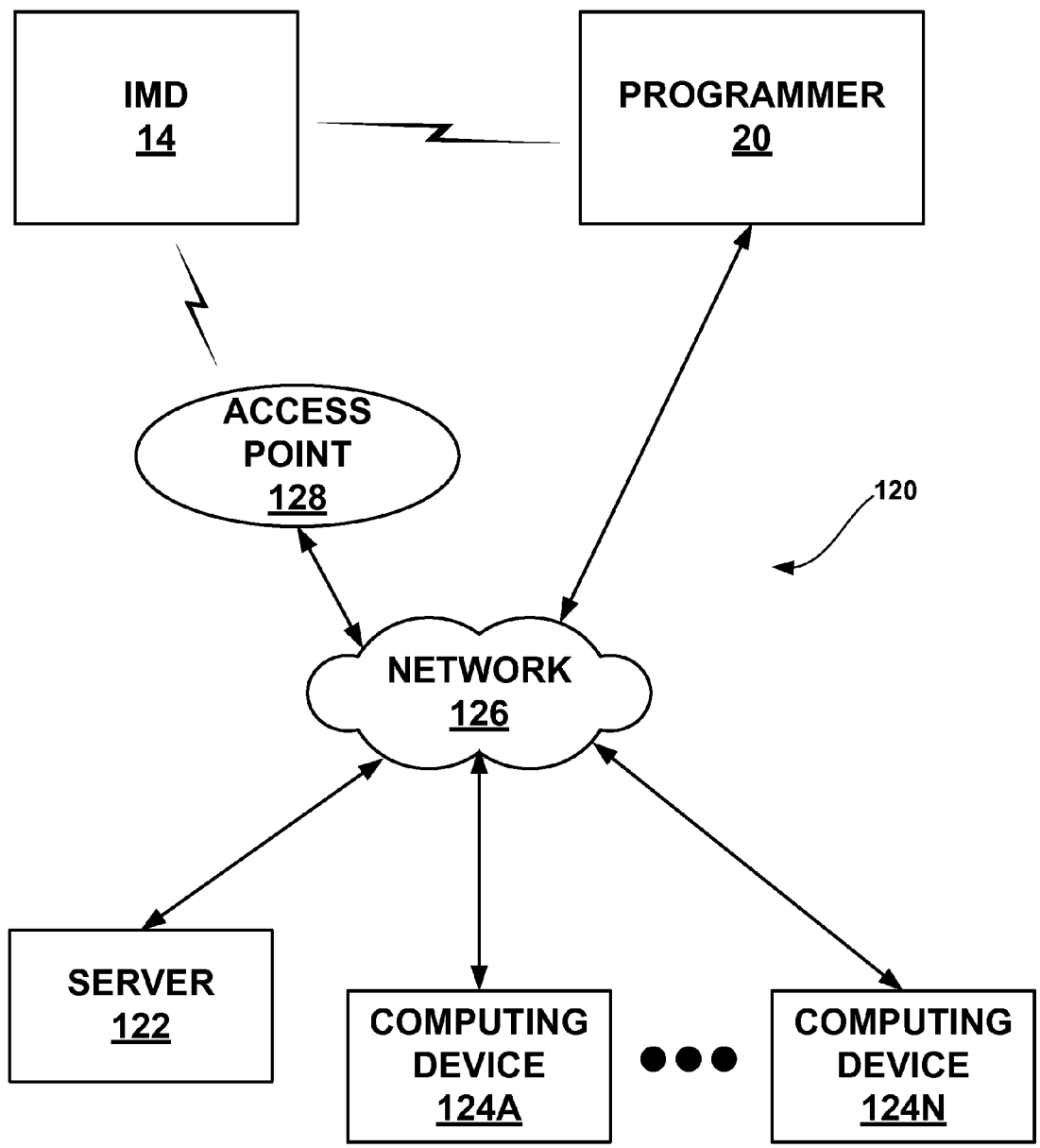
FIG. 7 is a block diagram illustrating an example system that includes an external device, such as a server, and one or more computing devices that are coupled to an implantable medical device and external programmer shown in FIGS. 1A-1C via a network.

FIG. 7 is a block diagram illustrating an example system 120 that includes an external device, such as a server 122, and one or more computing devices 124A-124N, that are coupled to IMD 14 and external programmer 20 shown in FIGS. 1A-1C via a network 126. In this example, IMD 14 may use its telemetry circuit 88 (FIG. 4) to communicate with external programmer 20 via a first wireless connection, and to communication with an access point 128 via a second wireless connection. In other examples, IMD 26 may also be used in place of IMD 14, and external programmer 20 may be either patient programmer 30 or clinician programmer 60.

In the example of FIG. 7, access point 128, external programmer 20, server 122, and computing devices 124A-124N are interconnected, and able to communicate with each other, through network 126. In some cases, one or more of access point 128, external programmer 20, server 122, and computing devices 124A-124N may be coupled to network 126 through one or more wireless connections. IMD 14, external programmer 20, server 122, and computing devices 124A-

124N may each comprise one or more processors, such as one or more microprocessors, DSPs, ASICs, FPGAs, programmable logic circuitry, or the like, that may perform various functions and operations, such as those described in this disclosure.

Access point 128 may comprise a device, such as a home monitoring device, that connects to network 126 via any of a variety of connections, such as telephone dial-up, digital subscriber line (DSL), or cable modem connections. In other examples, access point 128 may be coupled to network 126 through different forms of connections, including wired or wireless connections.

During operation, IMD 14 may collect and store various forms of data. For example, IMD 14 may collect sensed posture state information during therapy that indicate how patient 12 moves throughout each day. In some cases, IMD 14 may directly analyze the collected data to evaluate the patient 12 posture state, such as what percentage of time patient 12 was in each identified posture. In other cases, however, IMD 14 may send stored data relating to posture state information to external programmer 20 and/or server 122, either wirelessly or via access point 128 and network 126, for remote processing and analysis. For example, IMD 14 may sense, process, trend and evaluate the sensed posture state information. This communication may occur in real time, and network 126 may allow a remote clinician to review the current patient posture state by receiving a presentation of a posture state indication on a remote display, e.g., computing device 124A. Alternatively, processing, trending and evaluation functions may be distributed to other devices such as external programmer 20 or server 122, which are coupled to network 126. In addition, posture state information may be archived by any of such devices, e.g., for later retrieval and analysis by a clinician.

In some cases, IMD 14, external programmer 20 or server 122 may process posture state information or raw data and/or therapy information into a displayable posture state report, which may be displayed via external programmer 20 or one of computing devices 124A-124N. The posture state report may contain trend data for evaluation by a clinician, e.g., by visual inspection of graphic data. In some cases, the posture state report may include the number of activities patient 12 conducted, a percentage of time patient 12 was in each posture state, the average time patient 12 was continuously within a posture state, what group or program was being used to deliver therapy during each activity, the number of adjustments to therapy during each respective posture state, or any other information relevant to patient 12 therapy, based on analysis and evaluation performed automatically by IMD 14, external programmer 20 or server 122. A clinician or other trained professional may review and/or annotate the posture state report, and possibly identify any problems or issues with the therapy that should be addressed.

In the manner of FIG. 7, a clinician, physician, technician, or even patient 12, may review objectivity data with respect to the posture states of patient 12. The objectivity data may be sleep quality information or proportional posture information that indicates how patient 12 has been moving during the symptom diagnosis or delivered therapy. The user may remotely monitor the progress and trends of patient 12, limiting the number of times that patient 12 may need to physically visit the clinician. The remote monitoring supported by system 120 may also reduce the time needed to find efficacious therapy parameters by allowing the clinician to more frequently monitor sleep quality information and proportional posture information. Any of the user interfaces described herein with respect to patient programmer 30 or clinician programmer 60 may also be presented via any of computing devices 124A-124N.

In some cases, server 122 may be configured to provide a secure storage site for archival of posture state information that has been collected from IMD 14 and/or external programmer 20. Network 126 may comprise a local area network, wide area network, or global network, such as the Internet. In some cases, external programmer 20 or server 122 may assemble posture state information in web pages or other documents for viewing by trained professionals, such as clinicians, via viewing terminals associated with computing devices 124A-124N. System 120 may be implemented, in some aspects, with general network technology and functionality similar to that provided by the Medtronic CareLink® Network developed by Medtronic, Inc., of Minneapolis, Minn.

Although some examples of the disclosure may involve posture state information and data, system 120 may be employed to distribute any information relating to the treatment of patient 12 and the operation of any device associated therewith. For example, system 120 may allow therapy errors or device errors to be immediately reported to the clinician. In addition, system 120 may allow the clinician to remotely intervene in the therapy and reprogram IMD 14, patient programmer 30, or communicate with patient 12. In an additional example, the clinician may utilize system 120 to monitor multiple patients and share data with other clinicians in an effort to coordinate rapid evolution of effective treatment of patients.

Furthermore, although the disclosure is described with respect to SCS therapy, such techniques may be applicable to IMDs that convey other therapies in which posture state information is important, such as, e.g., DBS, pelvic floor stimulation, gastric stimulation, occipital stimulation, functional electrical stimulation, and the like. Also, in some aspects, techniques for evaluating posture state information, as described in this disclosure, may be applied to IMDs that are generally dedicated to sensing or monitoring and do not include stimulation or other therapy components. For example, an implantable monitoring device may be implanted in conjunction with an implantable stimulation device, and be configured to evaluate sensing integrity of leads or electrodes associated with the implantable monitoring device based on sensed signals evoked by delivery of stimulation by the implantable stimulation device.

Figure 8A:
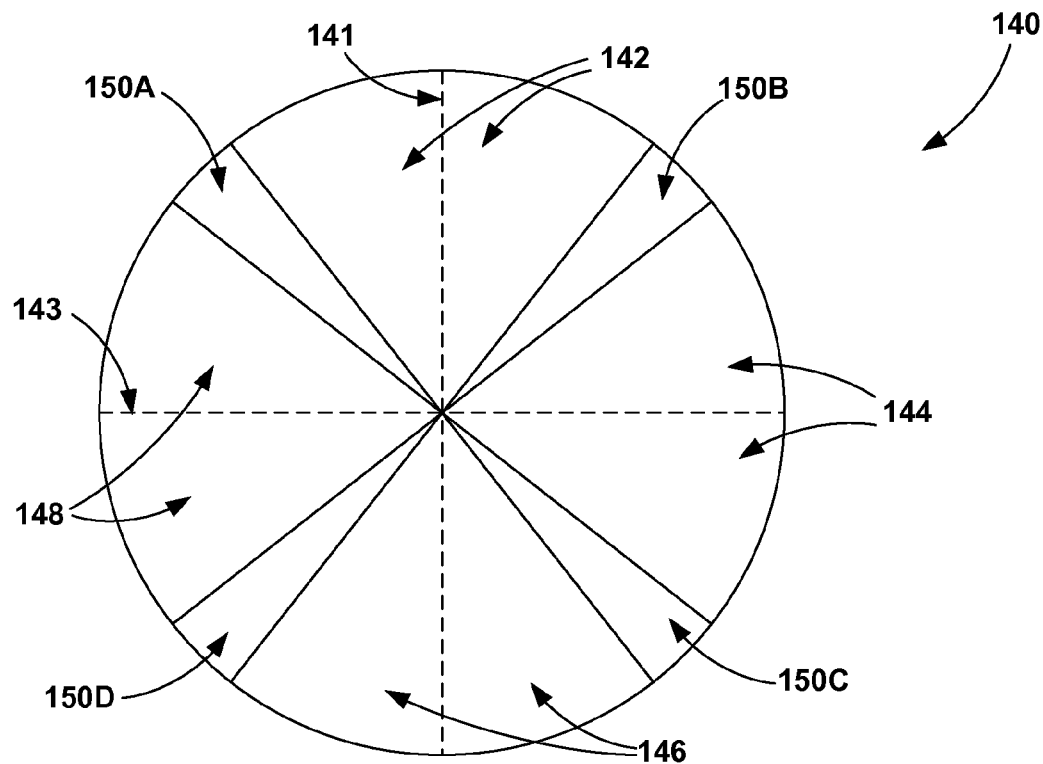
FIGS. 8A-8C are conceptual illustrations of example posture state spaces within which postures state reference data may define the posture state of a patient.
Figure 8B:
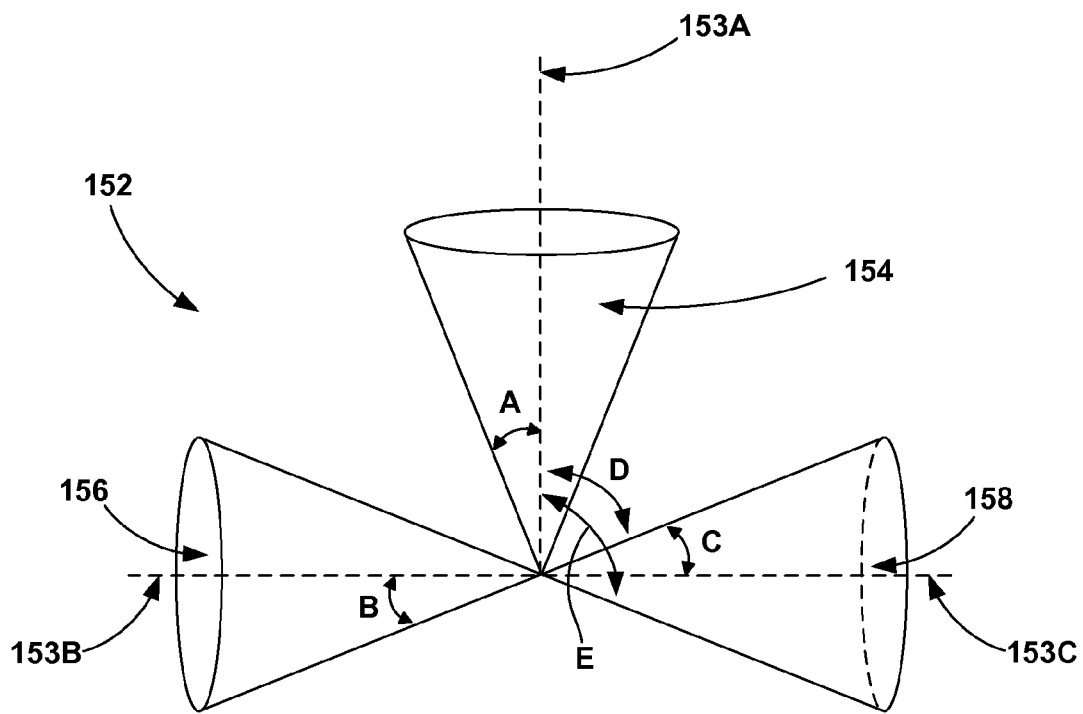
Figure 8C:
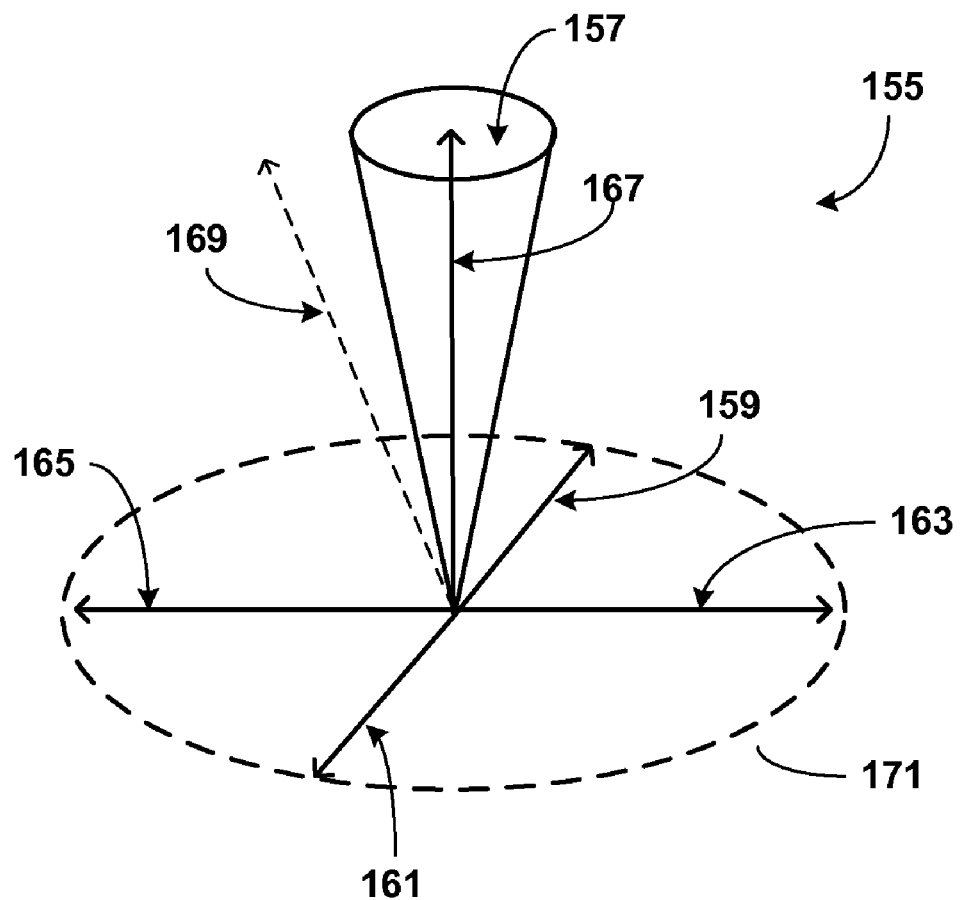

FIGS. 8A-8C are conceptual illustrations of posture state spaces 140, 152, 155 within which posture state reference data may define the posture state of patient 12. Posture state reference data may define certain regions associated with particular posture states of patient 12 within the respective posture state spaces 140, 152, 155. The output of one or more posture state sensors may be analyzed by posture state module 86 with respect to posture state spaces 140, 152, 155 to determine the posture state of patient 12. For example, if the output of one or more posture state sensors is within a particular posture region defined by posture state reference data, posture state module 86 may determine that patient 12 is within the posture state associated with the respective posture state region.

In some cases, one or more posture state regions may be defined as posture state cones. Posture state cones may be used to define a posture state of patient 12 based on the output from a posture state sensor of a posture state according to an example method for posture state detection. A posture state cone may be centered about a posture state reference coordinate vector that corresponds to a particular posture state. In the examples of FIGS. 8A and 8B, the posture state module 86 of IMD 14 or IMD 26 may use a posture state sensor, e.g., a three-axis accelerometer that provides data indicating the posture state of patient 12, to sense posture vectors. While the sensed data may be indicative of any posture state, postures of patient 12 will generally be used below to illustrate the concept of posture cones. As shown in FIG. 8A, posture state space 140 represents a vertical plane dividing patient 12 from left and right sides, or the sagittal plane. A posture state parameter value from two axes of the posture state sensor may be used to determine the current posture state of patient 12 according to the posture state space 140. The posture state data may include x, y and z coordinate values.

A posture cone may be defined by a reference coordinate vector for a given posture state in combination with a distance or angle defining a range of coordinate vectors within a cone surrounding the posture reference coordinate vector. Alternatively, a posture cone may be defined by a reference coordinate vector and a range of cosine values computed using the reference coordinate vector as an adjacent vector and any of the outermost vectors of the cone as a hypotenuse vector. If a sensed posture state vector is within an applicable angle or distance of the reference coordinate vector, or if the sensed posture state vector and the reference coordinate vector produce a cosine value in a specified cosine range, then posture state vector is determined to reside within the posture cone defined by the reference coordinate vector.

Posture state space 140 is segmented into different posture cones that are indicative of a certain posture state of patient 12. In the example of FIG. 8A, upright cone 142 indicates that patient 12 is sitting or standing upright, lying back cone 148 indicates that patient 12 is lying back down, lying front cone 144 indicates that patient 12 is lying chest down, and inverted cone 146 indicates that patient 12 is in an inverted position. Other cones may be provided, e.g., to indicate that patient 12 is lying on the right side or left side. For example, a lying right posture cone and a lying left posture cone positioned outside of the sagittal plane illustrated in FIG. 8A. In particular, the lying right and lying left posture cones may be positioned in a coronal plane substantially perpendicular to the sagittal plane illustrated in FIG. 8A. For ease of illustration, lying right and lying left cones are not shown in FIG. 8A.

Vertical axis 141 and horizontal axis 143 are provided for orientation of posture state area 140, and are shown as orthogonal for purposes of illustration. However, posture cones may have respective posture reference coordinate vectors that are not orthogonal in some cases. For example, individual reference coordinate vectors for cones 142 and 146 may not share the same axis, and reference coordinate vectors for cones 144 and 148 may not share the same axis. Also, reference coordinate vectors for cones 144 and 148 may or may not be orthogonal to reference coordinates vectors for cones 142, 146. Therefore, although orthogonal axes are shown in FIG. 8A for purposes of illustration, respective posture cones may be defined by individualized reference coordinate vectors for the cones.

IMD 14 may monitor the posture state parameter value of the posture state sensor to produce a sensed coordinate vector and identify the current posture of patient 12 by identifying which cone the sensed coordinated vector of the posture state sensor module 86 resides. For example, if the posture state parameter value corresponds to a sensed coordinate vector that falls within lying front cone 144, IMD 14 determines that patient 12 is lying down on their chest. IMD 14 may store this posture information as a determined posture state or as raw output from the posture state sensor, change therapy according to the posture, or both. Additionally, IMD 14 may communicate the posture information to patient programmer 30 so that the patient programmer can present a posture state indication to patient 12.

In addition, posture state area 140 may include hysteresis zones 150A, 150B, 150C, and 150D (collectively "hysteresis zones 150"). Hysteresis zones 150 are positions within posture state area 140 where no posture cones have been defined. Hysteresis zones 150 may be particularly useful when IMD 14 utilizes the posture state information and posture cones to adjust therapy automatically. If the posture state sensor indicates that patient 12 is in upright cone 142, IMD 14 would not detect that patient 12 has entered a new posture cone until the posture state parameter value indicates a different posture cone. For example, if IMD 14 determines that patient 12 moves to within hysteresis zone 150A from upright cone 142, IMD 14 retains the posture as upright. In this manner, IMD 14 does not change the corresponding therapy until patient 12 fully enters a different posture cone. Hysteresis zones 150 prevent IMD 14 from continually oscillating between different therapies when patient 12's posture state resides near a posture cone boundary.

Each posture cone 142, 144, 146, 148 may be defined by an angle in relation to a reference coordinate vector defined for the respective posture cone. Alternatively, some posture cones may be defined by an angle relative to a reference coordinate vector for another posture cone. For example, lying postures may be defined by an angle with respect to a reference coordinate vector for an upright posture cone. In each case, as described in further detail below, each posture cone may be defined by an angle in relation to a reference coordinate posture vector defined for a particular posture state. The reference coordinate vector may be defined based on posture sensor data generated by a posture state sensor while patient 12 occupies a particular posture state desired to be defined using the reference coordinate vector. For example, a patient may be asked to occupy a posture so that a reference coordinate vector can be sensed for the respective posture. In this manner, vertical axis 141 may be specified according to the patient's actual orientation. Then, a posture cone can be defined using the reference coordinate vector as the center of the cone.

Vertical axis 141 in FIG. 8A may correspond to a reference coordinate vector sensed while the patient was occupying an upright posture state. Similarly, a horizontal axis 143 may correspond to a reference coordinate vector sensed while the patient is occupying a lying posture state. A posture cone may be defined with respect to the reference coordinate vector. Although a single axis is shown extending through the upright and inverted cones 142, 146, and another single axis is shown extending through the lying down and lying up cones 144, 148, individual reference coordinate vectors may be used for respective cones, and the reference coordinate vectors may not share the same axes, depending on differences between the reference coordinate vectors obtained for the posture cones.

Posture cones may be defined by the same angle or different angles, symmetrical to either axis, or asymmetrical to either axis. For example, upright cone 142 may have an angle of eighty degrees, +40 degrees to −40 degrees from the positive vertical axis 141. In some cases, lying cones may be defined relative to the reference coordinate vector of the upright cone 142. For example, lying up cone 148 may have an angle of eighty degrees, −50 degrees to −130 degrees from the positive vertical axis 141. Inverted cone 146 may have an angle of eighty degrees, −140 degrees to +140 degrees from vertical axis 141. In addition, lying down cone 144 may have an angle of eighty degrees, +50 degrees to +130 degrees from the positive vertical axis 141. In other examples, each posture cone may have varying angle definitions, and the angles may change during therapy delivery to achieve the most effective therapy for patient 12.

Alternatively or additionally, instead of an angle, posture cones 144, 146, 148, 148 may be defined by a cosine value or range of cosine values in relation to vertical axis 141, horizontal axis 143, or some other axis, such as, e.g., individual reference coordinate vectors for the respective cones. For example, a posture cone may be defined by a cosine value that defines the minimum cosine value, calculated using a reference coordinate vector and a respective coordinate vector sensed by a posture state sensor at any point in time. In the cosine computation, the value (adjacent/hypotenuse) can be computed using the magnitude of the coordinate reference vector as the adjacent and a vector at the outermost extent of the cone as the hypotenuse to define a range of cosine values consistent with the outer bound of the cone.

For upright cone 142, the cosine range may extend from the maximum cosine value of 1.0, corresponding to a sensed vector that matches the reference coordinate vector of the upright cone, to a minimum cosine value that corresponds to a sensed vector at the outer limit of the upright cone. As another example, for lying cone 144, the cosine range may extend from the maximum cosine value of 1.0, corresponding to a sensed vector that matches the reference coordinate vector of the lying cone, to a minimum cosine value that corresponds to a sensed vector at the outer limit of the lying cone. Alternatively, the lying cone 144 may be defined with reference to the upright cone 142, such that the cosine range may extend between a maximum and minimum values determined relative to the reference coordinate vector for the upright cone.

In other examples, posture state area 140 may include additional posture cones than those shown in FIG. 8A. For example, a reclining cone may be located between upright cone 142 and lying back cone 148 to indicate when patient 12 is reclining back (e.g., in a dorsal direction). In this position, patient 12 may need a different therapy to effectively treat symptoms. Different therapy programs may provide efficacious therapy to patient 12 when patient 12 is in each of an upright posture (e.g., within upright cone 142), lying back posture (e.g., within lying back cone 148), and a reclining back posture. Thus, a posture cone that defines the reclining back posture may be useful for providing efficacious posture-responsive therapy to patient 12. In other examples, posture state area 140 may include fewer posture cones than cones 142, 144, 146, 148 shown in FIG. 8A. For example, inverted cone 146 may be replaced by a larger lying back cone 148 and lying front cone 144.

FIG. 8B illustrates an example posture state space 152 that is a three-dimensional space in which the posture state parameter value from the posture state sensor is placed in relation to the posture cones. Posture state space 152 is substantially similar to posture state area 140 of FIG. 8A. However, the posture state parameter value derived from all three axes of a 3-axis accelerometer may be used to accurately determine the posture state of patient 12. In the example of FIG. 8B, posture state space 152 includes upright cone 154, lying back cone 156, and lying front cone 158. Posture state space 152 also includes hysteresis zones (not shown) similar to those of posture state area 140. In the example of FIG. 8B, the hysteresis zones are the spaces not occupied by a posture cone, e.g., upright cone 154, lying back cone 156, and lying front cone 158.

Posture cones 154, 156 and 158 also are defined by a respective center line 153A, 153B, or 153C, and associated cone angle A, B or C. For example, upright cone 154 is defined by center line 153A that runs through the center of upright cone 154. Center line 153A may correspond to an axis of the posture state sensor or some other calibrated vector. In some embodiments, each center line 153A, 153B, 153C may correspond to a posture reference coordinate vectors defined for the respective postures, e.g., the upright posture. For instance, assuming that patient 12 is standing, the DC portion of the x, y, and z signals detected by the posture state sensor of posture state module 86 define a posture vector that corresponds to center line 153A. The x, y, and z signals may be measured while patient 12 is known to be in a specified position, e.g., standing, and the measured vector may be correlated with the upright posture state. Thereafter, when the DC portions of the posture state sensor signal are within some predetermined cone tolerance or proximity, e.g., as defined by an angle, distance or cosine value, of the posture reference coordinate vector (i.e., center line 153A), it may be determined that patient 12 is in the upright posture. In this manner, a sensed posture coordinate vector may be initially measured based on the output of one or more posture state sensors of posture state module 86, associated with a posture state, such as upright, as a reference coordinate vector, and then later used to detect a patient's posture state.

As previously indicated, it may be desirable to allow some tolerance to be associated with a defined posture state, thereby defining a posture cone or other volume. For instance, in regard to the upright posture state, it may be desirable to determine that a patient who is upright but leaning slightly is still in the same upright posture state. Thus, the definition of a posture state may generally include not only a posture reference coordinate vector (e.g., center line 153A), but also a specified tolerance. One way to specify a tolerance is by providing an angle, such as cone angle A, relative to coordinate reference vector 153A, which results in posture cone 154 as described herein. Cone angle A is the deflection angle, or radius, of upright cone 154. The total angle that each posture cone spans is double the cone angle. The cone angles A, B, and C may be generally between approximately 1 degree and approximately 70 degrees. In other examples, cone angles A, B, and C may be between approximately 10 degrees and 30 degrees. In the example of FIG. 8B, cone angles A, B, and C are approximately 20 degrees. Cone angles A, B, and C may be different, and center lines 153A, 153B, and 153C may not be orthogonal to each other.

In some examples, a tolerance may be specified by a cosine value or range of cosine values. The use of cosine values, in some cases, may provide substantial processing efficiencies. As described above, for example, a minimum cosine value, determined using the reference coordinate vector as adjacent and sensed coordinate vector as hypotenuse, indicates the range of vectors inside the cone. If a sensed coordinate vector, in conjunction with the reference coordinate vector for a posture cone, produces a cosine value that is less than the minimum cosine value for the posture cone, the sensed coordinate vector does not reside within the pertinent posture cone. In this manner, the minimum cosine value may define the outer bound of a range of cosine values within a particular posture cone defined in part by a reference coordinate vector.

While center lines 153A, 153B, 153C of each of the posture cones 154, 156, 158, respectively, are shown in FIG. 8B as being substantially orthogonal to each other, in other examples, center lines 153A, 153B, and 153C may not be orthogonal to each other. Again, the relative orientation of center lines 153A, 153B, 153C may depend on the actual reference coordinate vector output of the posture state sensor of posture state module 86 of IMD 14 when patient 12 occupies the respective postures.

In some cases, all of the posture cones may be individually defined based on actual reference coordinate vectors. Alternatively, in some cases, some posture cones may be defined with reference to one or more reference coordinate vectors for one or more other posture cones. For example, lying reference coordinate vectors could be assumed to be orthogonal to an upright reference coordinate vector. Alternatively, lying reference coordinate vectors could be individually determined based on sensed coordinate vectors when the patient is in respective lying postures. Hence, the actual reference coordinate vectors for different postures may be orthogonal or non-orthogonal with respect to one another.

In addition to upright cone 154, lying back cone 156, and lying front cone 158, posture state space 152 may include additional posture cones. For example, a lying right cone may be provided to define a patient posture in which patient 12 is lying on his right side and a lying left cone may be provided to define a patient posture in which patient 12 is lying on his left side. In some cases, the lying right cone and lying left cone may be positioned approximately orthogonal to upright cones 154, in approximately the same plane as lying back cone 156 and lying front cone 158. Moreover, posture state space 152 may include an inverted cone positioned approximately opposite of upright cone 154. Such a cone indicates that the patient's posture is inverted from the upright posture, i.e., upside down.

In some examples, to detect the posture state of a patient, posture state module 86 of IMD 14 may determine a sensed coordinate vector based on the posture sensor data generated by one or more posture state sensors, and then analyze the sensed coordinate vector with respect to posture cones 154, 156, 158 of FIG. 8B. For example, in a case in which a posture cone is defined by a reference coordinate vector and a tolerance angle, e.g., tolerance angle "A," posture state module 86 may determine whether the sensed coordinate vector is within upright posture cone 154 by calculating the angle between the sensed coordinate vector and reference coordinate vector, and then determine whether the angle is less than the tolerance angle "A." If so, posture state module 86 determines that the sensed coordinate vector is within upright posture cone 154 and detects that patient 12 is in the upright posture. If posture state module 86 determines that sensed coordinate vector is not within upright posture cone 154, posture state module 86 detects that patient 12 is not in the upright posture.

Posture state module 86 may analyze the sensed coordinate vector in posture state space 152 with respect to each individual defined posture cone, such as posture cones 156 and 158, in such a manner to determine the posture state of patient 12. For example, posture state module 86 may determine the angle between the sensed coordinate vector and reference coordinate vector of individual posture cones defined for the posture state, and compare the determined angle to the tolerance angle defined for the respective posture cone. In this manner, a sensed coordinate vector may be evaluated against each posture cone until a match is detected, i.e., until the sensed coordinate vector is found to reside in one of the posture cones. Hence, a cone-by-cone analysis is one option for posture detection.

In other examples, different posture detection analysis techniques may be applied. For example, instead of testing a sensed coordinate vector against posture cones on a cone-by-cone basis, a phased approach may be applied where the sensed coordinate vector is classified as either upright or not upright. In this case, if the sensed coordinate vector is not in the upright cone, posture state module 86 may determine whether the sensed coordinate vector is in a lying posture, either by testing the sensed coordinate vector against individual lying posture cones or testing the sensed coordinate vector against a generalized lying posture volume, such as a donut- or toroid-like volume that includes all of the lying postures, and may be defined using an angle or cosine range relative to the upright vector, or relative to a modified or virtual upright vector as will be described. In some cases, if lying postures are defined by cones, the lying volume could be defined as a logical OR of the donut- or toroid-like volume and the volumes of the lying posture cones. If the cones are larger such that some portions extend beyond the lying volume, then those portions can be added to the lying volume using the logical OR-like operation.

If the sensed coordinate vector resides within the donut- or toroid-like lying volume, then the sensed coordinate vector may be tested against each of a plurality of lying posture cones in the lying volume. Alternatively, the posture detection technique may not use lying cones. Instead, a posture detection technique may rely on a proximity test between the sensed coordinate vector and each of the reference coordinate vectors for the respective lying postures. The proximity test may rely on angle, cosine value or distance to determine which of the lying posture reference coordinate vectors is closest to the sensed coordinate vector. For example, the reference coordinate vector that produces the largest cosine value with the sensed coordinate vector as hypotenuse and the reference coordinate vector as adjacent is the closest reference coordinate vector. In this case, the lying posture associated with the reference coordinate vector producing the largest cosine value is the detected posture. Hence, there are a variety of ways to detect posture, such as using posture cones, using an upright posture cone with lying volume and lying posture cone test, or using an upright posture cone with lying volume and lying vector proximity test.

As a further illustration of an example posture detection technique, posture state module 86 may first determine whether patient 12 is generally in a lying posture state or upright posture state by analyzing the sensed coordinate vector in posture state space 152 with respect to an axis 153A for the upright posture state. Axis 153A may correspond to the upright reference coordinate vector. For example, angle "A" may be used to define upright posture cone 154, as described above, and angles "D" and "E" may be used to define the vector space in which patient 12 may be generally considered to be in the lying posture state, regardless of the particular posture state cone, e.g., lying front cone 158, lying back cone 156, lying right cone (not shown), or lying left cone (not shown), in which the sensed coordinate vector falls.

If it is determined that a sensed coordinate vector is not within an angle A of the axis 153A, then it may be determined that the patient is not in the upright posture indicated by the upright posture cone. In this case, it may next be determined whether a sensed coordinated vector is generally in a lying posture space volume, which may be considered somewhat donut- or toroid-like, and may be defined relative to the upright reference coordinate vector 153A. As shown, angles "D" and "E" define the minimum and maximum angle values, respectively, that a sensed vector may form with respect to axis 153A of patient 12 for a determination to be made that the patient is generally in the lying posture state. Again, cosine values may be used instead of angles to determine the positions of sensed coordinate vectors relative to posture cones or other posture volumes, or relative to reference coordinate vectors.

As illustrated, angles "D" and "E" may be defined with respect to vertical axis 153A (which may correspond to an upright reference coordinate vector), which is the reference coordinate vector for the upright posture cone, rather than with respect to a reference coordinate vector of a lying posture state cone. If a sensed vector is within the angular range of D to E, relative to axis 153A, then it can be determined by posture state module 86 that the patient is generally in a lying posture. Alternatively, in some examples, an angle C could be defined according to a generally horizontal axis 153C (which may correspond to one of the lying reference coordinate vectors). In this case, if a sensed vector is within angle C of axis 153C, it can be determined by posture state module 86 that the patient is in a lying posture. In each case, the region generally defining the lying posture state may be referred to as a posture donut or posture toroid, rather than a posture cone. The posture donut may generally encompass a range of vectors that are considered to be representative of various lying down postures.

As an alternative, posture state module 86 may rely on cosine values or a range of cosine values to define the posture donut or toroid with respect to axis 153A. When the sensed vector falls within the vector space defined by axis 153A and angles "D" and "E", or produces a cosine value with the reference coordinate vector 153A in a prescribed range, posture state module 86 may determine that patient 12 is generally in a lying posture state. For example, if the sensed vector and reference coordinate vector 153 produce a cosine value in a first range, the posture is upright. If the cosine value is in a second range, the posture is lying. If the cosine value is outside of the first and second ranges, the posture may be indeterminate. The first range may correspond to the range of cosine values that would be produced by vectors in posture cone 154 defined by angle A, and the second range may be correspond to cosine values that would be produced by vectors in the posture donut defined by angles D and E.

When the sensed vector fall within the vector space defined by axis 153A and angles "D" and "E", as indicated by angle or cosine value, posture state module 86 may then determine the particular lying posture state occupied by patient 12, e.g., lying front, lying back, lying right, or lying left. To determine the particular lying posture state occupied by patient 12, posture state module 86 may analyze the sensed vector with respect to reference coordinate vectors for individual lying posture state cones, e.g., lying front cone 156, lying back cone 158, lying right cone (not shown), and lying left cone (not shown), using one more techniques previously described, such as angle or cosine techniques. For example, posture state module 86 may determine whether the sensed coordinated vector resides within one of the lying posture state cones and, if so, select the posture state corresponding to that cone as the detected posture state.

FIG. 8C illustrates an example posture state space 155 that is a three-dimensional space substantially similar to posture state space 152 of FIG. 8B. Posture state space 155 includes upright posture cone 157 defined by reference coordinate vector 167. The tolerance that defines upright posture cone 157 with respect to reference coordinate vector 167 may include a tolerance angle or cosine value, as described above. In contrast to determining whether a sensed coordinate vector resides in a lying cone, FIG. 8C illustrates a method for detecting a lying posture based on proximity of a sensed coordinate vector to one of the reference coordinate vectors for the lying postures.

As shown in FIG. 8C, posture state space 155 includes four reference coordinate vectors 159, 161, 163, 165, which are associated with lying left, lying right, lying front, and lying back posture states, respectively. Posture state module 86 may have defined each of the four reference coordinated vector 159, 161, 163, 165 based on the output of one of more posture sensors while patient 12 occupied each of the corresponding posture states. Unlike lying front and lying back posture cones 158, 156 in the example of FIG. 8B, the posture state reference data for the four defined posture states corresponding to reference vectors 159, 161, 163, 165 need not include angles defined relative to the respective reference vector in a manner that defines a posture cone. Rather, as will be described below, the respective posture state reference vectors may be analyzed with respect to one another in terms of cosine values to determine which particular reference coordinate vector is nearest in proximity to a sensed coordinate vector.

In some examples, to determine the posture state of patient 12, posture state module 85 may determine whether a sensed coordinate vector is within upright posture cone 157 by analyzing the sensed coordinate vector in view of the tolerance angle or cosine value(s) defined with respect to upright posture reference coordinate vector 167, or whether the sensed vector is within a posture donut or toroid defined by a range of angles (as in FIG. 8B) or cosine values with respect to upright posture reference coordinate vector 167, in which case posture state module 86 may determine that patient 12 is in a general lying posture state.

If posture state module 86 determines that patient 12 is occupying a general lying posture state, posture state module 86 may then calculate the cosine value of the sensed coordinate vector with respect to each lying reference coordinate vectors 159, 161, 163, 165. In such a case, posture state module 86 determines the particular lying posture state of patient 12, i.e., lying left, lying right, lying front, lying back, based on which cosine value is the greatest of the four cosine values. For example, if the cosine value calculated with the sensed vector as the hypotenuse and the lying front reference vector 163 as the adjacent vector is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

In some examples, posture state module 86 may determine whether patient 12 is generally in a lying posture state based on the relationship of a sensed vector to upright reference vector 167. For example, as described above, a lying posture donut or toroid may be defined with respect to upright posture reference vector 167, e.g., using angles D and E as in FIG. 8B. Such a technique may be appropriate when lying posture reference vectors 159, 161, 163, 165 define a common plane substantially orthogonal to upright posture reference vector 167. However, the lying posture reference vectors 159, 161, 163, 165 may not in fact be orthogonal to the upright reference coordinate vector 167. Also, the lying posture reference vectors 159, 161, 163, 165 may not reside in the same plane.

To account for non-orthogonal reference vectors, in other examples, a lying posture donut or toroid may be defined with respect to a modified or virtual upright reference vector 169 rather than that actual upright posture reference vector 167. Again, such a technique may be used in situations in which the lying reference vectors 159, 161, 163, 165 are not in a common plane, or the common plane of reference vector 159, 161, 163, 165 is not substantially orthogonal to upright reference vector 167. However, use of the example technique is not limited to such situations.

To define virtual upright reference vector 169, posture state module 86 may compute the cross-products of various combinations of lying reference vectors 159, 161, 163, 165 and average the cross product values. In the example of FIG. 8C, posture state module 86 may compute four cross products and average the four cross product vectors to yield the virtual upright vector. The cross product operations that may be performed are: lying left vector 159×lying back vector 165, lying back vector 165×lying right vector 161, lying right vector 161×lying front vector 163, and lying front vector 163×lying left vector 159. Each cross product yields a vector that is orthogonal to the two lying reference vectors that were crossed. Averaging each of the cross product vectors yields a virtual upright reference vector that is orthogonal to lying plane 171 approximately formed by lying reference vectors 159, 161, 163, 165.

Using virtual upright reference vector 169, posture state module 86 may define a lying posture donut or toroid in a manner similar to that described with respect to upright reference vector 167, but instead with respect to virtual upright reference vector 169. In particular, when posture state module 86 determines that the patient is not in the upright posture, the posture state module determines whether the patient is in a lying posture based on an angle or cosine value with respect to the virtual upright reference vector 169.

Posture state module 86 may still determine whether patient 12 is in an upright posture state using upright posture cone 157. If posture state module 86 determines that patient 12 is occupying a general lying posture state based on the analysis of the sensed coordinate vector with respect to virtual upright reference vector 169, posture state module 86 may then calculate the cosine value of the sensed coordinate vector (as hypotenuse) with respect to each lying reference coordinate vectors 159, 161, 163, 165 (as adjacent).

In such a case, posture state module 86 determines the particular lying posture state of patient 12, i.e., lying left, lying right, lying front, lying back, based on which cosine value is the greatest of the four cosine values. For example, if the cosine value calculated with the lying front reference vector 163 is the largest value of the four cosine values, the sensed vector may be considered closest in proximity to lying front reference vector out of the four total reference vectors 159, 161, 163, 165. Accordingly, posture state module 85 may determine that patient 12 is occupying a lying front posture state.

Additionally, posture state definitions are not limited to posture cones. For example, a definition of a posture state may involve a posture vector and a tolerance, such as a maximum distance from the posture vector. So long as a detected posture vector is within this maximum distance from the posture vector that is included in the definition of the posture state, patient 12 may be classified as being in that posture state. This alternative method may allow posture states to be detected without calculating angles, as is exemplified above in the discussion related to posture cones.

Further to the foregoing, posture states may be defined that are specific to a particular patient's activities and/or profession. For instance, a bank teller may spend a significant portion of his working day leaning forward at a particular angle. A patient-specific "Leaning Forward" posture state including this angle may be defined. The cone angle or other tolerance value selected for this posture state may be specific to the particular posture state definition for this patient. In this manner, the defined posture states may be tailored to a specific user, and need not be "hard-coded" in the IMD.

In some examples, individual posture states may be linked together, thereby tying posture states to a common set of posture reference data and a common set of therapy parameter values. This may, in effect, merge multiple posture cones for purposes of posture state-based selection of therapy parameter values. For example, all lying posture state cones (back, front, left, right) could be treated as one cone or a donut/toroid, e.g., using a technique the same as or similar to that described with respect to FIGS. 8B and 8C to define a donut, toroid or other volume. One program group or common set of therapy parameter values may apply to all posture states in the same merged cone, according to the linking status of the posture states, as directed via external programmer 20.

Merging posture cones or otherwise linking a plurality of posture states together may be useful for examples in which a common set of therapy parameter values provides efficacious therapy to patient 12 for the plurality of posture states. In such an example, linking a plurality of posture states together may help decrease the power consumption required to provide posture-responsive therapy to patient 12 because the computation required to track patient posture states and provide responsive therapy adjustments may be minimized when a plurality of posture states are linked together.

Linking of posture states also may permit a therapy parameter value adjustment in one posture state to be associated with multiple posture states at the same time. For example, the same amplitude level for one or more programs may be applied to all of the posture states in a linked set of posture states. Alternatively, the lying down posture states may all reside within a "donut" or toroid that would be used instead of separate comes 156 and 158, for example. The toroid may be divided into sectional segments that each correspond to different posture states, such as lying (back), lying (front), lying (right), lying (left) instead of individual cones. In this case, different posture reference data and therapy parameter values may be assigned to the different sectional segments of the toroid.

Figure 9:
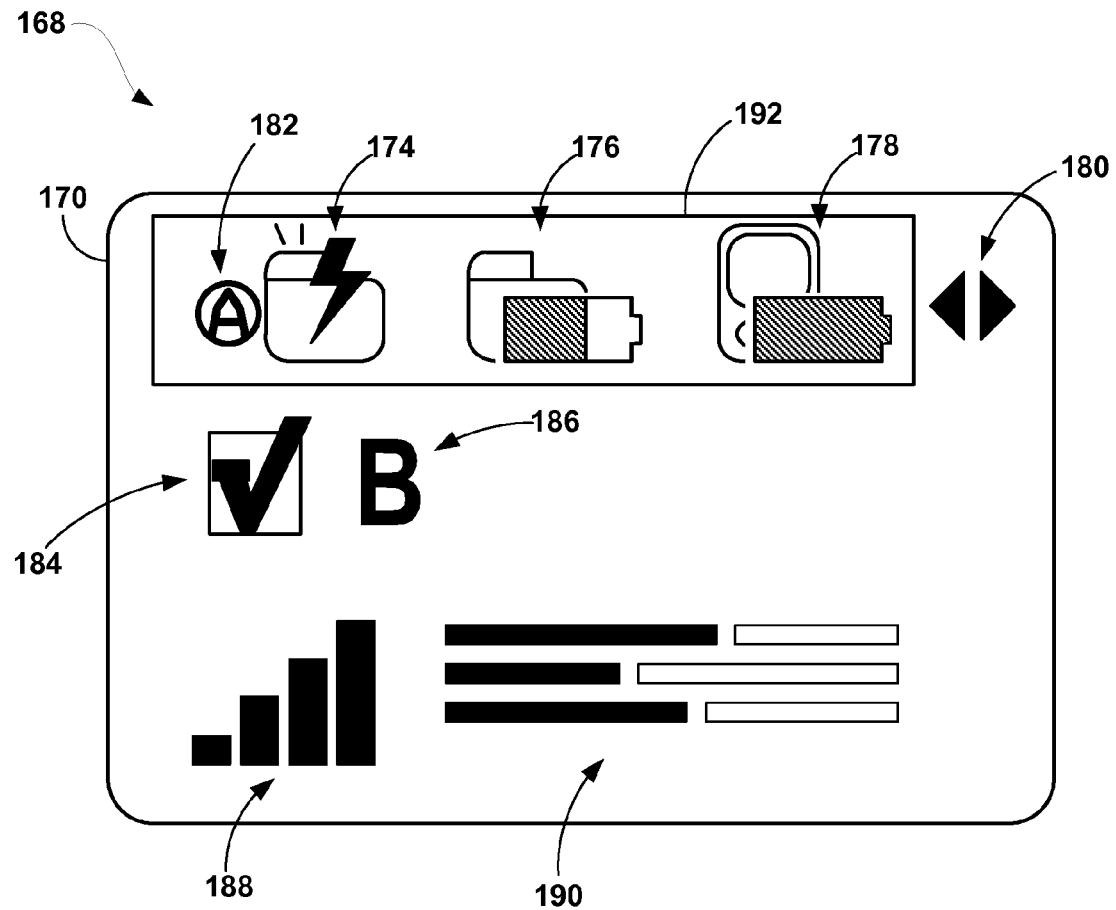
FIG. 9 is a conceptual diagram illustrating an example user interface of a patient programmer for delivering therapy information to the patient.

FIG. 9 is a conceptual diagram illustrating an example user interface 168 of a patient programmer 30 for delivering therapy information to patient 12. In other examples, a user interface similar to user interface 168 may also be presented by clinician programmer 60. In the example of FIG. 9, display 36 of patient programmer 30 provides user interface 168 to the user, such as patient 12, via screen 170. Screen 170 includes stimulation icon 174, IMD battery icon 176, programmer battery icon 178, navigation arrows 180, automatic posture response icon 182, group selection icon 184, group identifier 186, program identifier 188, amplitude graph 190, and selection box 192. User interface 168 provides information to patient 12 regarding group, program, amplitude, and automatic posture response status. User interface 168 may be configurable, such that more or less information may be provided to patient 12, as desired by the clinician or patient 12.

Selection box 192 allows patient 12 to navigate to other screens, groups, or programs using navigation arrows 180 to manage the therapy. In the example, of screen 170, selection box 192 is positioned so that patient 12 may use arrows 44 and 48 (FIG. 2) of control pad 40 of programmer 30 to move to the automatic posture response screen, the volume screen, the contrast or illumination screen, the time screen, and the measurement unit screen of patient programmer 30. In these screens, patient 12 may be able to control the use of the automatic posture response feature and adjust the patient programmer 30 features. Patient 12 may only adjust the features surrounded by selection box 192.

Group identifier 186 indicates one of possibly several groups of programs that can be selected for delivery to patient 12. Group selection icon 184 indicates whether the displayed group, e.g., group B in FIG. 9, is actually selected for delivery to patient 12. If a presently displayed group is selected, group selection icon 184 includes a box with a checkmark. If a presently displayed group is not selected, group selection icon 184 includes a box without a checkmark. To navigate through the stored program groups, a user may use control pad 40 to move selection box 192 to select the group identifier 186 and then use control pad 40 to scroll through the various groups, e.g., A, B, C, and so forth. IMD 14 may be programmed to support a small number of groups or a large number of groups, where each group contains a small number of programs or a large number of programs that are delivered simultaneously, in sequence, or on a time-interleaved basis.

For each group, group selection icon 184 indicates the appropriate status. For a given group, program identifier 188 indicates one of the programs associated with the group. In the example of FIG. 9, no program number is indicated in program identifier 188 because all of the programs' amplitudes are shown in each bar of amplitude graph 190. Solid portions of the bars indicate the relative amplitude IMD 14 currently is using to deliver stimulation therapy to patient 12, while open portions of the bars indicate the remaining amplitude available to each program. In some examples, numerical values of each program's amplitude may be show in addition to or in place of amplitude graph 190. In other examples of user interface 168 specific to drug delivery using IMD 26, amplitude graph 190 may show the flow rate of drugs or frequency of bolus delivery to patient 12. This information may be show in numerical format as well. Patient 12 may encompass group selection icon 184 with selection box 192 to scroll between the different programs of the selected group.

Automatic posture response icon 182 indicates that IMD 14 is generally activated, such that processor 80 automatically modifies therapy to patient 12 based upon the posture state detected by posture state module 86. In particular, automatic posture responsive therapy may involve adjusting one or more therapy parameter values, selecting different programs or selecting different program groups based on the detected posture state of the patient. However, automatic posture response icon 182 is not present next to group identifier 186, indicating that group "B" does not have automatic posture responsive therapy activated for any of the programs within group "B."

Some groups or individual programs in groups may support automatic posture responsive therapy. For example, automatic adjustment of one or more therapy parameter values in response to posture state indication may be selectively activated or deactivated based on settings entered by a clinician, or possibly patient 12. Hence, some programs or groups may be configured for use with posture responsive therapy while other programs or groups may not be configured for use with posture responsive therapy. In some cases, if posture responsive therapy supported by the automatic posture response feature is desired, patient 12 may need to switch therapy to a different group that has automatic posture responsive therapy activated for IMD 14 to adjust therapy according to the patient 12 posture state.

Figure 10:
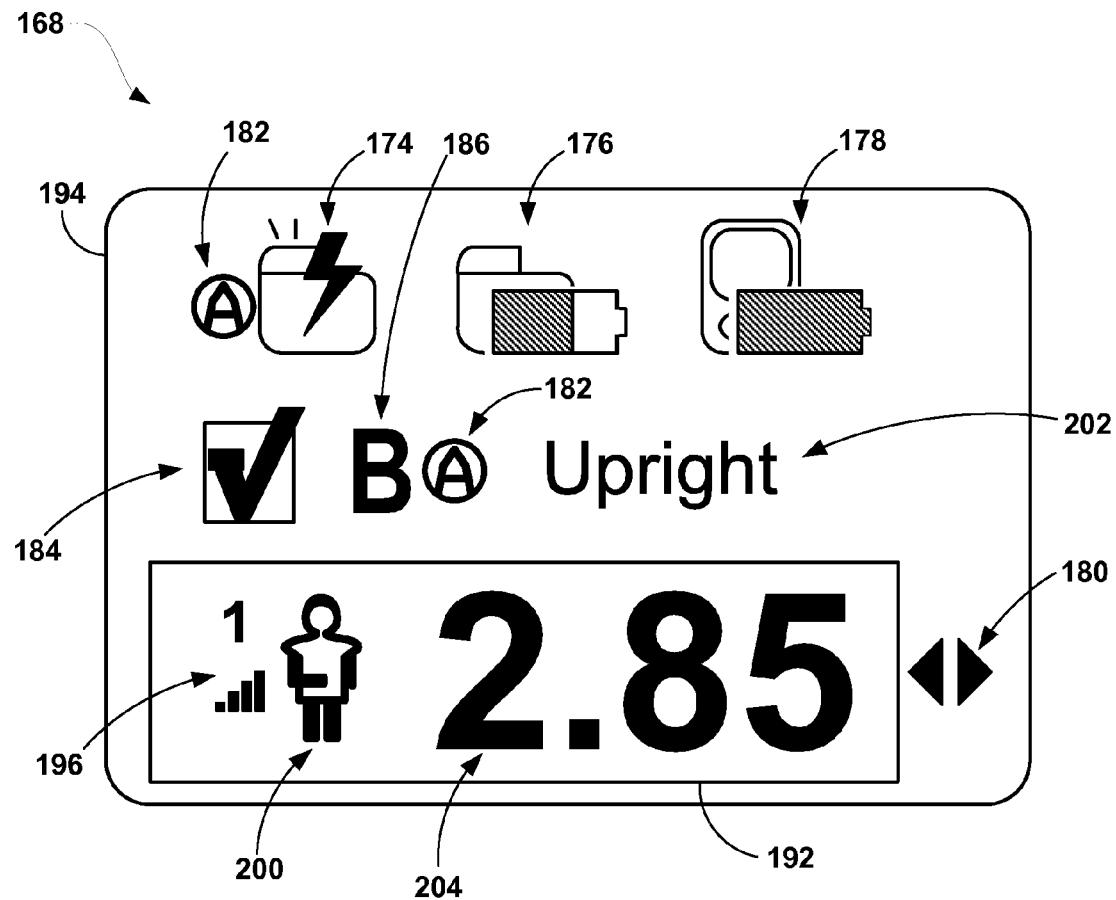
FIG. 10 is a conceptual diagram illustrating an example user interface of a patient programmer for delivering therapy information that includes posture information to the patient.

FIG. 10 is a conceptual diagram illustrating an example user interface 168 of a patient programmer 30 for delivering therapy information that includes posture information to the patient. In other examples, user interface 168 may also be shown on clinician programmer 60. In the example of FIG. 10, display 36 of patient programmer 30 provides user interface 168 to the user, such as patient 12, via screen 194. Screen 194 includes stimulation icon 174, IMD battery icon 176, programmer battery icon 178, and automatic posture response icon 182, similar to screen 170 of FIG. 9. In addition, screen 194 includes group selection icon 184, group identifier 186, supplementary posture state indication 202, program identifier 196, posture state indication 200, amplitude value 204, selection box 192, and selection arrows 180. User interface 168 provides information to patient 12 regarding group, program, amplitude, automatic posture response status, and posture state information. More or less information may be provided to patient 12, as desired by the clinician or the patient.

Group identifier 186 indicates that group "B" is active, and automatic posture response icon 182 indicates group "B" (containing one or more programs) is activated to allow IMD 14 to automatically adjust therapy according to the patient 12 posture state. In the example shown in FIG. 10, user interface 168 indicates the posture state determined by IMD 14, e.g., via posture state indication 200 and supplementary posture state indication 202. Program identifier 196 illustrates that information regarding program "1" of group "B" is displayed on screen 194, such as amplitude value 204 illustrating the current voltage amplitude of program "1" is 2.85 Volts. Patient 12 may scroll through different programs of the group by using navigation arrows 180 via arrows 44 and 48 of control pad 40.

In addition, posture state indication 200 shows that IMD 14 is detecting that patient 12 is in the upright or standing posture based on the output of posture state module 86 (FIG. 4). Supplementary posture state indication 202 supplements posture state indication 200 by explaining in words to patient 12 the exact posture being detected by posture state module 86 of IMD 14. Posture state indication 200 and supplementary posture state indication 202 presented via user interface 168 change according to the sensed, or detected, posture state detected by IMD 14. The posture state may be communicated to the external programmer immediately after IMD 14 detects a posture change, or communicated periodically or non-periodically by IMD 14 unilaterally or upon receiving a request from the programmer. Accordingly, the posture state indication 200 and/or supplementary posture state indication 202 may represent a current, up-to-the minute status, or a status as of the most recent communication of posture state from IMD 14. Posture state indication 200 is shown as a graphical representation, but the posture state indication may alternatively be presented as any one of a symbolic icon, a word, a letter, a number, an arrow, or any other representation of the posture state. In some cases, posture state indication 200 may be presented without supplementary posture state indication 202.

Selection box 192 indicates that patient 12 view other programs within group "B" using selection arrows 180. Selection box 192 may be moved to select other screen levels with control pad 40 (FIG. 2) of patient programmer 30 in order to navigate through other stimulation groups or adjustable elements of the therapy. When patient 12 selects a different program with control pad 40, program identifier 196 is updated to correctly identify the current program viewed on screen 194.

In addition to graphical, textual or other visible indications of posture state, the external programmer may present audible and/or tactile indications of posture state via any of a variety of audible or tactile output media. An audible indication may be spoken words stating a posture state, or different audible tones, different numbers of tones, or other audible information generated by the programmer to indicate posture state. A tactile indication may be, for example, a somatosensory indication, such as a different numbers of vibratory pulses delivered in sequence or vibratory pulses of different lengths, amplitudes, or frequencies.

As previously described, some examples of the disclosure relate to techniques for automatically modifying stimulation therapy based on posture state of a patient, e.g., by adjusting one or more stimulation parameters according to a modification profile that varies according to a type of posture state transition undertaken by the patient. For some posture state transitions, therapy parameter value modifications may be performed gradually, rather than by immediately changing the parameter value. For example, based on the detected posture state transition of a patient, an IMD may ramp-up and/or ramp-down a stimulation parameter value during a transition period to a desirable parameter value from the value previously programmed to be delivered. Either the ramp rate or the transition period may be defined by a modification profile. Alternatively, for other posture state transitions such as upright to lying down, the IMD may immediately drop a parameter value, e.g., voltage amplitude, to a lower value. In this manner, the IMD may reduce the likelihood that the patient will experience discomfort as a result of the posture state transition.

A modification profile may indicate the manner in which IMD 14 detects a posture transition and modifies therapy in response to the detected posture transition. The modification profile may define a dwell time to define a duration of time between the detection of a posture state transition or the actual posture state transition and the activation of a change in a parameter such as amplitude to adjust therapy to accommodate the posture state transition. During a dwell time period, IMD 14 detects the posture transition by patient 12 and imposes a delay period before modifying therapy delivery. A transition period indicates a duration of time over which IMD 14 transitions between a first therapy program (or therapy parameter settings) associated with a first patient posture state and a second therapy program associated with a second, detected patient posture state. A ramp rate indicates the rate of change with which IMD 14 switches between therapy parameter values based on a particular posture state transition.

In some examples, however, a modification profile does not include a ramp rate and/or a transition time. For example, IMD 14 may implement a ramp rate or transition time that is independent of the posture state transition. In such examples, the ramp rate or transition time may be selected based on whether the stimulation parameter value (e.g., amplitude) is increasing or decreasing in response to a detected posture state transition. For example, a ramp rate and/or transition time may be shorter if the stimulation parameter value is decreased in response to a detected posture state transition compared to if the stimulation parameter value is increased.

Modification profiles may define the manner in which IMD 14 switches between therapy programs, e.g., in response to a detected posture state transition. A clinician may program the modification profiles, such as by selecting the durations of time for the dwell time and selecting either the transition time or ramp rate with which IMD 14 shifts between therapy parameter values. Either the ramp rate or transition period may remain variable and the other may remain fixed. For example, in some examples, the ramp rate is a predetermined and fixed value, and the transition period depends upon the ramp rate and the net increase or decrease to a therapy parameter value. As another example, the transition period may be predetermined and fixed, and the ramp rate may depend upon the met increase or decrease to a therapy parameter value and the fixed transition period over which the increase or decrease takes place. In some examples, the transition period may be fixed and the ramp rate may not be a constant value. Therapy delivery according to the modification profile, however, is not implemented by IMD 14 when IMD 14 is in a programming mode because the posture responsive therapy features of IMD 14 are deactivated. That is, when IMD 14 is not providing posture responsive therapy, IMD 14 does not automatically switch between therapy programs according to the modification profile to accommodate different patient postures.

Figure 11A:
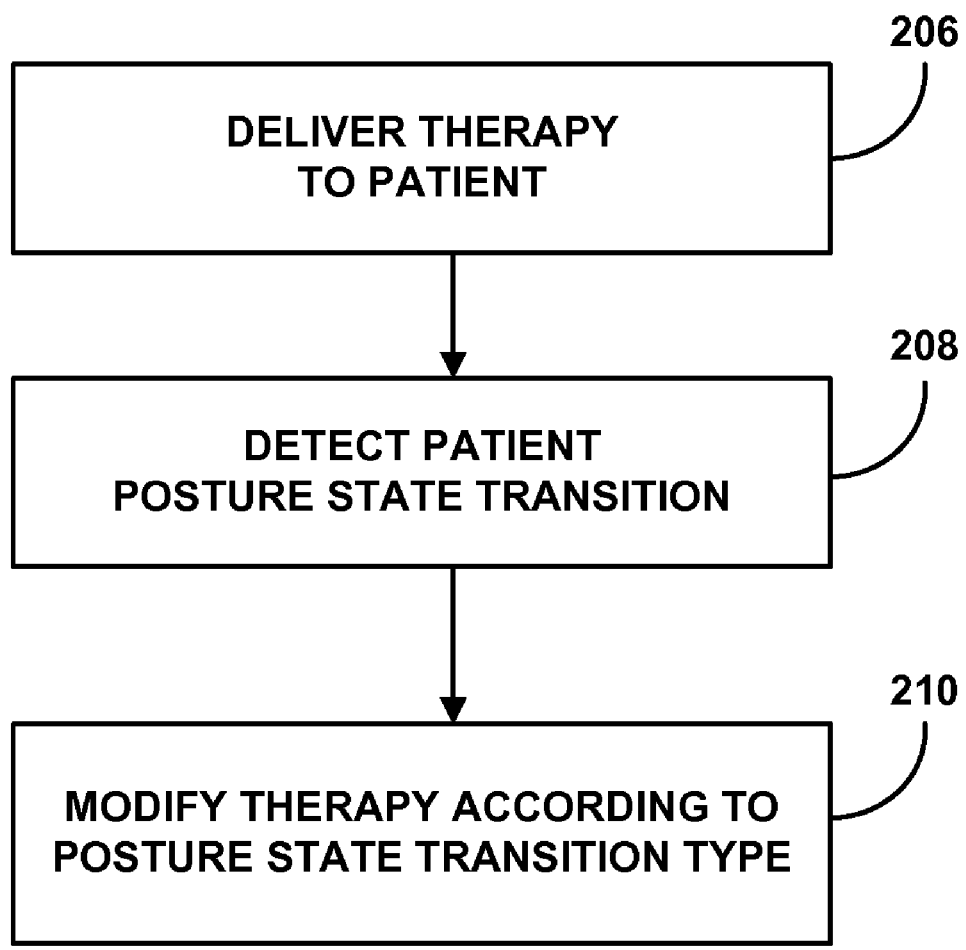
FIGS. 11A and 11B are flowcharts illustrating example techniques for modifying stimulation therapy based on patient posture state transitions.
Figure 11B:
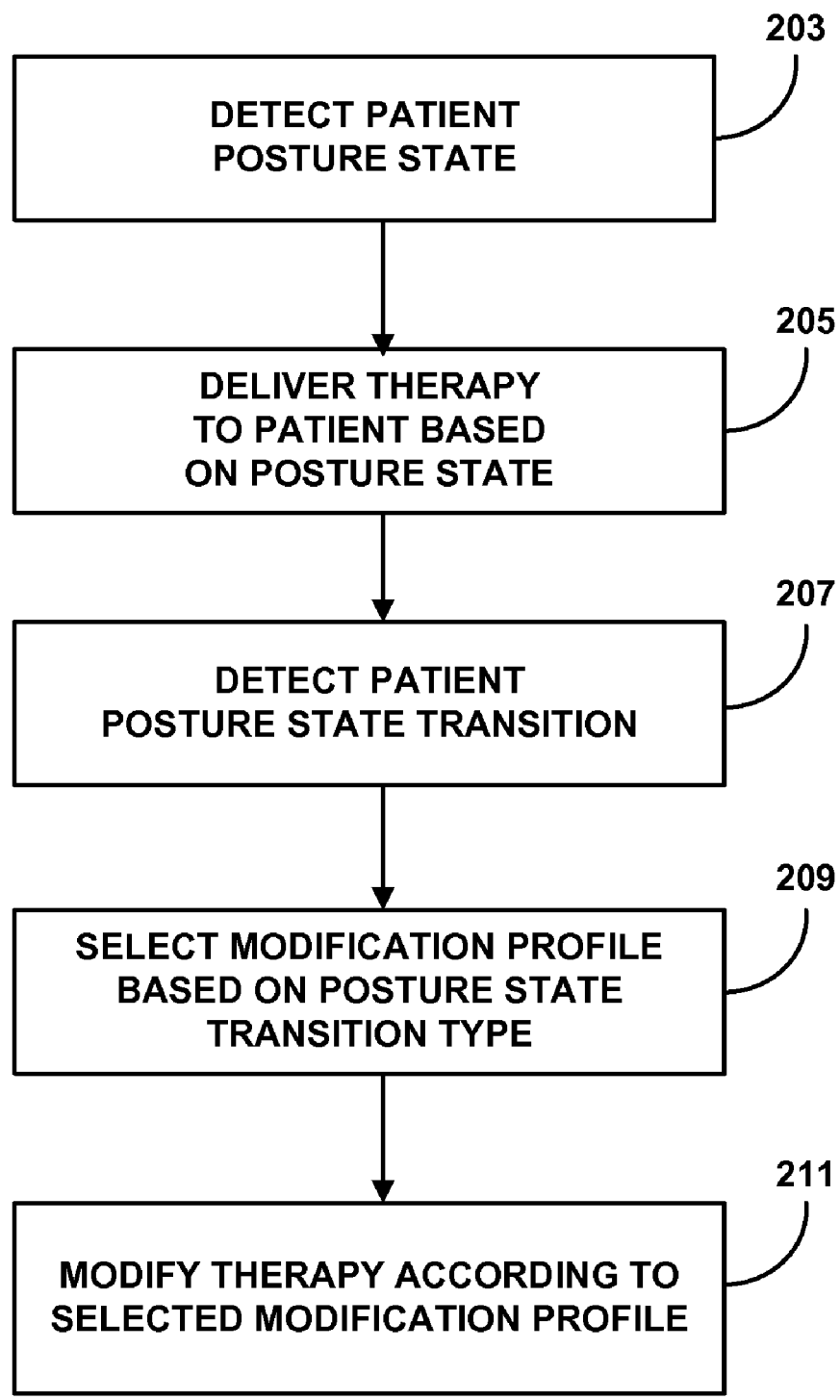

FIGS. 11A and 11B are flowcharts illustrating example techniques for modifying stimulation therapy based on patient posture state transitions. For purposes of illustration, the example techniques will be described with respect to implantable stimulation system 10 described herein. However, such a technique may be implemented by any suitably configured system utilized to provide electrical stimulation therapy to a patient, such as, e.g., implantable stimulation system 22 described herein. Further, utilization of such an example technique is not limited to electrical stimulation therapy. Rather, in some example, such a technique may be implemented in other patient therapy systems, including those configured to provide drug delivery therapy, e.g., implantable drug delivery system 24 described herein.

Referring to FIG. 11A, processor 80 of IMD 14 controls stimulation generator 84 (FIG. 4) to generate and deliver therapy to a patient (206), e.g., in the form of electrical stimulation pulses delivered to patient 12 via stimulation leads 16A and 16B (206). As previously described, the electrical stimulation therapy may be provided to patient 12 according to one or more stimulation programs. Accordingly, stimulation generator 84, under the control of processor 80, may generate stimulation pulses having parameters values for stimulation parameters defined by one or more stimulation programs.

The specific parameter values defined by the stimulation programs may be appropriate for a posture state of patient 12 detected via posture state module 86. Thus, upon detection of the posture state by posture state module 86 (FIG. 4), processor 80 may control stimulation generator 84 to generate and deliver therapy to patient 12 according to the one or more therapy programs associated with the detected posture state. In some examples, the associations between therapy programs and patient posture states are stored by memory 82 of IMD 14. In one example of posture responsive therapy delivery, if processor 80 of IMD 14 detects that patient 12 is lying down via posture state module 86, processor 80 controls stimulation generator 84 according to the corresponding stimulation program to generate and deliver stimulation signals in accordance with the therapy program associated with the lying down state. In this way, IMD 14 delivers a stimulation signal having a stimulation amplitude and/or other parameters that are appropriate for patient 12 when lying down.

While providing therapy to patient 12, IMD 14 may detect a patient posture state transition (208). Based on the type of posture state transition, IMD 14 modifies therapy (210). In particular, IMD 14 may modify stimulation using a modification profile that corresponds to the patient posture state transition detected by the posture state module. For example, if the posture state transition is from an upright posture state to a lying down posture state, for example, IMD 14 may apply a modification profile that immediately drops the amplitude of the stimulation from an existing level to a desired level. A plurality of posture state definitions and associated modification profiles may be stored in memory 82 of IMD 14. If the posture state transition is from a lying state to another lying state, from an upright state to another upright state, or from a lying state to an upright state, IMD 14 may apply a modification profile that ramps amplitude upward or downward according to a more gradual ramp profile. However, ramp characteristics such as timing, slope or the like may vary according to the particular posture state transition that is detected and/or the type of parameter value being modified. For example, different posture state transitions may dictate different modification profiles.

Hence, based on the detected posture state transition, IMD 14 automatically modifies the stimulation therapy based on a posture state transition (210). In the case of stimulation therapy, processor 80 modifies therapy delivery from a set of therapy parameter values (e.g., a therapy program) configured for delivery to patient 12 in one posture state to a set of stimulation therapy parameter values configured for delivery to patient 12 when in another posture state. Processor 80 of IMD 14 applies a modification profile that controls the way in which the modification is made, e.g., immediate drop or gradual ramp. As an example, if a stimulation program appropriate for patient 12 when standing defines an amplitude of Y volts, and the stimulation program appropriate for patient 12 when lying down defines an amplitude of X volts, then the modification profile determines the manner in which amplitude is modified from Y to X or X to Y. In other examples, the amplitude of stimulation therapy may be a current amplitude (e.g., amps), or defined in terms of energy (e.g., Coulombs).

To modify the electrical stimulation therapy as described, e.g., for a transition from lying down to upright, processor 80 controls stimulation generator 84 such that the amplitude of stimulation provided to patient 12 increases in value from X volts to Y volts. However, the adjustment from X volts to Y volts does not occur substantially immediately, but instead may be gradually adjusted (e.g., ramped up or down) over a ramp period. During the ramp period, processor 80 controls stimulation generator 84 such that the stimulation amplitude value may be ramped up from a value of X volts to a value of Y volts over a transition period of n seconds. For example, processor 80 may control stimulation generator 84 such that the amplitude value of the stimulation provided to patient 12 is increased at a constant rate, starting at X volts and ending at Y volts. In other examples, a rate that is not constant may be used to adjust the amplitude value.

For a transition from upright to lying down, however, processor 80 controls stimulation generator 84 to substantially immediately drop the amplitude from Y volts to X volts. In this case, the substantially immediate drop in amplitude represents a modification profile that is different from a modification profile in which the amplitude is gradually ramped. Using such a technique, IMD 14 may modify stimulation therapy to patient 12 based on the posture state transition of patient 12 by adjusting one or more stimulation parameter values by ramping from a first programmed amplitude value to a second programmed amplitude value. Although the modification profile is generally described in terms of the rate of change of a therapy parameter value from an existing value to a desired, target value, another aspect of a modification profile may include a dwell time that precedes activation of the modification, as described in further detail with reference to FIG. 12 below.

FIG. 11B illustrates a technique for modifying stimulation therapy based on patient posture state transitions in greater detail. As shown in FIG. 11B, upon detecting a patient posture state (203), processor 80 controls stimulation generator 84 to deliver stimulation to a patient based on the posture state (205). In particular, processor 80 adjusts therapy by adjusting one or more therapy parameters or selecting one or more different programs or groups based on the posture state occupied by the patient, e.g., upright, upright and active, lying (front), lying (back), lying (right), lying (left). Lying (front), lying (back), lying (right) and lying (left) posture states refer to postures states in which the patient is lying down on his front, back, right side or left side, respectively.

Upon detecting a patient posture state transition (207), processor 80 modifies therapy according to the new posture state. Processor 80 selects a modification profile based on the type of the posture state transition (209). The modification profiles may be stored by memory 82 of IMD 14 or a memory of another device, such as programmer 20. Examples of different posture state transition types include upright to upright and active, upright and active to upright, upright to different lying down posture states, upright and active to different lying down posture states, different lying down postures states to upright or upright and active, or a transition between different lying down posture states.

Modification profiles may be stored as modification profile data for all or a subset of the transition types, and may define a dwell time, and a ramp rate and/or transition period, and, in some cases, other characteristics to be implemented in the modification, or any combination thereof. In some examples, the modification profile does not include either or both the ramp rate and transition period. As previously indicated, IMD 14 may implement a ramp rate and/or transition time that are independent of the posture state transition. For example, the ramp rate or transition time may be selected based on whether the stimulation parameter value (e.g., amplitude) is increasing or decreasing in response to a detected posture state transition. Upon selection of the appropriate modification profile for the detected posture state transition (209), processor 80 modifies therapy according to the selection modification profile (211). The ramp rate, transition period, dwell time or the like may differ for different posture state transitions, depending on the modification profiles associated with the posture state transitions. For example, a transition from upright to upright and active may require a relatively gradual up-ramp, whereas a transition from upright to a lying down posture state may require an abrupt down-ramp to quickly change amplitude.

Table 1 below illustrates an example of different modification profiles associated with different posture state transition types.

TABLE 1

| POSTURE STATE TRANSITION | MODIFICATION PROFILE |
| --- | --- |
| Upright to Active and Upright | 1 |
| Upright to Lying (Front) | 2 |
| Upright to Lying (Back) | 3 |
| Upright to Lying (Right) | 4 |
| Upright to Lying (Left) | 5 |
| Upright and Active to Upright | 6 |
| Upright and Active to Lying (Front) | 7 |
| Upright and Active to Lying (Back) | 8 |
| Upright and Active to Lying (Right) | 9 |
| Upright and Active to Lying (Left) | 10 |
| Lying (Front) to Upright | 11 |
| Lying (Front) to Upright and Active | 12 |
| . . . | |
| Lying (Left) to Lying (Right) | 30 |

In some examples, posture state module 86 of IMD 14 detects six different posture states, and there may be up to thirty different posture state transitions between those six posture states. Each modification profile shown in Table 1 above may be unique in the sense that it defines different rates of change, transition periods, dwell times, or the like. Alternatively, some of the modification profiles may be the same for different posture state transition types. For example, transitions to or from any of the lying down posture states could have the same modification profiles.

Figure 12:
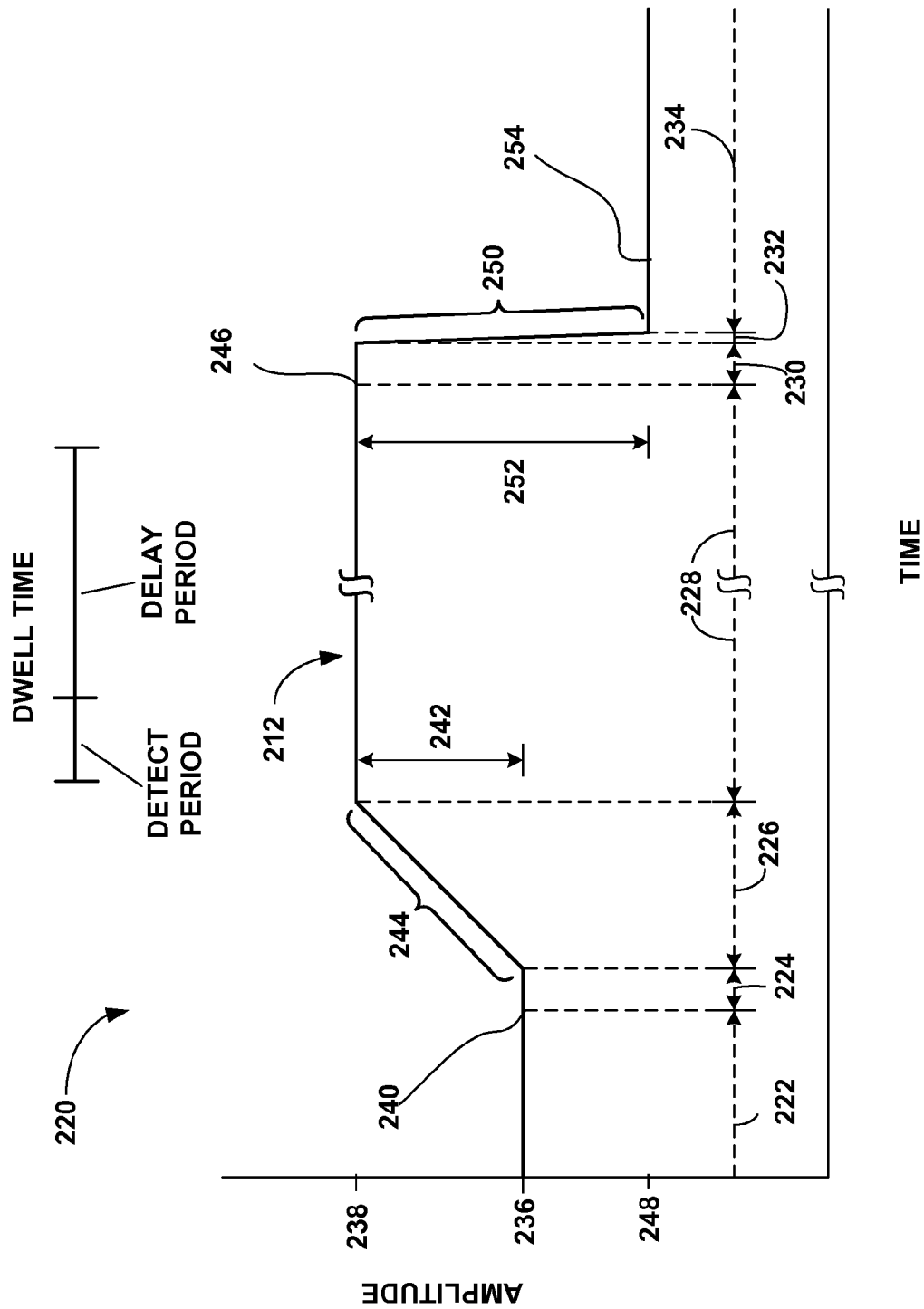
FIG. 12 is a plot illustrating the amplitude value of an example stimulation therapy provided to a patient over a period of time.

FIG. 12 is a plot 220 illustrating the amplitude value of an example stimulation therapy provided to patient 12 over a period of time. Plot 220 includes a line 212 that represents the amplitude value of stimulation pulses being delivered, e.g., by IMD 14, as part of stimulation therapy provided to patient 12 with respect to time. In the example illustrated, the stimulation therapy may be automatically modified based on the posture state of patient 12 detected by posture state module 86 (FIG. 4) of IMD 14. The modification may have a modification profile, e.g., slow ramp, medium ramp, fast ramp, or immediate increase or decrease, which varies according to the posture state transition. As one example, plot 220 may be representative of the amplitude value of stimulation therapy delivered in part according to a technique similar to that described with respect to FIGS. 11A and 11B.

As indicated by FIG. 12, the variable of time is represented along the horizontal axis of plot 220 and the variable of amplitude is represented along the vertical axis of plot 220. As previously noted, amplitude may refer to current amplitude or voltage amplitude of stimulation signals. In addition, for purposes of illustration, the time variable of plot 220 has been divided into time periods 222, 224, 226, 228, 230, 232, and 234. During time period 222, patient 12 may occupy a posture state which can be characterized as upright, and is detected by IMD 14 as such. Accordingly, processor 80 of IMD 14 controls stimulation generator 84 to provide patient 12 with stimulation therapy to effectively address symptoms experienced by patient 12 while upright. For example, processor 80 may select a therapy program from memory 82 that is associated with the upright posture and is believed to provide efficacious therapy to patient 12 in the upright posture. In the example shown, the amplitude parameter of such stimulation therapy is provided at a first amplitude value 236.

In the example shown in FIG. 12, patient 12 maintains the upright posture state until time 240, at which time patient 12 begins to walk. At this time, the posture state transitions from upright to upright and active. The upright and active posture state may correspond to a stimulation therapy program specifying a modification of the amplitude parameter to second amplitude value 238. In addition, the transition from upright to upright and active corresponds to a modification profile characterized by a ramp 244 and/or dwell time period 244. As indicated by FIG. 12, second amplitude value 238 is greater than first amplitude value 236 by approximately the amount represented by line 242.

According to plot 220, patient 12 continues to walk throughout time periods 224, 226, and 228. However, as indicated by plot 220, IMD 14 may not immediately respond to the posture transition of patient 12 from upright to upright and active. Instead, during a dwell time period 224, processor 80 detects the posture transition by patient 12, and imposes a delay period before adjusting therapy delivery. For example, during dwell time period 224, processor 80 may process information received from posture state module 86 using instructions stored in memory 82 to detect that patient 12 has transitioned from upright to upright and active. Dwell time 224 may be defined by the modification profile corresponding to the posture state transition from an upright posture state to upright and active posture state.

In some examples, dwell time period 224 may represent a duration of time between the detection of a posture state transition and the activation of a change in a parameter such as amplitude, while in other examples, dwell time period 224 represents a duration of time between the actual posture state transition and the adjustment to the therapy. Dwell time period 224 may be a part of a modification profile that is associated with the posture state transition. This duration of time may be referred to as a dwell time, which may be a combination of a detection period and a delay period, e.g., as shown in FIG. 12. The length of the detection period may depend on parameters and sampling frequency with which posture state module 86 detects a posture state. The detection period generally refers to a period of time during which a posture state detection has reached a reliable, steady state indication of posture state. The detection period should be relatively short to provide accurate and responsive posture detection performance.

The delay period may be user defined, and, in the example shown in FIG. 12, is longer than the detection period. The dwell time period 224 is a period of delay that occurs prior to ramping the amplitude to the posture-specific amplitudes (or other stimulation parameter) for the programs in a group. Some patients may not experience increased or decrease symptoms, such as pain, until they have been in a posture for an extended period of time. The delay period aspect of the dwell time accounts for these patient considerations.

Once it is determined that a posture state transition has occurred following a detection period of the posture state, and the delay period of the dwell time has expired, processor 80 controls stimulation generator 84 to begin adjusting the amplitude level from a first amplitude level associated with the previous posture state, e.g., upright, to a second amplitude level associated with the newly detected posture state, e.g., upright and active. In some examples, the modification to the stimulation amplitude is performed according to a parameter defined by the modification profile associated with the posture state transition from the upright posture state to the upright and active posture state.

Although plot 220 indicates dwell time periods 224 and 230 (which is described below) are significant amounts of time relative to the duration of therapy delivery, in some examples, the relative amount of the detection period required to detect the posture transition of patient 12 may be minimal compared to the duration of therapy delivery, such that it is relatively insignificant for the purposes of the described technique. For example, the amount of time required for a detection period may be on the order of seconds, milliseconds or less depending on the technique used to detect the posture state of a patient. In some examples, the amount of time required for a detection period may be less than or equal to 1 second. For example, the amount of time required for a detection period may range from approximately 100 milliseconds to approximately 1 second, such as 300 milliseconds to 400 milliseconds.

The length of the delay period may be user defined to be different for different posture state transitions. Hence, the total duration of the dwell time for a transition from upright to upright and active may be different than the dwell time for a transition from upright and active to lying down. The dwell time represented by time periods 224 and 230 may be fixed for all posture state transitions or vary for different posture state transition types, e.g., according to user defined time periods. In some examples, the length of one or more dwell times may be programmed by a user such as a patient or clinician, e.g., using one or more of programmers 20, 30 and 60 to program IMD 14 as previously described.

In some examples, the duration of a delay time period may be on the order of seconds, while in other examples the duration of a delay time period may be on the order of minutes. For example, for posture state transitions to an upright posture state, the length of a delay time period may range from approximately one second to approximately five minutes, such as approximately five seconds to approximately 60 seconds. As another example, for posture state transitions to a lying posture state, the duration of the delay time period may range from approximately 0 seconds to approximately 2 minutes, such as approximately 0 seconds to 10 seconds. As another example, for posture state transitions to an upright and active, e.g., walking, the duration of a delay time period may range from approximately 10 seconds to approximately 10 minutes, such as approximately 30 seconds to approximately five minutes, such as approximately two minutes to approximately five minutes.

In the example of FIG. 12, once IMD 14 has detected a posture transition of patient 12 from upright to upright and active, IMD 14 may automatically adjust the stimulation therapy, e.g., to effectively address the symptoms experienced by patient 12 while walking. As illustrated by line 212, the stimulation therapy modification includes increasing the amplitude parameter value from first amplitude value 236 to second amplitude value 238. Processor 80 controls stimulation generator 84 to increase the amplitude of stimulation pulses delivered to patient 12 based on patient's posture state. Specifically, processor 80 may determine that a stimulation amplitude equal to that of second amplitude value 238 is appropriate based on one or more stimulation programs stored in memory 82 that correspond to the posture state of upright and active, as indicated by walking or other upright activity.

As indicated by the timing diagram shown in FIG. 12, IMD 14 may not instantaneously increase the amplitude parameter value of the stimulation therapy from amplitude 236 to amplitude 238 once the patient's posture state transition is detected and time period 224 expires. Instead, processor 80 controls stimulation generator 84 to transition the amplitude parameter of the stimulation therapy from first amplitude value 236 to second amplitude value 238 during a transition period 226. In particular, the amplitude parameter is ramped up from first amplitude value 236 to second amplitude value 238 beginning at the start of transition period 226, increasing at a rate of change equal to that of the slope of line 212 during transition period 226, i.e., the slope of ramp portion 244, and ending at approximately the end of transition period 226. The slope of portion 244 is equal to that of the difference 242 between first amplitude value 236 and second amplitude value 238, divided by the length of time period 226.

In this example, IMD 14 does not first drop the stimulation amplitude to approximately zero prior to ramping up the stimulation amplitude to second amplitude value 238. Instead, IMD 14 begins the stimulation amplitude adjustment to value 238 directly from first amplitude value 236. However, in some examples, other techniques may be employed. For example, instead of ramping up the stimulation intensity directly from value 236, IMD 14 may first drop to the stimulation amplitude to a lower value e.g., approximately zero, and then ramp up the stimulation amplitude to second value 238 to adjust the stimulation amplitude.

In general, the rate of change corresponding to the slope of portion 244 provides a gradual stimulation amplitude adjustment while maintaining effective stimulation therapy to patient 12. In some cases, if the amplitude value of stimulation therapy is increased too quickly, a patient may experience discomfort. In contrast, if the stimulation amplitude of stimulation therapy is modified too slowly, a patient may not be provided with appropriate stimulation therapy soon enough following a posture transition, leading to the patient experiencing symptoms that the modified therapy is meant to address. In this way, the transition period for the therapy modification affects the responsiveness of the posture responsive therapy provided by IMD 14. In some examples, the amplitude parameter value represented by line 212 may be increased during transition period 226 to allow for an adjustment of the stimulation amplitude value without resulting in patient discomfort. This may include patient discomfort as a result of increasing the amplitude value at too great of a rate, or increasing the amplitude value at too slow of a rate, as described.

In some examples in which the stimulation amplitude value is a voltage amplitude, the rate of change corresponding to the slope of portion 244 may be on the order of volts or millivolts per second. For example, the rate of change corresponding to the slope of portion 244 may range from approximately 1 volt per second to approximately 3 volts per second. In some cases, the rate of change corresponding to the slope of portion 244 may be inversely proportional to the length of dwell time period 244. Furthermore, in some examples, the length of time of transition period 226 may be on the order of minutes or seconds. For example, the length of time of transition period may range from approximately 0.1 seconds to approximately 10 seconds, such as approximately 0.5 seconds to approximately 2 seconds. In some examples, the amplitude difference represented by line 242 may be on the order of volts or millivolts in examples in which the stimulate amplitude value is a voltage amplitude. In some examples, the amplitude difference represented by line 242 may be up to approximately 10.5 volts. For example, the amplitude difference represented by line 242 may range from approximately 1 volt to approximately 3 volts, such as approximately 1.5 volts to approximately 2 volts.

In some cases, the suitability of a ramp adjustment may be unique to the type of posture state transition that results in the modification to the stimulation therapy. For example, the rate of change suitable for a ramp adjustment associated with an amplitude adjustment due to a patient's posture state transition from lying down to upright may be different than a rate of change for a ramp adjustment that is suitable for an amplitude adjustment based on the same patient's posture state transition from upright to upright and active. Consequently, in some examples, IMD 14 is configured to utilize a rate of change specific to the type of posture state transition that resulted in the therapy modification to adjust stimulation amplitude.

Just as different posture states may be associated with different amplitudes, different posture state transitions may be associated with different modification profiles, such as different ramp rates, transition periods, dwell times, and the like. In the example shown in FIG. 12, the rate of change during time period 226 may be defined based on the patient's transition from an upright posture state to an upright and active posture state. For other posture state transitions, such as upright to lying down, different rates of change and/or dwell times may be defined for modification of one amplitude value to another amplitude value. Such information may be stored in memory 82 of IMD 14, e.g., in a data table or another suitable data structure that associates a rate of change to one or more detectable posture state transitions. Processor 80 may access the therapy modification rate information upon detecting a patient posture change. In this manner, the modification may be made according to a particular ramp adjustment and/or dwell time that is appropriate based on the particular patient posture state transition that caused the modification in stimulation therapy.

To detect posture state transitions, for example, IMD 14 may periodically detect the posture state occupied by patient 12. In one example, processor 80 of IMD 14 compares the current posture state of patient 12 detected via posture state module 86 to a previously detected posture state of patient 12, e.g., the posture state detected just prior to the current posture state, which may be stored in memory 82. If the two detected posture states are the same, IMD 14 may continue to deliver electrical stimulation without modification. However, if the two detected posture states are different, processor 80 may modify the stimulation therapy by adjusting the amplitude parameter value according to a corresponding modification profile, e.g., as defined by the stimulation program corresponding to the new posture state occupied by patient 12, as described herein.

IMD 14 alternatively or additionally may be configured to utilize a rate of change and/or dwell time specific to the type of amplitude adjustment being made to adjust stimulation amplitude. In general, any amplitude adjustment made by IMD 14 may be characterized as either an increase or decrease in the stimulation amplitude value. Accordingly, in some examples, IMD 14 may adjust stimulation amplitude according to the same rate of change and/or dwell time for all amplitude adjustments that increase the amplitude value, and may also adjust stimulation amplitude according to the same rate of change for all amplitude adjustments that decrease the amplitude value. For example, IMD 14 may execute every amplitude increase according to substantially the same rate, regardless of the overall amplitude increase. As a result, in such cases, the transition period associated with the amplitude adjustment may vary according to the overall amplitude increase.

As another example, IMD 14 may be configured to utilize a rate of change and/or dwell time that is specific to each posture state occupied by a patient, rather than a posture state transition, to adjust stimulation amplitude. For example, IMD 14 may automatically adjust stimulation amplitude to a desired value according to approximately the same rate of change any time IMD 14 detects that patient is in a specific posture state. For example, IMD 14 may automatically adjust the stimulation amplitude to a desired value according to a specific rate of change any time IMD 14 detects that patient 12 is lying down, regardless of the previous posture state.

Although each of the provided examples describes adjusting stimulation amplitude using a rate of change that is specific to one or more factors, such as posture state transition, type of modification (i.e., increase or decrease), or posture state, in some examples, IMD 14 may be configured to adjust stimulation amplitudes using a length of the transition period that is specific to one or more factors, such as those described. For example, rather than adjusting a value of a stimulation parameter according to the same rate of change for all decreases in stimulation amplitude, IMD 14 may be configured to make any adjustment that is a decrease in stimulation amplitude over approximately the same time period. In such cases, the rate of change of the stimulation amplitude parameter from the initial to desired parameter value during the specified time period may be dependent on the overall difference between the initial and desired value, given the same period of time over which the change is to be made. In this manner, different transitions may be associated with different ramp rates, which are determined a function of the length of the time period and the magnitude of the amplitude change to be achieved over the time period.

The above examples present a wide variety of techniques for providing different modification profiles when a transition from one posture state to another posture state is detected. Such examples are provided for purposes of illustration and should not be considered limiting of the techniques as broadly described in this disclosure.

Referring again to FIG. 12, as previously mentioned, patient 12 occupies the upright and active posture state during time periods 224, 226, and 228. Once IMD 14 has increased the amplitude parameter value to second amplitude value 238 at approximately the end of transition period 226, the amplitude parameter is maintained at approximately value 238 throughout time periods 228 and 230. At time 246, patient 12 transitions to a posture state that corresponds to a stimulation therapy program specifying an amplitude parameter with third amplitude value 248. For example, the patient may transition from upright and active to a posture state corresponding to patient 12 in the lying position.

Processor 80 of IMD 14 detects the posture transition of patient 12 from upright and active posture state to a lying posture state during dwell time period 230, e.g., in a manner similar to that described with respect to the posture state transition detection during dwell time period 224. Dwell time period 230 may be defined by the modification profile corresponding to the posture state transition. Once processor 80 has detected the posture transition of patient 12, processor 80 automatically modifies the stimulation therapy, e.g., to effectively address the symptoms experienced by patient 12 while in the lying posture. As illustrated by line 212, the stimulation therapy modification may include decreasing the amplitude parameter value from second amplitude 238 to third amplitude value 248. For example, processor 80 may control stimulation generator 84 to decrease the amplitude of stimulation pulses delivered to patient 12 from second amplitude value 238 to third amplitude value 248, where the third amplitude value 248 is associated with the current patient posture state. Specifically, processor 80 may determine that a stimulation amplitude equal to that of third amplitude value 248 is appropriate based on one or more stimulation programs stored in memory 82 that correspond to the posture state of lying down. Patient 12 continues to occupy a lying down posture state during time period 234, in which IMD 14 continues to deliver stimulation therapy to patient 12 at amplitude value 248.

As indicated by the chart shown in FIG. 12, IMD 14 adjusts the stimulation parameter from second amplitude value 238 to third amplitude value 248 during time period 232 according to a modification profile that specifies the rate of change defined by the slope of portion 250 of line 212. In particular, the rate of change during time period 232 is approximately the negative of the absolute amplitude amount represented by line 252 divided by the amount of time represented by transition period 232, i.e., the slope of portion 250. Similar to portion 244 of line 212, the rate of change associated with portion 250 may be stored as a value in a look-up table in memory 82, and correspond to stimulation amplitude adjustments associated with a specific posture state transition from upright and active to lying down. In this manner, upon detecting that patient 12 has changed from upright and active to lying down, IMD 14 may adjust the stimulation amplitude to a level that provides effective stimulation therapy, and control the stimulation amplitude adjustment such that the amplitude value is adjusted according to the rate of change specified for the pertinent posture state transition.

In the example of FIG. 12, the modification profile for the upright and active to lying down posture state transition presents a slope associated with portion 250 that is much steeper than the slope of portion 244. That is, the modification profile for the upright and active to lying down posture state transition indicates a faster transition period than the modification profile for the upright to upright and active posture state transition. In some cases, an immediate increase or decrease in amplitude or other therapy parameter values may be desirable to mitigate potential patient discomfort that could be caused during a gradual increase or decrease. As previously mentioned, during the use of IMD 14 to treat patient 12, the transition of patient 12 among different posture states may affect the ability of IMD 14 to deliver consistent efficacious therapy. As one example, referring to FIG. 1A, the movement of patient 12 to a lying down position may affect the relative positioning of leads 16 with respect to the spinal cord 18 of patient 12.

In some examples, the length of time of transition period 232 may be on the order of seconds or milliseconds. For example, the length of time of transition period may range from approximately 100 milliseconds to approximately 30 seconds, such as approximately 100 milliseconds to approximately 150 milliseconds. In some examples, the length of time of transition period 232 may be substantially equal to that of the length of time required by IMD 14 to process and reconfigure one or more components to deliver stimulation according to respective stimulation amplitude adjustment. In some examples in which the stimulation amplitude value is a voltage amplitude, the amplitude difference represented by line 252 may be on the order of volts or millivolts in examples. In some examples, the amplitude difference represented by line 252 may be up to approximately 10.5 volts. For example, the amplitude difference represented by line 242 may range from approximately one volt to approximately three volts, such as approximately 1.5 volts to approximately two volts.

In some cases, when patient 12 lies down, leads 16 may be compressed towards the spinal cord 18 (FIG. 1A). As a result of the compression of leads 16 toward spinal cord 18, the amplitude of stimulation therapy may need to be decreased relatively quickly to a suitable amplitude value to minimize the possibility of causing patient 12 additional discomfort or unusual sensations. For example, in some cases, patient 12 may experience what can be described as a "buzz" sensation after lying down due to the compression of one or more leads of an IMD toward spinal cord 18. Furthermore, because the compression of lead 16 toward spinal cord 18 may substantially coincide with physical movement of patient 12 lying down, it may be desirable to reduce the stimulation amplitude to a suitable value in a relatively short amount of time to avoid patient 12 discomfort.

Consequently, in some examples, the stimulation amplitude may be decreased to a suitable amplitude value within a time period sufficient to prevent the patient from experiencing one or more of the undesirable effects that may result from a patient lying down. In addition, in such cases, it also may be desirable to reduce the delay period component of the dwell time so that the IMD may react more quickly to particular posture state transitions, such as transitions from upright to lying posture states.

In some examples, IMD 14 may automatically decrease the stimulation amplitude according to rate of change that provides for a substantially immediate decrease or drop to a suitable amplitude value when IMD 14 detects that patient 12 lies down, e.g., as shown in FIG. 12. For example, IMD 14 may automatically decrease the stimulation amplitude to a suitable value substantially simultaneously with the detection of patient 12 occupying a lying down posture state. With respect to FIG. 12, such an example is illustrated by portion 250 being substantially vertical. In other words, the amount of time in transition period 232 may be approximately zero. In this example, the time delay between patient 12 lying down and the decrease to a suitable stimulation amplitude is approximately the amount of time required for IMD 14 to detect that patient 12 is lying down, i.e., time period 230. The substantially immediate drop can be expressed in terms of an abrupt rate of change as determined by an aggressive slope in portion 250 and/or very short transition period 232.

In other examples, the stimulation amplitude may not be decreased substantially immediately by IMD 14, but instead may be decreased to a suitable amplitude value over a period of time that is sufficiently short to prevent patient 12 from experiencing undesirable stimulation effects as a result of receiving stimulation therapy having too great of stimulation amplitude. For example, transition period 232 may define an amount of a time that is less than the amount time in which patient 12 may experience undesirable effects from relating to the patient lying down. As the appropriate transition period may vary from patient to patient, IMD 14 may be programmed with a transition period value during a programming session that is defined based on actual patient 12 experiences from therapy delivered by IMD 14 in such a situation.

In some examples, the suitable amplitude value to which IMD 14 decreases stimulation when it is detected that patient 12 lies down may include an amplitude value of zero. By decreasing the amplitude value to zero, it can be ensured that IMD 14 will not supply stimulation to patient 12 at too great of stimulation amplitude. However, in some examples, rather than dropping stimulation amplitude to a value of substantially zero, IMD 14 may decrease the stimulation amplitude to the value defined by the stimulation corresponding to patient 12 occupying a lying posture state, such as illustrated by the stimulation amplitude decrease shown in FIG. 12.

Alternatively, IMD 14 may be programmed to decrease the stimulation amplitude value to a "safe" value that is greater than zero but that is such that patient 12 will not experience any significant negative side effects from the stimulation when lying down. While in some examples the "safe" value may be the same of the stimulation amplitude value defined by the stimulation program, in some cases it may be different. The "safe" value may be a preprogrammed value stored in memory 82 of IMD 14 and may be based on one or more factors, such as, e.g., previous patient experience. In some examples, the "safe" value may be modified after implantation of IMD 14 in patient based on the actual stimulation experiences of patient 12.

In examples utilizing such a "safe" value approach, processor 80 of IMD 14 may automatically decrease the stimulation amplitude value to the "safe" value whenever the patient occupies a lying posture state. Alternatively, processor 80 may automatically decrease the stimulation amplitude value to the "safe" value whenever an adjustment that involves a decrease in stimulation is determined, which may include when patient 12 is lying down, but also other therapy modifications that result in an overall stimulation decrease that are not necessarily as a result of patient 12 lying down.

In some examples, once IMD 14 has decreased the stimulation amplitude value to the "safe" value in an appropriate amount of time, e.g., to prevent patient 12 from experiencing undesirable side effects, processor 80 may make a further adjustment to the stimulation amplitude value that is defined by the stimulation program that corresponds to the posture state that patient 12 occupies. This amplitude adjustment may be according to a ramp that has a rate of change different than that employed to make the adjustment to the "safe" value.

For example, IMD 14 may ramp-up/ramp-down the stimulation amplitude from the "safe" value to the stimulation value defined by the stimulation program corresponding to patient's 12 posture state. As such, such a technique may have two transition periods associated with the adjustment, the first transition period having a rate of change appropriate for adjusting to the "safe" value, and the second transition period adjusting to the value defined by the stimulation program corresponding to the patient's detected posture state.

Alternatively, IMD 14 may be programmed to decrease the stimulation amplitude value to any value that is less than a minimum threshold value. This threshold value may represent the minimum amplitude value at which a patient may perceive effects from stimulation regardless of the patient posture state. Similar to that described above, this minimum threshold value may be preprogrammed but also modifiable based on patient experience such that the threshold value is patient specific. By lowering the stimulation amplitude value below the threshold value within an appropriate amount of time, patient should not experience any perceivable effects resulting from therapy delivered at too great of stimulation amplitude value.

As another example, if such a threshold value approach is used by an IMD, when the stimulation amplitude value defined by the stimulation program corresponding to a posture state occupied by the patient is less than the minimum threshold value, then the IMD may decrease the stimulation amplitude value to that value in an appropriate amount of time, e.g., substantially immediately, to prevent the patient from experiencing undesirable side effects. However, if the stimulation amplitude value defined by the stimulation program corresponding to the posture state occupied by the patient is greater than or equal to the minimum threshold value, IMD may first decrease the amplitude value to a value less than the threshold, e.g., such as the "safe" value described above, in an appropriate amount of time, e.g., substantially immediately. After that adjustment has been made, the IMD 14 may then adjust the stimulation amplitude to the value defined by the corresponding stimulation program by ramping up the stimulation at a suitable rate. Accordingly, similar to that described above, such an example may also be described as exhibiting two transition periods.

The rate of change appropriate for one or more adjustments made to the stimulation amplitude may vary from patient to patient. Factors that may influence the effects experienced by a patient due to stimulation may include, but are not limited to, the implant location of one or more leads with respect to the spinal cord of a patient and the relative impedance of the tissue separating the one or more leads and the spinal cord. Accordingly, as will be described in further detail below with respect to FIG. 13, in some examples, one or more properties relating to stimulation amplitude adjustments, e.g., the rate of amplitude change, may be tailored to a specific patient.

While the above examples have been described with respect to decreasing stimulation amplitude based on patient 12 occupying a lying down state, e.g., transitioning from upright and active to lying down, in some examples the techniques for decreasing stimulation amplitude may also be applied in any situation in which IMD 14 determines that a stimulation amplitude adjustment that decreases the stimulation amplitude value is warranted. In this manner, patient 12 may be guarded against receiving stimulation therapy from IMD 14 with a pulse amplitude that is too high as a result of a decrease in stimulation amplitude that is too low.

Figure 13:
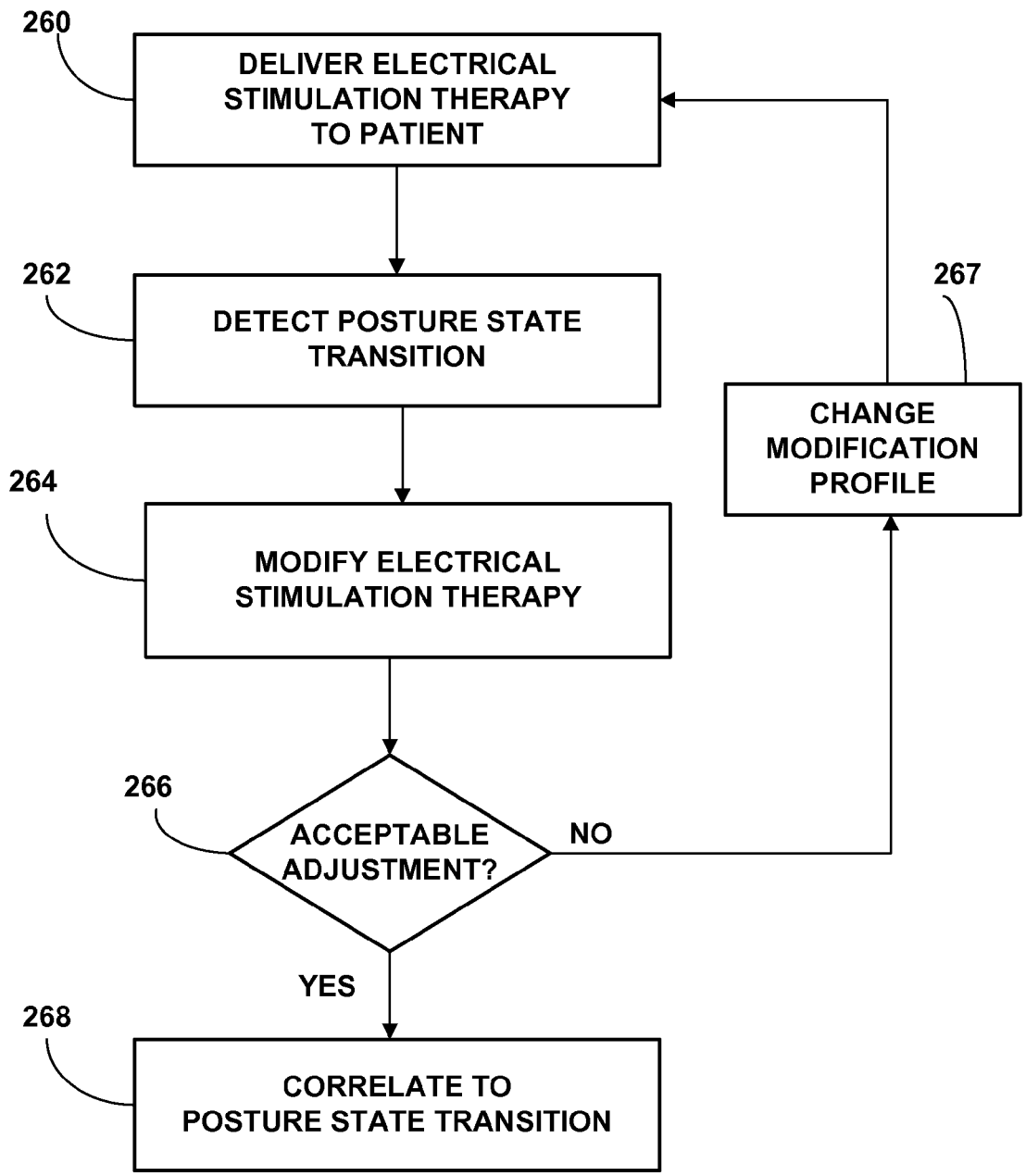
FIG. 13 is a flowchart illustrating an example technique for configuring one or more properties associated with a stimulation parameter adjustment.

FIG. 13 is a flowchart illustrating an example technique for configuring one or more properties associated with a modification profile for a stimulation parameter adjustment implemented based on a detected patient posture transition. The technique shown in FIG. 13 may be utilized to configure the rate of change associated with a stimulation parameter adjustment on a patient-specific basis. Such a technique may be utilized by a clinician during a programming session with patient 12 via clinician programmer 60 or, alternatively, may be carried out on a periodic basis by patient 12, e.g., using patient programmer 30.

IMD 14 delivers electrical stimulation therapy having a first stimulation amplitude value to patient 12 while patient 12 occupies a first posture state (260). In general, the first stimulation amplitude value may be appropriate for the posture state occupied by patient 12 at the time the therapy is delivered. For example, if patient 12 is in an upright posture state, then IMD 14 delivers stimulation therapy having a stimulation amplitude value appropriate for when patient 12 is standing. In some examples, processor 80 of IMD 14 automatically selects the therapy program defining the stimulation parameter values that provide efficacious therapy to patient 12 when patient 12 is in the first posture state from memory 82 (FIG. 4) of IMD 14. Memory 82 associates a plurality of patient posture states with therapy programs known to provide efficacious therapy to patient 12 when patient 12 is in the respective posture state.

When patient 12 undertakes a posture state transition, IMD 14 detects the posture state transition via posture state module 86 (262). In some examples, processor 80 detects a posture state transition by comparing a currently-detected posture state to a previously-detected posture state. In other examples, patient 12 may provide input via programmer 20 that indicates that patient 12 has transitioned to another posture. Additionally or alternatively, processor 80 may detect a posture state transition based on a particular behavior of one or more sensors signals, e.g., accelerometer signals, associated with posture state module 86, which is indicative of a particular posture state transition. IMD 14 modifies the stimulation therapy based on a predetermined modification profile for the detected posture state transition (264). In particular, processor 80 may modify a therapy parameter value of the electrical stimulation therapy such as amplitude to a value associated with the new posture state (264). The modification may be performed according to a modification profile associated with the particular posture state transition. Memory 82 of IMD 14 or another device (e.g., programmer 20) may store associations between posture state transitions and modification profiles. The modification profile may specify, for example, a rate of change for a ramp and/or a dwell time to implement the modification of the parameter.

In some examples, processor 80 modifies the electrical stimulation therapy (264) by adjusting stimulation amplitude according to a first rate of change specified by an existing modification profile for the posture state transition. Initially, IMD 14 may adjust the stimulation amplitude according to a default rate of change. For example, the rate of change may be predefined based on previous patient testing. As another example, the rate of change may be predetermined to provide an amplitude adjustment with relatively high efficiency, e.g., with respect to battery consumption. As another example, the rate of change used may be similar to that used by IMD 14 to adjust stimulation amplitude based on other patient posture transitions.

The specific rate of change that is suitable for an amplitude adjustment may depend on one or more patient specific factors. In accordance with the technique shown in FIG. 13, the modification profile may be adjusted to be more specific to patient 12. Patient 12 evaluates the acceptability of the stimulation amplitude adjustment (266) that was made as part of the therapy modification based on the detected patient activity, e.g., the posture state transition from standing to walking. For example, if the patient found the amplitude adjustment to be acceptable, e.g., there were substantially no noticeable negative side effects or symptoms experienced during the transition period, then the specific rate of change used by processor 80 to adjust the stimulation amplitude is correlated (or associated) with the respective posture state transition for which the therapy modification was based (268), e.g., using one or more suitable techniques to program IMD 14 using programmer 60 or 30. IMD 14 may use the same rate of change in the future when adjusting stimulation amplitude based on a transition from upright to upright and active.

If the adjustment was determined to be unacceptable, e.g., patient 12 experienced one or more negative side effects or symptoms during the transition period, the rate of change value and/or dwell time specified by the modification profile and used for the stimulation amplitude adjustment is changed (267), i.e., increased or decreased, and the process may be repeated using the new rate of change. A determination of whether the automatic stimulation adjustment was acceptable or not may be determined directly from interaction with the patient. In some cases, a clinician manually changes the rate of change value and/or dwell time used for amplitude adjustments by communicating with IMD 14 via programmer 60 to specify desired changes to the modification profile that was previously used to modify stimulation delivered to patient 12. In other cases, patient 12 may be allowed to specify changes to the modification profile, e.g., by communicating with IMD 14 via programmer 30. The patient programmer could also define the transition table.

The rate of change value and/or dwell time may be changed based at least in part on patient feedback with respect to the previous amplitude adjustment. In some examples, the clinician may revise the amplitude rate of change and/or dwell time based on experience. For example, if patient 12 experiences effects that are consistent with a rate of change that is too slow, the clinician may increase the rate of change from the previously specified value. Alternatively, if the patient 12 experience is consistent with a rate of change that is too fast, the clinician may decrease the rate of change from the previously specified value. In another example, the rate of change value may be revised based on stimulation efficiency. For example, the revised rate of change value may be the next most efficient rate of change compared to the previously applied rate of change value, which was determined to be unacceptable.

A process such as that illustrated in FIG. 13 may be repeated, e.g., in a clinic, until an acceptable rate of change or dwell time is determined for amplitude adjustment for the posture state transition. Further, such a process may be repeated to determine rate of change values and/or dwell times specific to one or more different posture state transitions that results in an adjustment to stimulation amplitude. In this manner, the properties of the stimulation parameter adjustments corresponding to specific therapy modifications may be defined on a patient-specific basis.

Figure 14:
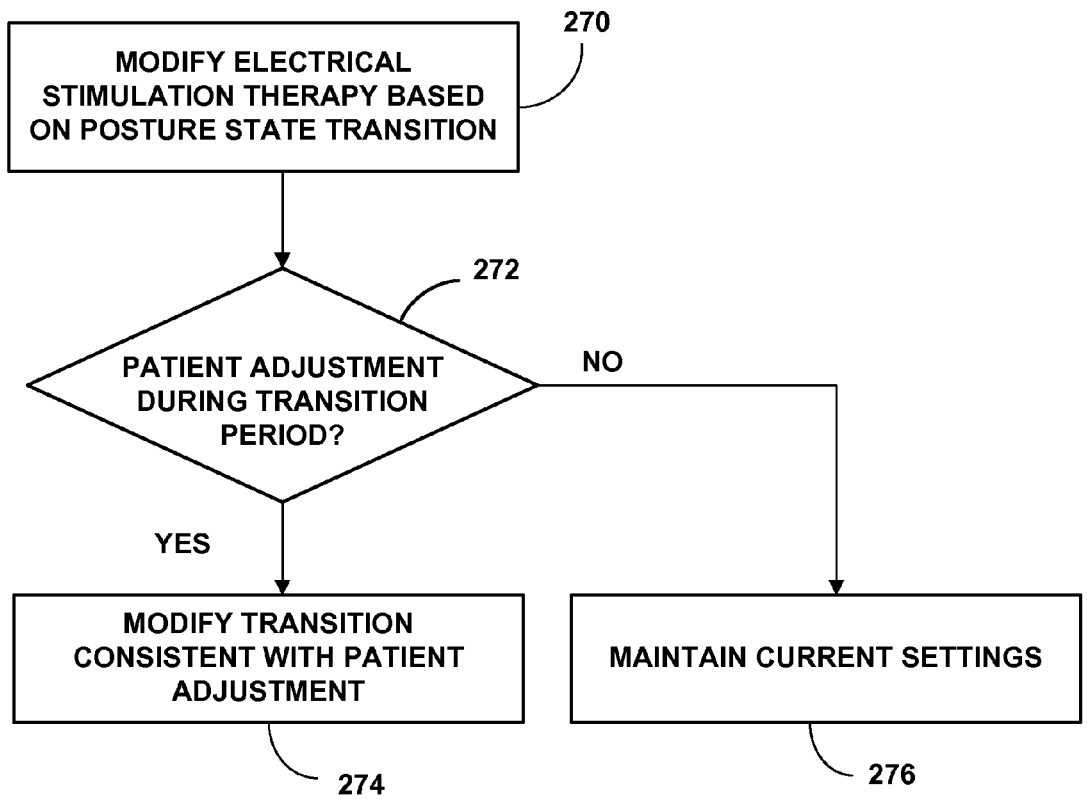
FIG. 14 is a flowchart illustrating an example technique for configuring a stimulation parameter adjustment based on patient action.

FIG. 14 is a flowchart illustrating an example technique for configuring a modification profile based on patient action. Although such a technique may be utilized during a clinician programming session, in some examples, it also may be utilized outside a clinician programming setting. In particular, such a technique may be utilized to continuously or periodically configure one or more properties associated with therapy modifications based on patient activity. In some situations, the suitability of one or more properties associated with a stimulation amplitude adjustment may change over time, e.g., as a result of lead migration within patient 12 and/or fibrosis near one or more implanted leads. For example, as described with respect to FIG. 14, the suitability of the rate of change value associated with one or more stimulation amplitude adjustments carried out by IMD 14 may change from that originally programmed.

As indicated by FIG. 14, IMD 14 modifies electrical stimulation therapy based on a detected posture state transition (270). Such a modification may include the increase or decrease of stimulation amplitude. IMD 14 is configured to adjust the stimulation amplitude according to a specific rate of change specified by a modification profile for the respective posture state transition. Generally, the stimulation amplitude adjustment may not be perceived by patient 12, or the patient may find the respective adjustment to be acceptable at the rate of change over which it is provided. In such cases, IMD 14 will make future stimulation amplitude adjustments according to the programmed rate of change value (276).

In some cases, while IMD 14 is in the process of adjusting the stimulation amplitude according to the stored modification profile for the detected posture state transition, i.e., during the transition period, patient 12 provides an indication that the adjustment is not acceptable. For example, patient 12 may attempt to modify the stimulation amplitude parameter via programmer 30 (272) and, in effect, override the modification profile. Based on this patient action, IMD 14 may determine that the existing modification profile is not acceptable to the patient, and, accordingly, may modify one or more of the properties of the modification profile based on the patient. The adjustment to the modification profile can be consistent with the nature of the patient action. For example, if IMD 14 is in the process of increasing a stimulation amplitude when patient 12 attempts to manually increase the stimulation amplitude before the transition period is over, processor 80 of IMD 14 or another device may infer that the adjustment is not being made within an acceptable amount of time, i.e., not quickly enough.

In such cases, IMD 14 may automatically modify one or more properties associated with the amplitude adjustment consistent with the attempted patient adjustment (274) to address the apparent shortcoming. For example, IMD 14 may increase the rate of change value and/or reduce the dwell time specified for the respective stimulation amplitude adjustment such that the adjustment is completed over a shorter period of time, e.g., an amount of time that allows the overall adjustment to be completed prior to the time corresponding to the attempted modification by the patient. The adjustment may in effect change the modification profile defined for the posture state transition. A similar approach may be taken in cases involving a decrease in stimulation amplitude in which the patient attempts to manually decrease the stimulation amplitude during the transition period. In this manner, IMD 14 may automatically modify the rate of change value used for stimulation amplitude adjustments based on patient action.

In general, a determination of whether the automatic stimulation adjustment was acceptable or not may be inferred from patient action or inaction. If the patient made a further adjustment during the transition period, it may be inferred that the rate of the automated adjustment was not acceptable and that the modification profile for the subject posture state transition should be modified, e.g., by automatically adjusting the slope of the ramp and/or dwell time, if applicable. If the patient did not make any further adjustment, it may be inferred that the automated adjustment was acceptable.

In some examples, rather than automatically modifying the rate of change value for the stimulation amplitude adjustment when a patient attempts to modify the stimulation during a transition period or dwell time, IMD 14 flags the patient adjustment and stores the information in memory 82. This information may later be accessed by a clinician, who may then determine whether the rate of change value and dwell time defined by the modification profile for a particular patient state transition should be changed. In this case, the adjustment of the modification profile is not automatic, but rather clinician-supervised. In other examples, IMD 14 may automatically modify the rate of change value similar to that described, but only after a specific amount of flagged patient adjustments have identified for a respective transition period.

In some examples, patient 12 may attempt to adjust the stimulation amplitude parameter during a dwell time period, e.g., such as dwell time 224 of FIG. 12, following a posture state transition. For example, a patient may transition posture states and then attempt to modify the stimulation amplitude via programmer 30 before the dwell time period has expired. In such cases, IMD 14 is configured to recognize such a situation and respond to the situation in an appropriate manner. In some examples, IMD 14 responds by beginning the stimulation amplitude adjustment according to the corresponding modification profile as if the dwell time had expired upon receiving the patient input that indicates patient 12 is attempting to modify the stimulation amplitude. In other examples, IMD 14 responds by adjusting the stimulation to the final stimulation amplitude value substantially immediately and/or at an appropriate rate of change, rather than according the modification profile corresponding to the posture state transition, upon detecting that the patient attempted to modify the stimulation amplitude. In some examples, the dwell time may be reduced for the modification profile based on the patient therapy adjustment.

In other examples, IMD 14 ignores the patient's attempt to adjust the stimulation amplitude and, instead waits for the dwell time to expire and adjusts the stimulation amplitude according to the corresponding modification profile at that time. In other examples, IMD 14 responds by adjusting the stimulation amplitude upward or downward to the value indicated by patient 12 and stay at that value even when the dwell time expires. In other examples, IMD 14 responds by adjusting the stimulation amplitude to the value indicated by patient 12, but then makes a further adjustment from that amplitude value to the final amplitude value programmed for the posture state when the dwell time expires, e.g., according to the modification profile corresponding to the posture state transition.

As described above, a stimulation therapy system may utilize one or more dwell times defined by a modification profile to determine when to adjust the stimulation therapy based on the detected patient posture transition. Again, a dwell time may include one or time periods utilized by IMD 14 to determine if patient 12 has occupied a posture state for an amount of time appropriate for which to modify stimulation based on that posture state. For example, the dwell time may include a detect period and a delay period. IMD 14 may classify a posture state as either being a stable posture state or an unstable posture state. For example, IMD 14 may classify a posture state that has been detected but has not satisfied an associated dwell time requirement as an unstable posture state. Conversely, IMD 14 may classify a posture state that has been detected and also has satisfied an associated dwell time requirement as a stable posture state.

In some examples, IMD 14 is configured to commence adjustment of one or more therapy parameters only after a posture state transition results in a stable posture state. For example, IMD 14 may detect a first posture transition from active to active and upright, followed shortly thereafter by another posture transition from active and upright to upright. In this type of example, rather than automatically modifying the stimulation therapy when it is detected that patient 12 is active and upright, IMD 14 may classify the posture state as unstable and suspend the modification until the dwell time has passed before modifying the stimulation.

If, after the dwell time has passed, IMD 14 detects that patient 12 is still upright and active, IMD 14 may classify the upright and active posture state as a stable posture state and, therefore, modify the stimulation to correspond to the active and upright posture state. However, in a situation such as that described, if patient 12 is no longer active at the end of the dwell time, IMD 14 may not modify the therapy because the failure of patient 12 to maintain the posture state during the dwell time indicates that patient 12 did not occupy the upright and active posture state for the minimum time required for IMD 14 to classify it as a stable posture state. Instead, IMD 14 may continue deliver stimulation therapy according to the most recent stable posture state, i.e., upright in this example. In this manner, IMD 14 may only modify stimulation therapy as defined by the stimulation program associated with a detected posture state when the posture state is recognized as a stable posture state.

However, in some examples, IMD 14 may be configured to adjust one or more stimulation parameters of stimulation therapy prior to patient 12 occupying a stable posture state. In particular, it is recognized that in some examples, especially those relating to the detection of a posture state by IMD 14 that would result in a decrease in stimulation amplitude according to the specified therapy modification, it is appropriate for IMD 14 to decrease the stimulation amplitude before the dwell time has elapsed instead of remaining at stimulation amplitude according to the most recent stable posture state. In such a manner, patient 12 may be prevented from receiving stimulation therapy having a stimulation amplitude that is too high, and potentially uncomfortable.

Consequently, in some examples, IMD 14 may be configured to automatically decrease the stimulation amplitude to a lower amplitude value when IMD 14 first detects an unstable posture state of patient 12 rather than wait for the posture state to stabilize upon expiration of the dwell time, or remain at the stimulation amplitude value of the most recently detected stable posture state. Hence, IMD 14 may gradually or abruptly drop the stimulation amplitude to a lower amplitude before the dwell time has elapsed in order to reduce the possibility that patient 12 may experience discomfort when he occupies the next posture state. In some examples, IMD 14 is configured such that the stimulation amplitude value is adjusted to a lower stimulation amplitude only when the detected, unstable posture state defines a stimulation amplitude value that is lower than the amplitude value for the most recent stable posture state.

Hence, in summary, IMD 14 can be configured to respond to a transient patient posture state transition that occurs during the dwell time by switching to the lower therapy level (or temporarily turning off therapy) in any instance in which the sensed parameter indicates that the patient is transitioning to a posture state (posture or posture/activity) that would call for a lower therapy level per the stored therapy parameter values for that posture state. This provision may be added to compensate for the lag between initial sensing of the posture state transition, i.e., a change in the sensed posture state, and expiration of the dwell time. If patient 12 is in the sensed posture state upon expiration of the dwell time, IMD 14 concludes that the sensed posture state change indicates a stable posture state, rather than just a transient event associated with an unstable posture state.

Figure 15:
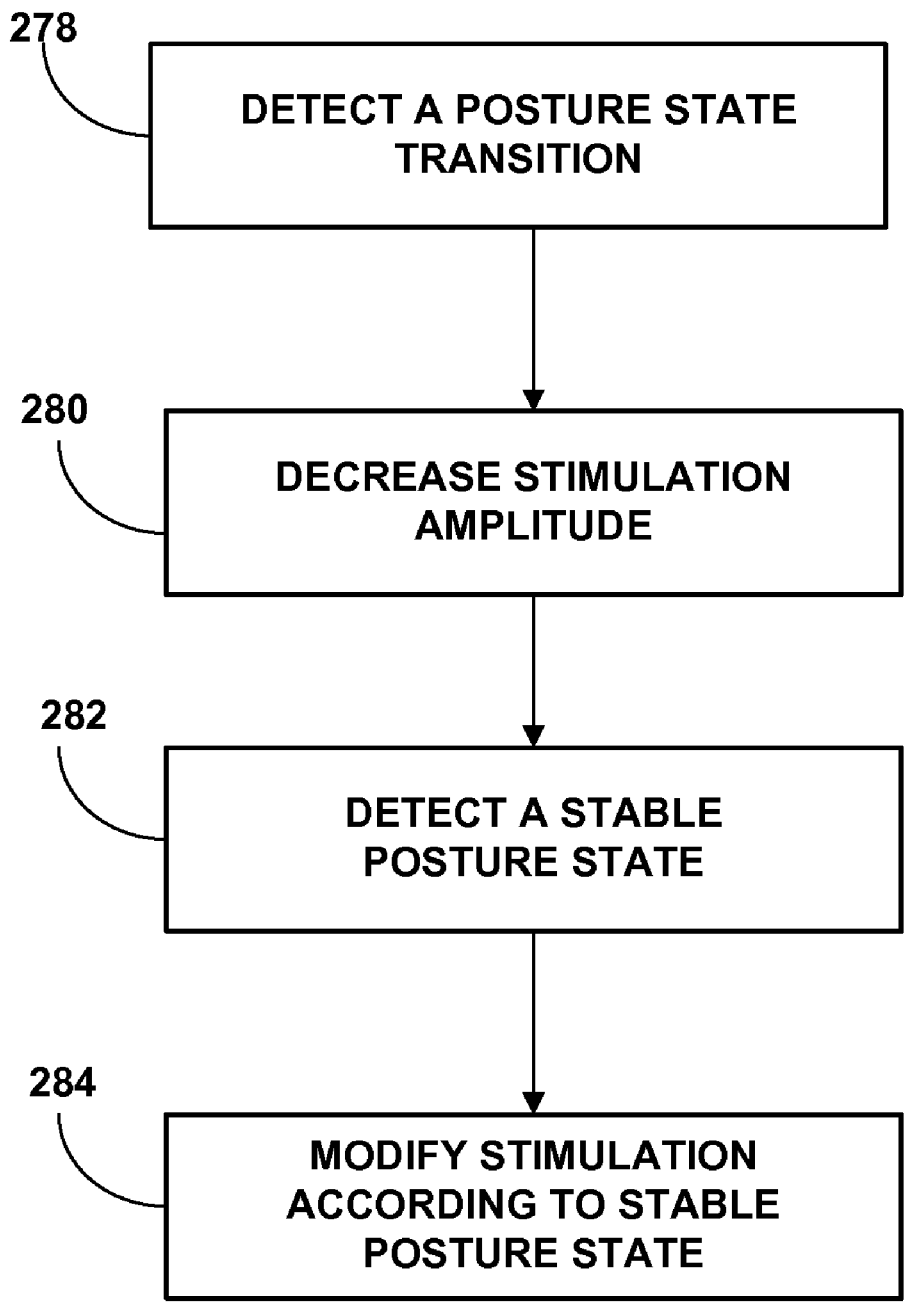
FIG. 15 is a flowchart illustrating an example technique for adjusting stimulation amplitude based on a patient posture state.

FIG. 15 is a flowchart illustrating an example technique for adjusting stimulation amplitude based on a patient posture state. In some examples, IMD 14 is configured to automatically decrease stimulation amplitude of stimulation therapy when IMD 14 detects that patient 12 has transitioned to an unstable posture state rather than waiting to adjust the stimulation amplitude when IMD 14 detects a stable posture state following expiration of the dwell time.

As illustrated in FIG. 15, IMD 14 detects that patient 12 has undertaken a posture state transition from a stable posture state (278). For example, IMD 14 may detect that patient 12 has transitioned from walking (upright and active) to standing (upright). While IMD 14 may determine that the upright posture state is an unstable posture state, e.g., based on the failure of patient 12 to maintain the upright posture state for the duration of the defined dwell time, IMD 14 may modify therapy in response to detecting the posture state transition. In the example shown in FIG. 15, IMD 14 automatically decreases the stimulation amplitude value from the stimulation value that was being delivered while patient 12 occupied an upright and active posture state (280). Such an adjustment may be accomplished according to one or more of the techniques described herein, e.g., by decreasing the amplitude substantially immediately or more gradually.

In general, the lower stimulation amplitude value may be selected such that the amplitude of the stimulation therapy delivered to patient 12 it not too high, e.g., to avoid possible over stimulation of patient 12. In some examples, the lower amplitude value may be zero. As another example, the lower amplitude value may be based on a minimum perception threshold for the patient. As another example, the lower amplitude value may be the lowest amplitude value defined in any stimulation program stored in memory 82. As another example, the lower amplitude value may be a "safe" value as previously described.

As another example, the lower amplitude value may be an amplitude value corresponding to the unstable posture state that has been detected. In examples in which IMD 14 detects that patient 12 has occupied more than one unstable posture state since the latest detected stable posture state, e.g., a transition from walking to briefly standing to briefly lying down, IMD 14 may adjust the stimulation therapy to the lowest amplitude value associated with the multiple unstable posture states.

In any case, IMD 14 continues to deliver stimulation therapy at the lower amplitude value until IMD 14 detects that patient 12 is occupying a stable posture state (282). For example, patient 12 may occupy the posture state of standing long enough to fulfill a defined dwell time. Once IMD 14 has detected the stable posture state, IMD 14 automatically modifies the stimulation therapy based on the stable posture state (284), including adjusting the stimulation amplitude value from the lower amplitude value to which IMD 14 adjusted when an unstable posture state was occupied by patient 12 to the stimulation amplitude value as defined by the stable posture state, e.g., as defined by the stimulation program associated with the stable posture state. The adjustment to the desired stimulation amplitude value may be carried out using one or more of the techniques described herein, e.g., ramping during a transition period.

As previously described, the lower amplitude value to which IMD 14 automatically decreases stimulation therapy when an unstable posture state is detected may be selected to avoid over stimulation of patient 12. However, it is also recognized that in some cases, the lower the amplitude value to which IMD 14 transitions therapy delivery upon detection of an unstable posture state, the greater the overall amplitude adjustment is required once a stable posture state is detected. In some cases, it is desirable to minimize the overall amplitude adjustment associated with such an amplitude modification. For example, as the overall amplitude adjustment increases, the relative amount of power consumption required for an amplitude adjustment may also increase. Furthermore, the relative degree to which a patient perceives an amplitude adjustment may increase as the overall amplitude adjustment increases. Accordingly, in some examples, the lower amplitude value that IMD 14 automatically decreases to upon detection of an unstable posture state may be greater than zero. For example, as previously described, the lower amplitude value may be equal to that of the lowest amplitude value defined by any program stored in memory 82. As another example, as previously described, the lower amplitude may be defined by the lowest amplitude value associated with one or more unstable posture states occupied by patient 12 since the last detected stable posture state. In this manner, the overall adjustment made to the stimulation amplitude by IMD 14 once patient 12 occupies a stable posture state may be minimized.

While examples of modification profiles have been primarily described as exhibiting substantially linear profiles, i.e., approximately constant rate of change over the transition period, example modification profiles are not limited as such. In some examples, a modification profile may exhibit a non-linear profile over all or portions of a transition period. For example, a modification profile may define an adjustment such that the rate of change exponentially increases over first portion and then exponentially decays over a last portion such that the stimulation amplitude value gradually approaches the final amplitude value after changing at a relative high rate. Furthermore, in some examples, a modification profile is defined for each of a plurality of sub-periods that make up an overall transition period. For example, a transition period having a length of approximately X seconds may be divided equally into 10 sub-periods, each being approximately one-tenth of X seconds in length. In such cases, a specific rate of change may be defined for each sub-period, such that the modification profile exhibits up to 10 different rates of change over the entire transition period. Using such techniques, a modification profile may be further tailored, e.g., based on specific patient experience, therapy type, and the nature of the amplitude adjustment. A modification profile need not conform to any equation, but may be any waveform shape desired by a patient as may be stored as a waveform description (e.g., waveform plot) or profile in memory of an IMD, for example. In any case, examples of the disclosure are not limited to modification profiles which exhibit a substantially linear profile over a transition period.

Furthermore, although examples of the disclosure are described as automatically adjusting stimulation amplitude according to the posture state of a patient detected by a posture state module, in some examples, an IMD may be configured to adjust stimulation as described herein based on patient input, e.g., sent via programmer 30. In particular, an IMD may be configured to receive an indication from a patient, e.g., via an external programmer, that the patient is about to enter or have recently entered a specific posture state. Upon receiving this indication, an IMD may modify therapy based on the indicated posture state, such as by increasing or decreasing the stimulation amplitude values. In one example, a patient may communicate to an IMD that they are about to enter a lying posture state by depressing a single button on a patient programmer before they lie down and, in response, the IMD may substantially immediately decrease the stimulation amplitude to a value appropriate to be delivered to the patient when lying down. In this manner, the IMD may appropriately decrease the stimulation amplitude when patient 12 enters a lying posture state according to a patient-directed adjustment rather than a posture state transition detected by a posture state module.

The techniques described in this disclosure may be implemented, at least in part, in hardware, software, firmware or any combination thereof. For example, various aspects of the techniques may be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as RAM, ROM, NVRAM, EEPROM, FLASH memory, magnetic media, optical media, or the like. The instructions may be executed to support one or more aspects of the functionality described in this disclosure.

In addition, it should be noted that the systems described herein may not be limited to treatment of a human patient. In alternative examples, these systems may be implemented in non-human patients, e.g., primates, canines, equines, pigs, and felines. These animals may undergo clinical or research therapies that my benefit from the subject matter of this disclosure.

Many examples have been described. Various modifications may be made without departing from the scope of the claims. These and other examples are within the scope of the following claims.

The invention claimed is:

1. A method comprising:
controlling the delivery of therapy to a patient from a medical device according to a posture state of the patient;
detecting a first posture state transition of the patient;
modifying the therapy according to a first modification profile defined for the first posture state transition, wherein the first modification profile defines a first rate of change for an adjustment of at least one parameter of the therapy delivered to the patient;
detecting, subsequently, a second posture state transition of the patient; and
modifying the therapy according to a second modification profile defined for the second posture state transition, wherein the second modification profile defines a second rate of change for an adjustment of the at least one parameter of the therapy delivered to the patient that is different than the first rate of change defined by the first modification profile, and
wherein at least one of the controlling, detecting, determining, and modifying are performed via one or more processors.

2. The method of claim 1, wherein the therapy includes electrical stimulation therapy, and wherein the at least one parameter of the therapy comprises at least one stimulation parameter value of the electrical stimulation therapy.

3. The method of claim 1, wherein the first posture state transition comprises a transition from an upright posture state to an upright and active posture state, and the second posture state transition comprises a transition from the upright posture state to a lying down posture state, and wherein the first rate of change is less than the second rate of change.

4. The method of claim 3, wherein the second rate of change defines a substantially immediate change in the at least one parameter from a first value associated with the upright posture state to a second value associated with the lying down posture state.

5. The method of claim 2, wherein the first rate of change includes a third rate of change and a fourth rate of change for the adjustment to the at least one stimulation parameter value.

6. The method of claim 5, wherein the third rate of change defines a first change in the at least one stimulation parameter value from a first value associated with a first posture state to an intermediate value, and the fourth rate of change defines a second change in the at least one stimulation parameter value from the intermediate value to a second value associated with a second posture state.

7. The method of claim 6, wherein the third rate of change in the at least one stimulation parameter value from the first value to the intermediate value is substantially immediate.

8. The method of claim 6, wherein the intermediate value is less than the first value and the second value.

9. The method of claim 6, wherein the intermediate value is associated with an unstable posture state and the second posture state is a stable posture state.

10. The method of claim 1, wherein detecting the first posture state transition of the patient comprises detecting the first posture state transition via at least one accelerometer.

11. The method of claim 1, wherein modifying the therapy according to the first modification profile defined for the first posture state transition includes adjusting at least one therapy parameter value according to the first rate of change during a transition time period, the method further comprising
receiving an indication from a user during the transition time period, wherein the first modification profile is changed to define a third rate of change that is greater than the first rate of change in response to the receipt of the indication from the user during the transition time period.

12. The method of claim 1, wherein the adjustment to the at least one therapy parameter defined by the first rate of change commences after expiration of a dwell time period following the detection of the first posture state transition, wherein the dwell time is defined by the first modification profile.

13. The method of claim 12, further comprising:
receiving an indication from a user during the dwell time period; and
adjusting the dwell time period defined by the first modification profile such that the dwell time period expires substantially immediately after receiving the indication from the user.

14. The method of claim 1, wherein the first modification profile defines a dwell time for the therapy modification.

15. The method of claim 1, wherein the first modification profile defines a length of time for the adjustment to the at least one parameter.

16. The method of claim 1,
wherein the first posture state transition comprises a first posture state transition from a first posture state to a second posture state,
the method further comprising determining the first modification profile defined for the posture state transition based on one or more of the first posture state and second posture state.

17. The method of claim 16, wherein determining the first modification profile based on one or more of the first posture state and second posture state comprises determining the modification profile based on only one of the first posture state and second posture state.

18. The method of claim 1, further comprising:
receiving an indication from a user defining the first modification profile; and
defining the first modification profile based on the received indication.

19. The method of claim 1, further comprising:
receiving an indication from a user defining the first posture state transition for the first modification profile; and
defining the first posture state transition for the first modification profile based on the received indication.

20. The method of claim 1, wherein the first posture state transition comprises a transition from a first posture state to a second posture state, and the second posture state transition comprises a transition from the second posture state to the first posture state.

21. A therapy system comprising:
a therapy delivery module configured to deliver therapy to a patient from a medical device; and
at least one processor configured to control the delivery of therapy to the patient from the medical device according to a posture state of the patient, detect a first posture state transition of the patient, modify the therapy according to a first modification profile defined for the first posture state transition, wherein the first modification profile defines a first rate of change for an adjustment of at least one parameter of the therapy delivered to the patient, detect, subsequently, a second posture state transition of the patient, and modify the therapy according to a second modification profile defined for the second posture state transition, wherein the second modification profile defines a second rate of change for an adjustment of the at least one parameter of the therapy delivered to the patient that is different than the first rate of change defined by the first modification profile.

22. The therapy system of claim 21, wherein the therapy includes electrical stimulation therapy, and wherein the at least one parameter of the therapy comprises at least one stimulation parameter value of the electrical stimulation therapy.

23. The therapy system of claim 21, wherein the first posture state transition comprises a transition from an upright posture state to an upright and active posture state, and the second posture state transition comprises a transition from an upright posture state to a lying down posture state, and wherein the first rate of change is less than the second rate of change.

24. The therapy system of claim 23, wherein the second rate of change defines a substantially immediate change in the at least one stimulation parameter from a first value associated with the upright posture state to a second value associated with the lying down posture state.

25. The therapy system of claim 22, wherein the first rate of change includes a third rate of change and a fourth rate of change for the adjustment to the at least one stimulation parameter value.

26. The therapy system of claim 25, wherein the third rate of change defines a first change in the at least one stimulation parameter value from a first value associated with a first posture state to an intermediate value, and the fourth rate of change defines a change in the at least one stimulation parameter value from the intermediate value to a second value associated with a second posture state.

27. The therapy system of claim 26, wherein the third rate of change in the at least one stimulation parameter value from the first value to the intermediate value is substantially immediate.

28. The therapy system of claim 26, wherein the intermediate value is less than the first value and the second value.

29. The therapy system of claim 26, wherein the intermediate value is associated with an unstable posture state and the second posture state is a stable posture state.

30. The therapy system of claim 21, wherein the posture state module comprises at least one accelerometer, and the at least one processor is configured to detect the posture state transition of the patient via the at least one accelerometer.

31. The therapy system of claim 21, wherein the at least one processor is configured to adjust the at least one therapy parameter during a transition time period according to the first rate of change, receive an indication from a user during the transition time period and change the first modification profile to define a third rate of change that is greater than the first rate of change in response to the receipt of the indication from the user during the transition time period.

32. The therapy system of claim 21, wherein the at least one processor is configured to adjust the at least one therapy parameter after expiration of a dwell time period following the detection of the first posture state transition, wherein the dwell time is defined by the first modification profile.

33. The therapy system of claim 32, wherein the at least one processor is configured to receive an indication from a user during the dwell time period, and adjust the dwell time period defined by the first modification profile such that the dwell time period expires substantially immediately after receipt of the indication from the user in response to receipt of the indication.

34. The therapy system of claim 21, wherein the modification profile defines a dwell time for the therapy modification.

35. The therapy system of claim 21, wherein the first modification profile defines a length of time for the adjustment to the at least one parameter value.

36. The therapy system of claim 21, wherein the first posture state transition comprises a transition from a first posture state to a second posture state, and wherein the at least one processor is configured to determine the first modification profile defined for the posture state transition based on one or more of the first posture state and the second posture state.

37. The therapy system of claim 36, wherein the at least one processor is configured to determine the modification profile based on only one of the first posture state and the second posture state.

38. The therapy system of claim 21, wherein the at least one processor is configured to receive an indication from a user defining the first modification profile, and define the first modification profile based on the received indication.

39. The therapy system of claim 21, wherein the at least one processor is configured to receive an indication from a user defining the first posture state transition for the modification profile, and define the first posture state transition for the modification profile based on the received indication.

40. The therapy system of claim 21, wherein the first posture state transition comprises a transition from a first posture state to a second posture state, and the second posture state transition comprises a transition from the second posture state to the first posture state.

41. A non-transitory computer-readable storage medium comprising instructions for causing one or more processors to:
control a medical device to deliver therapy to a patient according to a posture state of the patient;
detect a posture state transition of the patient;
modify the therapy according to a first modification profile defined for the first posture state transition, wherein the first modification profile defines a first rate of change for an adjustment of at least one parameter of the therapy delivered to the patient
detect, subsequently, a second posture state transition of the patient; and
modify the therapy according to a second modification profile defined for the second posture state transition, wherein the second modification profile defines a second rate of change for an adjustment of the at least one parameter of the therapy delivered to the patient that is different than the first rate of change defined by the first modification profile.

42. A therapy system comprising:

means for controlling the delivery of therapy to a patient from a medical device according to a posture state of the patient;

means for detecting a posture state transition of the patient;

means for modifying the therapy according to a first modification profile defined for the first posture state transition, wherein the first modification profile defines a first rate of change for an adjustment of at least one parameter of the therapy delivered to the patient means for detecting, subsequently, a second posture state transition of the patient; and means for modifying the therapy according to a second modification profile defined for the second posture state transition, wherein the second modification profile defines a second rate of change for an adjustment of the at least one parameter of the therapy delivered to the patient that is different than the first rate of change defined by the first modification profile.

* * * * *